US012168769B2

(12) United States Patent
Jiang

(10) Patent No.: US 12,168,769 B2
(45) Date of Patent: *Dec. 17, 2024

(54) METHODS FOR GENOMIC INTEGRATION IN *PICHIA* AND OTHER HOST CELLS

(71) Applicant: Amyris, Inc., Emeryville, CA (US)

(72) Inventor: Hanxiao Jiang, Fremont, CA (US)

(73) Assignee: Amyris, Inc., Emeryville, CA (US)

( * ) Notice: Subject to any disclaimer, the term of this patent is extended or adjusted under 35 U.S.C. 154(b) by 181 days.

This patent is subject to a terminal disclaimer.

(21) Appl. No.: 17/841,429

(22) Filed: Jun. 15, 2022

(65) Prior Publication Data

US 2022/0315937 A1 Oct. 6, 2022

Related U.S. Application Data

(62) Division of application No. 16/646,001, filed as application No. PCT/US2018/050613 on Sep. 12, 2018, now Pat. No. 11,390,874.

(60) Provisional application No. 62/666,923, filed on May 4, 2018, provisional application No. 62/560,026, filed on Sep. 18, 2017.

(51) Int. Cl.
*C12N 15/81* (2006.01)
*C12N 15/90* (2006.01)

(52) U.S. Cl.
CPC ......... *C12N 15/815* (2013.01); *C12N 15/905* (2013.01)

(58) Field of Classification Search
None
See application file for complete search history.

(56) References Cited

U.S. PATENT DOCUMENTS

| | | | |
|---|---|---|---|
| 8,685,402 B2 * | 4/2014 | Lanzavecchia | C07K 16/1018 536/23.53 |
| 8,685,737 B2 | 4/2014 | Serber et al. | |
| 9,476,065 B2 | 10/2016 | Horwitz et al. | |
| 11,390,874 B2 | 7/2022 | Jiang | |
| 11,685,934 B2 | 6/2023 | Walter | |
| 11,884,928 B2 | 1/2024 | Tsegaye | |
| 2015/0225733 A1 | 8/2015 | Kim et al. | |
| 2020/0263188 A1 | 8/2020 | Tsegaye | |
| 2020/0263205 A1 | 8/2020 | Walter | |
| 2022/0315937 A1 | 10/2022 | Jiang | |

FOREIGN PATENT DOCUMENTS

| | | |
|---|---|---|
| CN | 106029886 A | 10/2016 |
| WO | 2012149470 A1 | 11/2012 |
| WO | 2012176981 A1 | 12/2012 |
| WO | 2015095804 A1 | 6/2015 |
| WO | 2015138855 A1 | 9/2015 |
| WO | 2016110512 A1 | 7/2016 |

OTHER PUBLICATIONS

Barnard et al. (J. Ind. Microbiol. Biotechnol. Vol 37, pp. 961-971, 2010).*
U.S. Appl. No. 16/646,001, "Non-Final Office Action", Oct. 25, 2021, 23 pages.
U.S. Appl. No. 16/646,001, "Notice of Allowance", Apr. 6, 2022, 13 pages.
U.S. Appl. No. 16/646,013, "Non-Final Office Action", Nov. 2, 2022, 9 pages.
U.S. Appl. No. 16/646,013, "Notice Of Allowance", Aug. 23, 2023, 9 pages.
U.S. Appl. No. 16/646,013, "Notice of Allowance", May 9, 2023, 10 pages.
U.S. Appl. No. 16/646,028, "Corrected Notice of Allowability", Apr. 26, 2023, 2 pages.
U.S. Appl. No. 16/646,028, "Non-Final Office Action", Jul. 11, 2022, 21 pages.
U.S. Appl. No. 16/646,028, "Notice of Allowance", Feb. 21, 2023, 7 pages.
U.S. Appl. No. 16/646,028, "Notice of Allowance", Oct. 28, 2022, 8 pages.
U.S. Appl. No. 17/841,429, "U.S. Divisional Patent Application No.", Methods for Genomic Integration in Pichia and Other Host Cells, Jun. 15, 2022, 45 pages.
Abdel-Banat, et al., "Random and Targeted Gene Integrations Through the Control of Non-homologous End Joining in The Yeast *Kluyveromyces marxianus*", Yeast, vol. 27, No. 1, Jan. 2010, pp. 29-39.
Chen, et al., "A Gene-Cloning System for *Kluyveromyces lactis* and Isolation of a Chromosomal Gene Required for Killer Toxin Production", Journal of Basic Microbiology, vol. 28, No. 4, Jan. 1, 1988, pp. 211-220.
Dicarlo, et al., "Genome Engineering in *Saccharomyces cerevisiae* Using CRISPR-Cas Systems", Nucleic Acids Research, vol. 41, No. 7, Mar. 4, 2013, pp. 4336-4343.
Dicarlo, et al., "Supplemental Data to Genome engineering in *Saccharomyces cerevisiae* using CRISPR-Cas systems", Nucleic Acids Research, vol. 41, No. 7, Mar. 4, 2013, pp. 1-5.
Heus, et al., "Chromatin Structures of *Kluyveromyces lactis* Centromeres in K.Lactis and *Saccharomyces Cerevisiae*", Chromosoma, vol. 102, No. 9, Nov. 1993, pp. 660-667.
Horwitz, et al., "Efficient Multiplexed Integration of Synergistic Alleles and Metabolic Pathways in Yeasts via CRISPR-Cas", Cell Systems, vol. 1, Jul. 29, 2015, 9 pages.
Hoshida, et al., "Non-Homologous End Joining-Mediated Functional Marker Selection for DNA Cloning in the Yeast *Kluyveromyces marxianus*", Yeast, vol. 31, No. 1, Jan. 2014, pp. 29-46.
Iborra, et al., "*Kluyveromyces marxianus* Small DNA Fragments Contain Both Autonomous Replicative and Centromeric Elements that also Function in *Kluyveromyces lactis*", Yeast, vol. 10, No. 12, Dec. 1994, pp. 1621-1629.

(Continued)

*Primary Examiner* — Richard G Hutson
(74) *Attorney, Agent, or Firm* — Kilpatrick Townsend & Stockton LLP

(57) ABSTRACT

The present invention provides high efficiency targeted and marker-less single, double, triple, quadruple, and quintuple integrations by using CRISPR in host cells, including *Pichia*.

19 Claims, 2 Drawing Sheets

Specification includes a Sequence Listing.

(56) References Cited

OTHER PUBLICATIONS

Krijger, et al., "A Novel, Lactase-Based Selection and Strain Improvement Strategy for Recombinant Protein Expression in *Kluyveromyces lactis*", Microbial Cell Factories, vol. 11, No. 1, Aug. 20, 2012, pp. 1-12.
Krijger, et al., "A Novel, Lactase-based Selection and Strain Improvement Strategy for Recombinant Protein Expression in *Kluyveromyces lactis*", Microbial Cell Factories, vol. 11, Dec. 31, 2012, pp. 1-12.
Liachko, et al., "An Autonomously Replicating Sequence for Use in a Wide Range of Budding Yeasts", FEMS Yeast Research, vol. 14, No. 2, Dec. 2, 2014, pp. 364-367.
Lobs, et al., "CRISPR-Cas9-Enabled Genetic Disruptions for Understanding Ethanol and Ethyl Acetate Biosynthesis in *Kluyveromyces marxianus*", Biotechnology for Biofuels, vol. 10, No. 164, Jun. 24, 2017, 14 pages.
PCT/US2018/050613, "International Preliminary Report on Patentability", Apr. 2, 2020, 9 pages.
PCT/US2018/050635, "International Preliminary Report on Patentability", Apr. 2, 2020, 8 pages.
PCT/US2018/050635, "International Search Report and Written Opinion", Jan. 4, 2019, 13 pages.
PCT/US2018/050732, "International Preliminary Report on Patentability", Apr. 2, 2020, 9 pages.
PCT/US2018/050732, "International Search Report and Written Opinion", Nov. 8, 2019, 15 pages.
Walter, et al., "CRISPR-Cas-Assisted Multiplexing (CAM): Simple Same-Day Multi-Locus Engineering in Yeast", Journal of Cellular Physiology, vol. 231, No. 12, Dec. 1, 2016, pp. 2563-2569.
International Search Report and Written Opinion in PCT Application PCT/US2018/050613 mailed Jan. 4, 2019; 14 pages.
Gao, S. et al.; "Multiplex gene editing of the *Yarrowia lipolytica* genome using the CRISPR-Cas9 system"; *Journal of Industrial Microbiology and Biotechnology*; vol. 43, No. 8; Jun. 27, 2016; pp. 1085-1093.
Goncalves, A.M., et al.; "*Pichia pastoris*: A Recombinant Microfactory for Antibodies and Human Membrane Proteins"; *Journal of Microbiology and Biotechnology*; vol. 23, No. 5; May 1, 2013; pp. 587-601.
Horwitz, A.A. et al.; "Efficient Multiplexed Integration of Synergistic Alleles and Metabolic Pathways in Yeasts via CRISPR-Cas"; *Cell Systems*; vol. 1, No. 1; Jul. 1, 2015; pp. 88-96.
Naatsaari, L. et al.; "Deletion of the *Pichia pastoris* KU70 Homologue Facilitates Platform Straing Generation for Gene Expression and Synthetic Biology"; *PLOS One*; Jul. 29, 2012; 14 pages.
Vogl, T. et al.; "New opportunities by synthetic biology for biopharmaceutical production in *Pichia pastoris*"; *Current Opinion in Biotechnology*; vol. 24, No. 6; Dec. 24, 2013; pp. 1094-1101.
Weninger, A. et al.; "Combinatorial optimization of CRISPR/Cas9 expression enables precision genome engineering in the methylotrophic yeast *Pichia pastoris*"; *Journal of Biotechnology*; vol. 235; Mar. 22, 2016; pp. 139-149.
Arruda, A et al.; "A constitutive expression sytem for *Pichia pastoris* based on the PGK1 promoter"; *Biotechnol. Lett.*; vol. 38; 2016; pp. 509-517.
Cho, et al.; *ACS Synthetic Biology*; vol. 7; Mar. 15, 2018; pp. 1085-1094.
Chakraborty, S.; Prime-editors (nickases), hRad51-Cas9 nickase fusions and dCas9 have the same problem as conventional CRISPR-Cas9 of plasmid/Cas9 integration after making a double stranded break; retrieved from the internet at https://doi.org/10.31219/osf.io/jt6pe; Dec. 1, 2019.

\* cited by examiner

SEQUENCE LISTING

<160> NUMBER OF SEQ ID NOS: 67

<210> SEQ ID NO 1
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
aaagctagag ttaccgtaa                                              19

<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
tcaactgcag tcttgataa                                                19

<210> SEQ ID NO 3
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
gtgtgaacag agccatgta                                                19

<210> SEQ ID NO 4
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
atttggagat tttgcgcta                                                19

<210> SEQ ID NO 5
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ttctggagag cactatgac                                                19

<210> SEQ ID NO 6
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
aaccctaaga atctggctc                                                19

<210> SEQ ID NO 7
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
tcaacaagta cttatatga                                                19

<210> SEQ ID NO 8
<211> LENGTH: 19
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 8
attttatgtc tcagcaaga                                               19

<210> SEQ ID NO 9
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
gacatggctc ctatggttt                                               19

<210> SEQ ID NO 10
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tggctgaaat taggtaaag                                               19

<210> SEQ ID NO 11
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
agaaaataaa gagtttcta                                               19

<210> SEQ ID NO 12
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
tagatgcagt aggataggg                                               19

<210> SEQ ID NO 13
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gtccactaac tacctttcg                                               19
```

```
<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14 aaagatagggaaaaggaaa                                                    19

<210> SEQ ID NO 15
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15 tcagat                                                                  6

<210> SEQ ID NO 16
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
cgcgaatgtt cccccagctt atctcgacag gtggcacttt tcggggaaat gtgcg           55

<210> SEQ ID NO 17
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
gaccaaaata agtaaatatt aattgtcgaa tactttctag agaataggaa cttcgg          56

<210> SEQ ID NO 18
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
cgcacatttc cccgaaaagt gccacctgtc gagataagct gggggaacat tcgcg           55

<210> SEQ ID NO 19
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 19
ccgaagttcc tattctctag aaagtattcg acaattaata tttacttatt ttggtc        56

<210> SEQ ID NO 20
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
aaaatcataa atcataagaa attcgcgtcc cattcgccat gccgaagcat gttgcc        56

<210> SEQ ID NO 21
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ggcaacatgc ttcggcatgg cgaatgggac gcgaatttct tatgatttat gatttt        56

<210> SEQ ID NO 22
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ctagaactag tggatccccc gggcgctgga gttagcatat ctacaattgg gtg           53

<210> SEQ ID NO 23
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
gggaggactc tcgtttccta tg                                             22

<210> SEQ ID NO 24
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
ttttagagct agaaatagca ag                                             22

<210> SEQ ID NO 25
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 25
cccctcgagg tcgacggtat c                                              21

<210> SEQ ID NO 26
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
tcttgctgag acataaaatc atctgagacg agcttactcg tttcgtcctc ac            52

<210> SEQ ID NO 27
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
attttatgtc tcagcaagag ttttagagct agaaatagca agttaaaata ag            52

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ctagaactag tggatccccc g                                              21

<210> SEQ ID NO 29
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
cgctcgtcca acgccggcgg acct                                           24

<210> SEQ ID NO 30
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
taacagttat tattcgagat cta                                            23
```

```
<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
ggtaccatac ttctccaccg                                                   20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
ttcgaaactg cagctagcaa                                                   20

<210> SEQ ID NO 33
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
ccattgttgc cgataactgt tg                                                22

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
cggtatcgct gctttcttta                                                   20

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
caataatcaa tgcagcccca g                                                 21

<210> SEQ ID NO 36
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 36
gaaaagggta gtgaaaggaa ag                                           22

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
gctaattacg taccagaacc                                              20

<210> SEQ ID NO 38
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
ttgacacctt ggataaaagg g                                            21

<210> SEQ ID NO 39
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
cagaataact tcatgactgc                                              20

<210> SEQ ID NO 40
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
agtgacgcca acaatacccca tga                                         23

<210> SEQ ID NO 41
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
ttgtcccact ttgaataatc g                                            21

<210> SEQ ID NO 42
<211> LENGTH: 24
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
ggagtttttt gggctagggg tttg                                          24

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
gctgagcact tcagtcttac g                                             21

<210> SEQ ID NO 44
<211> LENGTH: 164
<212> TYPE: DNA
<213> ORGANISM: Komagataella pastoris

<400> SEQUENCE: 44
tcgagataag ctgggggaac attcgcgaaa atgaaacaag tcggctgtta tagtatattt    60
attataatat tgaaagatct caaaagacta cttattttg aatgaaccaa gtatgaaatc    120
aacctatttg gggttgacca aaataagtaa atattaattg tcga                    164

<210> SEQ ID NO 45
<211> LENGTH: 550
<212> TYPE: DNA
<213> ORGANISM: Komagataella pastoris

<400> SEQUENCE: 45
tgttgtagtt ttaatatagt ttgagtatga gatggaactc agaacgaagg aattatcacc    60
agtttatata ttctgaggaa agggtgtgtc ctaaattgga cagtcacgat ggcaataaac   120
gctcagccaa tcagaatgca ggagccataa attgttgtat tattgctgca agatttatgt   180
gggttcacat tccactgaat ggttttcact gtagaattgg tgtcctagtt gttatgtttc   240
gagatgtttt caagaaaaac taaaatgcac aaactgacca ataatgtgcc gtcgcgcttg   300
gtacaaacgt caggattgcc accactttt tcgcactctg gtacaaaagt tcgcacttcc   360
cactcgtatg taacgaaaaa cagagcagtc tatccagaac gagacaaatt agcgcgtact   420
gtcccattcc ataaggtatc ataggaaacg agagtcctcc ccccatcacg tatatataaa   480
cacactgata tcccacatcc gcttgtcacc aaactaatac atccagttca agttacctaa   540
acaaatcaaa                                                          550

<210> SEQ ID NO 46
<211> LENGTH: 550
<212> TYPE: DNA
<213> ORGANISM: Unknown
<220> FEATURE:
<221> NAME/KEY: source
<223> OTHER INFORMATION: /note="Description of Unknown:
      Hammerhead sequence"

<400> SEQUENCE: 46
tgttgtagtt ttaatatagt ttgagtatga gatggaactc agaacgaagg aattatcacc    60
```

```
agtttatata ttctgaggaa agggtgtgtc ctaaattgga cagtcacgat ggcaataaac    120
gctcagccaa tcagaatgca ggagccataa attgttgtat tattgctgca agatttatgt    180
gggttcacat tccactgaat ggttttcact gtagaattgg tgtcctagtt gttatgtttc    240
gagatgtttt caagaaaaac taaaatgcac aaactgacca ataatgtgcc gtcgcgcttg    300
gtacaaacgt caggattgcc accactttt tcgcactctg gtacaaaagt tcgcacttcc    360
cactcgtatg taacgaaaaa cagagcagtc tatccagaac gagacaaatt agcgcgtact    420
gtcccattcc ataaggtatc ataggaaacg agagtcctcc ccccatcacg tatatataaa    480
cacactgata tcccacatcc gcttgtcacc aaactaatac atccagttca agttacctaa    540
acaaatcaaa                                                           550

<210> SEQ ID NO 47
<211> LENGTH: 68
<212> TYPE: DNA
<213> ORGANISM: Hepatitis delta virus

<400> SEQUENCE: 47
ggccggcatg gtcccagcct cctcgctggc gccggctggg caacatgctt cggcatggcg    60
aatgggac                                                             68

<210> SEQ ID NO 48
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48 atctga                                                                6

<210> SEQ ID NO 49
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
ttttagagct agaaatagca agttaaaata aggctagtcc gttatcaact tgaaaaagtg    60
gcaccgagtc ggtggtgc                                                  78

<210> SEQ ID NO 50
<211> LENGTH: 253
<212> TYPE: DNA
<213> ORGANISM: Saccharomyces cerevisiae

<400> SEQUENCE: 50
gcgaatttct tatgatttat gatttttatt attaaataag ttataaaaaa aataagtgta    60
tacaaatttt aaagtgactc ttaggtttta aaacgaaaat tcttattctt gagtaactct    120
ttcctgtagg tcaggttgct ttctcaggta tagcatgagg tcgctcttat tgaccacacc    180
tctaccggca tgccgagcaa atgcctgcaa atcgctcccc atttcacccca attgtagata    240 tgctaactcc agc                                                       253
```

<210> SEQ ID NO 51
<211> LENGTH: 1019
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51

```
tgttgtagtt ttaatatagt ttgagtatga gatggaactc agaacgaagg aattatcacc      60
agtttatata ttctgaggaa agggtgtgtc ctaaattgga cagtcacgat ggcaataaac     120
gctcagccaa tcagaatgca ggagccataa attgttgtat tattgctgca agatttatgt     180
gggttcacat tccactgaat ggttttcact gtagaattgg tgtcctagtt gttatgtttc     240
gagatgtttt caagaaaaac taaaatgcac aaactgacca ataatgtgcc gtcgcgcttg     300
gtacaaacgt caggattgcc accacttttt tcgcactctg gtacaaaagt tcgcacttcc     360
cactcgtatg taacgaaaaa cagagcagtc tatccagaac gagacaaatt agcgcgtact     420
gtcccattcc ataaggtatc ataggaaacg agagtcctcc ccccatcacg tatatataaa     480
cacactgata tcccacatcc gcttgtcacc aaactaatac atccagttca agttacctaa     540
acaaatcaaa atctgactga tgagtccgtg aggacgaaac gagtaagctc gtctcagatg     600
gatttgatca atgaaagctg ttttagagct agaaatagca agttaaaata aggctagtcc     660
gttatcaact tgaaaaagtg gcaccgagtc ggtggtgcgg ccggcatggt cccagcctcc     720
tcgctggcgc cggctgggca acatgcttcg gcatggcgaa tgggacgcga atttcttatg     780
atttatgatt tttattatta aataagttat aaaaaaaata agtgtataca aattttaaag     840
tgactcttag gttttaaaac gaaaattctt attcttgagt aactctttcc tgtaggtcag     900
gttgctttct caggtatagc atgaggtcgc tcttattgac cacacctcta ccggcatgcc     960
gagcaaatgc ctgcaaatcg ctccccattt cacccaattg tagatatgct aactccagc    1019
```

<210> SEQ ID NO 52
<211> LENGTH: 834
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

```
cccctcgagg tcgacggtat cgattgttgt agttttaata tagtttgagt atgagatgga      60
actcagaacg aaggaattat caccagttta tatattctga ggaaagggtg tgtcctaaat     120
tggacagtca cgatggcaat aaacgctcag ccaatcagaa tgcaggagcc ataaattgtt     180
gtattattgc tgcaagattt atgtgggttc acattccact gaatggtttt cactgtagaa     240
ttggtgtcct agttgttatg tttcgagatg ttttcaagaa aaactaaaat gcacaaactg     300
accaataatg tgccgtcgcg cttggtacaa acgtcaggat tgccaccact tttttcgcac     360
tctggtacaa aagttcgcac ttcccactcg tatgtaacga aaaacagagc agtctatcca     420
gaacgagaca aattagcgcg tactgtccca ttccataagg tatcatagga aacgagagtc     480
ctcccccat cacgtatata taaacacact gatatcccac atccgcttgt caccaaacta     540
atacatccca ttcaagttac ctaaacaaat caaaatctga ctgatgagtc cgtgaggacg     600
aaacgagtaa gctcgtctca gatggatttg atcaatgaaa gctgttttag agctagaaat     660
```

| | | |
|---|---|---|
| agcaagttaa aataaggcta gtccgttatc aacttgaaaa agtggcaccg agtcggtggt | 720 |
| gcggccggca tggtcccagc ctcctcgctg gcgccggctg ggcaacatgc ttcggcatgg | 780 |
| cgaatgggac ttttttttgtt ttttatgtct gcccggggga tccactagtt ctag | 834 |

<210> SEQ ID NO 53
<211> LENGTH: 1825
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53

| | |
|---|---|
| gacggcacgg ccacgcgttt aaaccgccaa gatggtgatt tccagcgttc gaaaagcctg | 60 |
| tagtacccag aattttgatc aaagtgtcct cttagccgtg gcatccgcgg ctgtcatctt | 120 |
| gatccttctt cgcatgagca cttacgtgat gctgataaga tgggcacgcc acaacactag | 180 |
| ggccaagacc tcgcctagtg gtggcgacta tctaaagggc tcacctaaca cctctttagc | 240 |
| ggggattgaa gacattcata cacgaagtct gctgtatggg tcagacgaga aaatgccgca | 300 |
| atctaaagaa gaacaaaggt cccacaatgc gaatcgtgat ggtgataaat cattggctca | 360 |
| ggtcagtaga tttgaaatgc atgataaacg catatggtga gagccgttct gcacaactag | 420 |
| atgttttcga gcttcgcatt gtttcctgca gctcgactat tgaattaaga tttccggata | 480 |
| tctccaatct cacaaaaact tatgttgacc acgtgctttc ctgaggcgag gtgttttata | 540 |
| tgcaagctgc caaaaatgga aaacgaatgg ccatttttcg cccaggcaaa ttattcgatt | 600 |
| actgctgtca taaagacagt gttgcaaggc tcacattttt ttttaggatc cgagataaag | 660 |
| tgaatacagg acagcttatc tctatatctt gtaccattcg tgaatcttaa gagttcggtt | 720 |
| aggggggactc tagttgaggg ttggcactca cgtatggctg ggcgcagaaa taaaattcag | 780 |
| gcgcagcagc acttatcgat gcatgcaagg cgagaaaaat aaagaacaaa aacacacctt | 840 |
| gctaagacca caacctttca aattttgaga ttgttattct ttcatcctaa aacaccaccg | 900 |
| tcctatctct tgggaacgta catatcattg agcttggttc attgatacat cactgtatct | 960 |
| aactctcctt tttcgctcgt ccaacgccgg cggacctcaa aaaggatcta aaaataagac | 1020 |
| agtagtggac ttatattcat accatatgat gggtgtttgc tcactcgtat ggatcaaaat | 1080 |
| tccatggttt cttctgtaca acttgtacac ttatttggac ttttctaacg gttttctgg | 1140 |
| tgatttgaga agtccttatt ttggtgttcg cagcttatcc gtgattgaac catcagaaat | 1200 |
| actgcagctc gttatctagt ttcagaatgt gttgtagaat acaatcaatt ctgagtctag | 1260 |
| tttgggtggg tcttggcgac gggaccgtta tatgcatcta tgcagtgtta aggtacatag | 1320 |
| aatgaaaatg taggggttaa tcgaaagcat cgttaatttc agtagaacgt agttctattc | 1380 |
| cctacccaaa taatttgcca agaatgcttc gtatccacat acgcagtgga cgtagcaaat | 1440 |
| ttcactttgg actgtgacct caagtcgtta tcttctactt ggacattgat ggtcattacg | 1500 |
| taatccacaa agaattggat agcctctcgt tttatctagt gcacagccta atagcactta | 1560 |
| agtaagagca atggacaaat ttgcatagac attgagctag atacgtaact cagatcttgt | 1620 |
| tcactcatgg tgtactcgaa gtactgctgg aaccgttacc tcttatcatt tcgctactgg | 1680 |
| ctcgtgaaac tactgatga aaaaaaaaaa gagctgaaag cgagatcatc ccatttttgtc | 1740 |
| atcatacaaa ttcacgcttg cagttttgct tcgttaacaa gacaagatgt ctttatccgg | 1800 |

```
tgtttaaacc ccagcgcctg gcggg                                         1825
```

<210> SEQ ID NO 54
<211> LENGTH: 1865
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

```
gacggcacgg ccacgcgttt aaaccgccgc agggtcccac acagaccaaa tccaagttat      60
tccctaaggg atggttttca gagagagaag aaactataat ggtaaaccgg ttgttgcggg     120
atgacccctc taagagtgat atgcacaata gacagtctgt tacgccaaaa gaactgtgga     180
aagtgttggg agactacgat ctatggccta tatacgcatt ggccatggta ttttccattc     240
cccagatacc gataaagaga taccttactc ttactttgag ggcattagag ttcactacca     300
ctgagatcaa tctcttaaca atccctgctt cgtttctggc gggaatcatg tcaattgcta     360
tttcattagt cagtgagttc ttcaatgaag gtttgattat cggtatattg tgtcaattct     420
ggttgcttat tatggttatc attgaataca cctctgtgga aaagatatct ccctggggac     480
aatatgtgtt gcaactgttc gttgttggtg ccccagtccc ccaaccggta ctaatcggtc     540
tatgttcccg taactcatat tcggttagaa ctagaacaat aagtgcatca ttgttcaaca     600
ttgtggttca attgtcgaac attgctggtg cttatatcta cagggaagac gataagcctt     660
tgtacaagag aggtaacaga cagttaattg gtatttcttt gggagtcgtt gccctctacg     720
ttgtctccaa gacatactac attctgagaa acagatggaa gactcaaaaa tgggagaagc     780
ttagtgaaga agagaaagtt gcctacttgg acagagctga aaggagaac ctgggttcta     840
agaggctgga cttttgttc gagagttaaa ctgcataatt ttttctaagt aaatttcata     900
gttatgaaat ttctgcagct tagtgtttac tgcatcgttt actgcatcac cctgtaaata     960
atgtgagctt ttttccttcc attgcttggt atcttccttg ctgctgtttc gctcgtccaa    1020
cgccggcgga cctgagacgg aaaacggaga aggagaacg gagaacgaag aacgaaggga    1080
gagagaagca aagggaagag caaggtattc tggagagatt aagaaaatag tagaatagat    1140
ttaacgaaac tgaaactgaa agaccgaaaa agaatgcag aaattaaaca ccatagggca    1200
gattgattcc gtaatcggtt tcttgctact atatctttct aggctgtcta taatccttt    1260
ataatttaat ctgctaatat cgctgtcacg attattgaca tcgactgtat ttcaacacac    1320
aggtcttaca gatagcatgg ggtttccagt atttgattga catttccgtt tttgcatagt    1380
ccataatata aggatcaaaa acatgagatg tcgcaaggcc tcttaaacat gaaatctccg    1440
tttaccttcc gccatacaac cttacgcata cagcagctcg gtttctacat agagtctttt    1500
caagaaccgg ggtaaaaacc gttttacata gaaagaggta aaacgttgtg atcatgtgac    1560
cgctgaacat ctccggaacc aacacttcgc gatcttttt cgtctgtcac atactcaagg    1620
taaactaagt ttcacaacac gaaggctccg tatcataaat cctcagagtt gaagcactgg    1680
cccccatcta ataaatactc cgaaatgagt caaatccagt caagccaagt ggggcgaaa    1740
aatatgcaaa ccgcacagcc tcaggctcaa caaagaccaa tcaatgggtc tgtgaccctg    1800
agcaatggcc agaggataaa ccctcagaac ttgactccgg tgtttaaacc ccagcgcctg    1860
gcggg                                                                1865
```

<210> SEQ ID NO 55
<211> LENGTH: 1928
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55

| | | | | | |
|---|---|---|---|---|---|
| gacggcacgg | ccacgcgttt | aaaccgcccg | ttctgatggc | ttgatgaccg | ttgtattgcc | 60 |
| tgtcactata | gccaggggta | gggtccataa | aggaatcata | gcagggaaat | aaaagggca | 120 |
| tattgatgca | atcactccca | atggctctct | tgccattgaa | gtctccatat | cagcactaac | 180 |
| ttccaagaag | gaccccttca | agtctgacgt | gatagagcac | gcttgctctg | ccacctgtag | 240 |
| tcctctcaaa | acgtcacctt | gtgcatcagc | aaagacttta | ccttgctcca | atactatgac | 300 |
| ggaggcaatt | ctgtcaaaat | tctctctcag | caattcaacc | aacttgaaag | caaattgctg | 360 |
| tctcttgatg | atggagactt | ttttccaaga | ttgaaatgca | atgtgggacg | actcaattgc | 420 |
| ttcttccagc | tcctcttcgg | ttgattgagg | aacttttgaa | accacaaaat | tggtcgttgg | 480 |
| gtcatgtaca | tcaaaccatt | ctgtagattt | agattcgacg | aaagcgttgt | tgatgaagga | 540 |
| aaaggttgga | tacggtttgt | cggtctcttt | ggtatggccg | gtggggtatg | caattgcagt | 600 |
| agaagataat | tggacagcca | ttgttgaagg | tagagaaaag | gtcagggaac | ttggggtta | 660 |
| tttataccat | tttaccccac | aaataacaac | tgaaaagtac | ccattccata | gtgagaggta | 720 |
| accgacggaa | aaagacgggc | ccatgttctg | ggaccaatag | aactgtgtaa | tccattggga | 780 |
| ctaatcaaca | gacgattggc | aatataatga | aatagttcgt | tgaaaagcca | cgtcagctgt | 840 |
| cttttcatta | actttggtcg | gacacaacat | tttctactgt | tgtatctgtc | ctactttgct | 900 |
| tatcatctgc | cacagggcaa | gtggatttcc | ttctcgcgcg | gctgggtgaa | aacggttaac | 960 |
| gtgaacgctc | gtccaacgcc | ggcggacctg | ccttgggga | cttcaagtct | ttgctagaaa | 1020 |
| ctagatgagg | tcaggccctc | ttatggttgt | gtcccaattg | ggcaatttca | ctcacctaaa | 1080 |
| aagcatgaca | attatttagc | gaaataggta | gtatattttc | cctcatctcc | caagcagttt | 1140 |
| cgttttgca | tccatatctc | tcaaatgagc | agctacgact | cattagaacc | agagtcaagt | 1200 |
| aggggtgagc | tcagtcatca | gccttcgttt | ctaaaacgat | tgagttcttt | tgttgctaca | 1260 |
| ggaagcgccc | tagggaactt | tcgcactttg | gaaatagatt | ttgatgacca | agagcggag | 1320 |
| ttgatattag | agaggctgtc | caaagtacat | gggatcaggc | cggccaaatt | gattggtgtg | 1380 |
| actaaaccat | tgtgtacttg | gacactctat | tacaaaagcg | aagatgattt | gaagtattac | 1440 |
| aagtcccgaa | gtgttagagg | attctatcga | gcccagaatg | aaatcatcaa | ccgttatcag | 1500 |
| cagattgata | aactcttgga | aagcggtatc | ccatttcat | tattgaagaa | ctacgataat | 1560 |
| gaagatgtga | gagacggcga | ccctctgaac | gtagacgaag | aaacaaatct | acttttgggg | 1620 |
| tacaatagag | aaagtgaatc | aagggaggta | tttgtggcca | taatactcaa | ctctatcatt | 1680 |
| aatgtggttc | ttttggtagc | aaaaatcttt | gttgttttgt | tcagttcctc | actctcattg | 1740 |
| atggcttcgt | tagttgactc | cgtgatggat | ttcttatcta | ctttgatcat | atatgtttct | 1800 |
| aactcttttg | ctgggaaaag | agacaagaat | gagtatccaa | ttggaaggtc | aaggttggag | 1860 |
| ccctaggag | ttcttgtctt | ttccgtaatc | ataattgtct | cggtgtttaa | accccagcgc | 1920 |
| ctggcggg | | | | | 1928 |

<210> SEQ ID NO 56

<211> LENGTH: 1963
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56

| | | | | |
|---|---|---|---|---|
| gacggcacgg | ccacgcgttt | aaaccgccaa | ggcatatagg cgagggagag ttagctagca | 60 |
| tacaagataa | tgaaggatca | atagcggtag | ttaaagtgca caagaaaaga gcacctgttg | 120 |
| aggctgatga | taaagctcca | attacattgc | cacagagaaa cacagtaaca gaaataggag | 180 |
| gggatgcacc | acgagaagag | cattcagtga | acaactttgc caaattcata accccaagcg | 240 |
| ctaataagcc | aatgtcaaag | tcggctacta | acattaatag tacaacaact atcgattttc | 300 |
| aaccagatgt | ttgcaaggac | tacaaacaga | caggttactg cggatatggt gacacttgta | 360 |
| agttttgca | cctgagggat | gatttcaaac | agggatggaa attagatagg gagtgggaaa | 420 |
| atgtccaaaa | gaagaagcat | aatactctca | aagggggttaa ggagatccaa atgtttaatg | 480 |
| aagatgagct | caaagatatc | ccgtttaaat | gcattatatg caaaggagat tacaaatcac | 540 |
| ccgtgaaaac | ttcttgcaat | cattattttt | gcgaacaatg tttcctgcaa cggtcaagaa | 600 |
| gaaaaccaaa | ttgtattata | tgtggcagag | acactttagg agttgcttta ccagcaaaga | 660 |
| agttgtccca | atttctggct | aagatacata | ataatgaaag taataaagtt tagtaattgc | 720 |
| attgcgttga | ctattgattg | cattgatgtc | gtgtgatact ttcaccgaaa aaaaacacga | 780 |
| agcgcaatag | gagcggttgc | atattagtcc | ccaaagctat ttaattgtgc ctgaaactgt | 840 |
| tttttaagct | catcaagcat | aattgtatgc | attgcgacgt aaccaacgtt taggcgcagt | 900 |
| ttaatcatag | cccactgcta | agccagaatt | ctaatatgta actacgtacc tttcctttta | 960 |
| ataaatgatc | tgtattttcc | acctagtagc | agatcaaatt gttcaacttt aagtctttgg | 1020 |
| tccctcaagc | gagagaactt | gcgcgctcgt | ccaacgccgg cggacctcgg aggaatgcaa | 1080 |
| ataataatct | ccttaattac | ccactgataa | gctcaagaga cgcggtttga aaacgatata | 1140 |
| atgaatcatt | tggattttat | aataaacct | gacagttttt ccactgtatt gttttaacac | 1200 |
| tcattggaag | ctgtattgat | tctaagaagc | tagaaatcaa tacggccata caaaagatga | 1260 |
| cattgaataa | gcaccggctt | ttttgattag | catataccct aaagcatgca ttcatggcta | 1320 |
| catagttgtt | aaagggcttc | ttccattatc | agtataatga attacataat catgcactta | 1380 |
| tatttgccca | tctctgttct | ctcactcttg | cctgggtata ttctatgaaa ttgcgtatag | 1440 |
| cgtgtctcca | gttgaacccc | aagcttggcg | agtttgaaga gaatgctaac cttgcgtatt | 1500 |
| ccttgcttca | ggaaacattc | aaggagaaac | aggtcaagaa gccaaacatt ttgatccttc | 1560 |
| ccgagttagc | attgactggc | tacaattttc | aaagccagca gcggatagag cctttttgg | 1620 |
| aggaaacaac | caagggagct | agtacccaat | gggctcaaaa agtatccaag acgtgggatt | 1680 |
| gctttacttt | aataggatac | ccagaaaaaa | gtttagagag ccctcccgt atttacaaca | 1740 |
| gtgcggtact | tgtatcgcct | cagggaaaag | taatgaacaa ctacagaaag tccttcttgt | 1800 |
| atgaagctga | tgaacattgg | ggatgttcgg | aatcttctga tgggtttcaa acagtagatt | 1860 |
| tattaattga | aggaaagact | gtaaagacat | catttggaat ttgcatggat ttgaatcctt | 1920 |
| ataaatttga | agctccggtg | tttaaaccc | agcgcctggc ggg | 1963 |

<210> SEQ ID NO 57
<211> LENGTH: 1908

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

```
gacggcacgg ccacgcgttt aaaccgccct gtggactcag gaccagctca gcttgacaaa      60
ccaagacttg cactccaatg tgcacaaccc agtgattgag cagatcgaaa cctcatcagg     120
agtcagattg tagtatggaa actttgtat tctctatgta cttaaacact ggtttatttt      180
tttattgatc gttatattga acagtttaca ctggaacatc ttcagggtcg atgtccttaa     240
tccagtgttg accaaagatt gggatcttct cgaagaaagt cttttggaac aaaggccagt    300
tttcagtgaa agtgaagacg gcaaacagac cggcacctcc ccagaaagcc aaaattggaa     360
aagtagtttt aatttgggtt ggagtcaatc cagcaatttt cttgacggtg gtatacttgg     420
gacctttaac gtactgaaat gttagaacat gtttgtaaaa atcaaatcat cactgcagaa     480
acggtttgtg tgcctgcacc ggagggttat cataatgcca cttacgttga ccattttgga    540
ggtgtttgac taagttcaaa tatgaatctc taagaaaact aataatcaat atggtgcgag     600
cattgattgg ttggacagct agtttggaga agtacacgac ttagatgaat ctgcaataag    660
gaatagtcca atctgattat gtaagctctc cttttggtt ttcatttcca tcagctcaag    720
cttatcatag ctcaggtccc ctccagctta tgatggaata ggccattatt ttttgcccta   780
aaaagtggaa gtccacaaga agaaatacaa atactcaaaa ttcaaaagtc ttcctttgag   840
tggatgcaat tttacgtagt ttactgtatg acgtaactaa tgaacccttc cgacacaaag   900
attgaggtgc ctcacttaac gtcattcttc tatcccacg agtgcaactg actaggtctt    960
atttttgttaa ttgcctcagt ttctccgaac gctcgtccaa cgccggcgga ccttttatgca 1020
tatactgaaa caacagaagg aactacagta aattcataaa aagcttaatt cttactttca  1080
tctcggcact gtaaattaac tcaagttggg gcaacattgt gtgtatactc ttactggcat  1140
cttttcatct gaagtcatct tctactactc ttctcttctg tatgacgtaa tcagctcggc  1200
agctgtggca tcgaacaaaa aaatgaacag ccatccgtca tatctcatga ctgactgagc  1260
aagaactaag tcaacaggaa acctaaaata agctttccat ttcttttgcg ctgaagccaa   1320
ccactcccca cacagttgat gagtggacgc aaaaccagct cctataccct tgacagaagag 1380
tcgccggaat caacctcaac aattcaggat atacgagagg aagaccaagt tgctccaggg   1440
ccccagcaag aagcacctaa acagtcacat atccaaaaat ggttaagcga tcatcctaaa  1500
gtatacgcag ttttatcttg gatatggaaa ttttggttga aacagtggtt tctcatatgt   1560
ttgggccctg cggttgctct agctcatgca tacccaaatt ttgccagaca tgatggaacc   1620
attaggtcag agtatactat caactacgga gccgtagcta tcatattctt catctctggt   1680
cttactatga aaccaaaga cttttttgaag aactttggac actggagagc ccatttcaca   1740
gtgttaagct gctcgtttct acttacttct tctatcattt acggtatagc gtgcggtata   1800
agagctgctc atgattccaa tatcgatgac tggatgttag caggacttat tgttaccgca   1860
tgttgtccaa ccactgtgag cggtgtttaa accccagcgc ctggcggg                 1908
```

<210> SEQ ID NO 58
<211> LENGTH: 1941
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 58

```
gacggcacgg ccacgcgttt aaaccgccgg aggaggtgga accacctgtg caggcggtct      60
gaaagtgttc aagtacggat ctactaccaa atatacatct ggtaacctga acggcgtcag     120
gttagtatac tggaacgaag gaaagttgca aagctccaaa tttgtggttc gatcctctaa     180
ttactctcaa aagcttggag gaaacagcaa cgccgaatca attgacaaca atggtgtggg     240
ttttgcctca gctggagact caggcgcatg gattctttcc aagctacaag atgttaggga     300
gtaccagtca ttcactgaaa agctaggtga agctacgatg agcattttcg atttccacgg     360
tcttaaacag gagacttcta ctacagggct tggggtagtt ggtatgattc attcttacga     420
cggtgagttc aaacagtttg gtttgttcac tccaatgaca tctattctac aaagacttca     480
acgagtgacc aatgtagaat ggtgtgtagc gggttgcgaa gatggggatg tggacactga     540
aggagaacac gaattgagtg atttggaaca actgcatatg catagtgatt ccgactagtc     600
aggcaagaga gagccctcaa atttacctct ctgcccctcc tcactccttt tggtacgcat     660
aattgcagta taaagaactt gctgccagcc agtaatctta tttcatacgc agttctatat     720
agcacataat cttgcttgta tgtatgaaat ttaccgcgtt ttagttgaaa ttgtttatgt     780
tgtgtgcctt gcatgaaatc tctcgttagc cctatcctta catttaactg gtctcaaaac     840
ctctaccaat tccattgctg tacaacaata tgaggcggca ttactgtagg gttggaaaaa     900
aattgtcatt ccagctagag atcacacgac ttcatcacgc ttattgctcc tcattgctaa     960
atcatttact cttgacttcg acccagaaaa gttcgcccgc tcgtccaacg ccggcggacc    1020
tatagttgtt ttttctatat aaaacgaaac gttatcatct ttaataatca ttgaggttta    1080
cccttatagt tccgtatttt cgtttccaaa cttagtaatc ttttggaaat atcatcaaag    1140
ctggtgccaa tcttcttgtt tgaagtttca aactgctcca ccaagctact agagactgt    1200
tctaggtctg aagcaacttc gaacacagag acagctgccg ccgattgttc ttttttgtgt    1260
ttttcttctg gaagaggggc atcatcttgt atgtccaatg cccgtatcct ttctgagttg    1320
tccgacacat tgtccttcga agagtttcct gacattgggc ttcttctatc cgtgtattaa    1380
ttttgggtta agttcctcgt ttgcatagca gtggatacct cgatttttt ggctcctatt    1440
tacctgacat aatattctac tataatccaa cttggacgcg tcatctatga taactaggct    1500
ctcctttgtt caaggggac gtcttcataa tccactggca cgaagtaagt ctgcaacgag    1560
gcggcttttg caacagaacg atagtgtcgt ttcgtacttg gactatgcta aacaaaagga    1620
tctgtcaaac atttcaaccg tgtttcaagg cactctttac gaattatcga ccaagacctt    1680
cctagacgaa catttcaaca tatccaggct actgcttcaa ggtggtgcaa atgataaagg    1740
tatagatatt agatgtgttt gggacctaaa acagttcttg cctgaagatt cccttgagca    1800
acaggcttca atagccaagt tagagaagca gtaccaaatc ggtaacaaaa ggggaagca    1860
tataaaacct ttactattgc gacaaaatcc atccttgaaa gtaaagctgt tgcggtgtt    1920
taaaccccag cgcctggcgg g                                              1941
```

<210> SEQ ID NO 59
<211> LENGTH: 1940
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 59

| | | | | | |
|---|---|---|---|---|---|
| gacggcacgg | ccacgcgttt | aaaccgcctg | ttcaattgaa | ctggtgtttg | aacaacgcct | 60 |
| acatcaataa | taccaatcat | cggacgaaaa | atatggaatt | aatactaaaa | tatcttatcc | 120 |
| cctccagtct | tatagttggt | aagataccaa | atttgaacat | cctgaaccag | ctgctgtcat | 180 |
| ctcaagaggc | acaccctctg | attgagcttt | atcgaccact | gatttcaacc | ctcaaaaagg | 240 |
| gtaatgtttt | cgaattccac | aaatacctgt | ttgataatga | gtcatacttt | ttaaagatga | 300 |
| acgttctcct | gccgctactt | caacggttgc | gtattttgct | gttcagaaat | ctggtccgaa | 360 |
| agctggccct | tatagagcca | ccagtcaaca | actctctgag | attttcatcc | atcaaaacag | 420 |
| ccctttcgt | ttccatttca | cccaatcaaa | acgcatactt | tcagaacaat | tattcatacc | 480 |
| tgattgttac | caacgagtcc | cagatagacg | actcctttgt | ggagaacctc | atgatcagtc | 540 |
| taatcgatca | aaacctaatt | aagggtaaac | tcgtcaacga | taaccaccga | ataattgtct | 600 |
| ccaaggccga | tacattcccg | gagatcccta | cgatttattc | gactaagttt | gccgtagact | 660 |
| cgtcattcga | ttggctggac | caatagacgt | ccttttttt | tttttttatcg | tgtctgccgt | 720 |
| ttaatgtcac | gcctcatgtt | tcaagttacg | ataacttatc | atgcagatac | taaatagtca | 780 |
| catgacgaat | gacgattttt | tgcgggttgc | tcagaggaat | atgcctctga | taagcgaggt | 840 |
| aaatgtcgag | cataagccac | ttactgtata | aatacccctt | tatcgccact | ttatcttttc | 900 |
| tccttgtccg | ttatctacaa | caccccagta | aacattaca | aacactctag | tgttgtttta | 960 |
| ctgtcccttt | taactctctt | caaacaaatc | tccatattat | ttaaactcgc | tcgtccaacg | 1020 |
| ccggcggacc | tattggagaa | aaggaataca | caaggagtta | aaaaaagtgt | ggtagaaagt | 1080 |
| gcatttgtca | taattttcca | tatgttgctg | tcactgtaat | cttttatatt | ttgttttgtt | 1140 |
| ttatgtagta | tttcaaaagg | ttcttatcat | cttactggca | taaacttgat | gtacgcagag | 1200 |
| atagcaaccg | ttgcttaggt | aagcatagta | aaaatggctg | gttttctgtc | ttattttaag | 1260 |
| gccactgttg | ggacaaaaca | caataactag | atttttatcgg | attgaacagt | gtaaaggctt | 1320 |
| cactggctta | tatcttgtat | gagtacgata | cattatccag | ttccatcaag | gcctgtggaa | 1380 |
| atattacagc | caggacatga | acctgaaagg | gagtttagtg | ggatcactgt | agataatagg | 1440 |
| aacagactta | atgaagaaaa | gtattatcag | acgaaaatag | acgaagcgtt | gaaaggggc | 1500 |
| acagaaagac | gttacgttga | tgatcatagc | agaggtcatg | agtctccaag | ttcagatttg | 1560 |
| gaggacactc | cggatcaatt | cttggaattt | cacattcatg | ataacggaga | taggaagatt | 1620 |
| tcaaggccag | acactgcttc | gtcattgatt | agtgaaaacg | acatggacta | cgatgatttg | 1680 |
| tttgttgaca | gaaagcaacc | aaaacatgct | acttctcatg | taaagcagtt | tattaggaag | 1740 |
| aatgtgttcc | aaaagaagac | tcatctacca | aacattgggg | ctagagaact | ggaattacag | 1800 |
| aaacggcttg | ctttattaga | gggcccaata | gatgacgatg | agattattag | tgctatgccc | 1860 |
| atggtagcgt | gtccctctga | ctataacgat | caacctgctg | attcaaattc | aacggtgttt | 1920 |
| aaacccccagc | gcctggcggg | | | | | 1940 |

<210> SEQ ID NO 60
<211> LENGTH: 2004
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 60

```
gacggcacgg ccacgcgttt aaaccgccag atctaacatc aaagacgaa aggttgaatg        60
aaaccttttt gccatccgac atccacaggt ccattctcac acataagtgc caaacgcaac       120
aggagggat acactagcag cagaccgttg caaacgcagg acctccactc ctcttctcct        180
caacacccac ttttgccatc gaaaaaccag cccagttatt gggcttgatt ggagctcgct       240
cattccaatt ccttctatta ggctactaac accatgactt tattagcctg tctatcctgg       300
cccccctggc gaggttcatg tttgtttatt ccgaatgca acaagctccg cattacaccc        360
gaacatcact ccagatgagg gctttctgag tgtggggtca aatagtttca tgttccccaa       420
atggcccaaa actgacagtc tcaacgctgt cttggaacct aatatgacaa agcgtgatc        480
tcatccaaga tgaactaagt ttggttcgtt gaaatgctaa cggccagttg gtcaaaaaga       540
aacttccaaa agtcggcata ccgtttgtct tgtttggtat tgattgacga atgctcaaaa       600
ataatctcat taatgcttag cgcagtctct ctatcgcttc tgaaccccgg tgcacctgtg       660
ccgaaacgca aatggggaaa cacccgcttt ttggatgatt atgcattgtc tccacattgt       720
atgcttccaa gattctggtg ggaatactgc tgatagccta acgttcatga tcaaaattta       780
actgttctaa cccctacttg acagcaatat ataaacagaa ggaagctgcc ctgtcttaaa       840
cctttttttt atcatcatta ttagcttact ttcataattg cgactggttc caattgacaa       900
gcttttgatt ttaacgactt ttaacgacaa cttgagaaga tcaaaaaaca actaattatt       960
cgaaacgcgc tcgtccaacg ccggcggacc ttcaagagga tgtcagaatg ccatttgcct      1020
gagagatgca ggcttcattt ttgatacttt tttatttgta acctatatag tataggattt      1080
tttttgtcat tttgtttctt ctcgtacgag cttgctcctg atcagcctat ctcgcagctg      1140
atgaatatct tgtggtaggg gtttgggaaa atcattcgag tttgatgttt tcttggtat       1200
ttcccactcc tcttcagagt acagaagatt aagtgagacg ttcgtttgtg caagcttcaa      1260
cgatgccaaa agggtataat aagcgtcatt tgcagcattg tgaagaaaac tatgtggcaa      1320
gccaagcctg cgaagaatgt atttttaagtt tgactttgat gtattcactt gattaagcca      1380
taattctcga gtatctatga ttggaagtat gggaatggtg atacccgcat tcttcagtgt      1440
cttgaggtct cctatcagat tatgcccaac taaagcaacc ggaggaggag atttcatggt      1500
aaatttctct gacttttggt catcagtaga ctcgaactgt gagactatct cggttatgac      1560
agcagaaatg tccttcttgg agacagtaaa tgaagtccca ccaataaaga atccttgtt       1620
atcaggaaca aacttcttgt ttcgaacttt ttcggtgcct tgaactataa aatgtagagt      1680
ggatatgtcg ggtaggaatg gagcgggcaa atgcttacct tctggacctt caagaggtat      1740
gtagggtttg tagatactga tgccaacttc agtgacaacg ttgctatttc gttcaaacca      1800
ttccgaatcc agagaaatca aagttgtttg tctactattg atccaagcca gtgcggtctt      1860
gaaactgaca atagtgtgct cgtgttttga ggtcatcttt gtatgaataa atctagtctt      1920
tgatctaaat aatcttgacg agccagacga taataccaat ctaaactctt taaacgcggt      1980
gtttaaaccc cagcgcctgg cggg                                             2004
```

<210> SEQ ID NO 61
<211> LENGTH: 2084
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 61

```
gacggcacgg ccacgcgttt aaaccgccct ccaccgtctt gatactttct gaggtgcaca    60
gaccagagga ttgtgcgaac cctaaatagt tgtatgaact caaattcaag cgctctgtga   120
cggtgccgga ataattatag gtattgttgt aatcgtcact ggttctgtcg taacatttga   180
tgtacctacc gggaactcca catatgggcc ttgcaaaaca gtcatctaat cttgttttca   240
aacgacgcgt gtagaaactt caaaattgg cataccatgg agcaatacca tctttcacca    300
tcacatctct gaatagttca gggtgaaaca acttcccaaa gaagtctcta atatggccta   360
ttatgatcaa ataaggtaa ttaaggtatg ttgcaatcag gatgaaatat ggaggttcgt    420
cctcgatggg aactggaagc ggctcgccag ggttatgctt agagacaaag agccattctt   480
tactggtcaa ggacccaaat tctttctcgg ccttctcttg tggtgaatca ttgtctatga   540
gagcatctgg gatagttttt gacatgatct ttttcagcac ggctatatag caaaaagcaa   600
aaaaaagac cgaatggaat tatatggtct aaaaaaacaa actggtggta aataaaaaa    660
aaaacgactg gtgggcggtt tcaaaggaga ctaatgatct tctatgcccg cggaaataaa   720
tagtactcca acgactgaac tcagcggtat taaagtttgt gaataaaatt acaaggctta   780
gaaagcttgg ttggtctttc ggtatctgta gatggtagag ttttgagaac atttcatttc   840
cacagtaacc aacgaacacg acccgtgact tccgggggtt ggcagatgtt aacgcgcgcg   900
tggtagaagt ttatcttggg aggtgctaga gggtgctctt ggccttgttc gctgggggga   960
agtgtttgta gttaacgtac aactcctcat gactggggat cagaatttca acttgatttg  1020
ccgctaatcg ctcgtccaac gccggcggac cttaaaaata atgatttaca tttaagaagt  1080
aacagcacat atatactgta agattaactt tgcgtaccct aaatttact aataaactta   1140
acgggttgcc atagccttgg taaccacacg tttcaatgcc aattcagctt ttctgaagtc  1200
atcaccggaa gcatcttcta gctccaaagc agccaaagcg tcagacaaag cagactcgat  1260
cttgtcctta gcacttctct ttagcttgga agacaaaatt gggtcagtga tggtagactc  1320
aatggaggaa acgtaagcct ccaacttctg tttggattcg tgacggttag cgaagtcctc  1380
gtcagccttc ttgaacttgt cagcatcgtt gatcatcttt tcgatctcgg aagaagacaa  1440
tctaccaata gagttagaaa tagtgatgtt ggcagatctt ccggtagact ctctgacagc  1500
ggtaaccttc aagataccgt tggcatcaat ctcaaagata gcctccaaca ctggctcacc  1560
agcagacata ggaggaatgt tcttcaagtc gaactcaccc aacaaggtgt tctcagaaca  1620
gttgacacgc tcaccctggt aaactgggaa ttgaacagtg gtttggtggt cgtcaacagt  1680
ggtgaaagtt cttctcttga tagttgggac agtggtgttt cttggaacaa ctgggggcaaa 1740
gacgttacct tgcatggcaa cacccaaaga aagagggata acatccaaca acaacaagtc  1800
cttggtctct tcagaggtag attgaccggt caaaatagca ccttgaacgg cggcaccgta  1860
agcgacagcc tcatcagggt tgatggattt ctccaattgc ttaccatcga agaagtcaga  1920
caacagcttt tggacctttg gaattctggt ggaaccacca accaagacga cgtcatcgac  1980
cttggatttc tcgatctttg agtccttcaa aacttgttca acaggctcca aagtagactt  2040
gaacaaatca gcgttgcggt gtttaaaccc cagcgcctgg cggg                    2084
```

<210> SEQ ID NO 62
<211> LENGTH: 1937
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

```
gacggcacgg ccacgcgttt aaaccgcccg tatctaatct ttctcgctcc ccgtacgtta      60
agaatgaaat ttctacttcc attatagaaa atagtgtatc actgccagca tcttttactc     120
acaagcaatt aaacaaagta acaatggtct ctaagcaatt ggaatcacca caggggacct     180
ttatcacgtt gaatctagtt gaaaattcag tgtccaagtt cggtgcagta cacataccac     240
aaggaaaaac cccatttgtt gttggtagag attcatcttg tgactggttg atcaaagaag     300
aaagaatttc caaaatacac tgcatgattg ccaaaaaaag gcatcctact gctaatcctt     360
ccatatttga gtcacctgct ttagggctgg aagatatttg gttactagat tttagtacaa     420
actcttgctt tgtcaatgac attaaaatag gcaagaatcg caaaactcaa atatttcatg     480
gagatgagat atgcttgttc aaagatgccc agaaaaaaga gcaactcgtt tatagggttc     540
atattgatga tggaacaggc cttttccagg gaggtgaaag aacccaagcc aattctgatg     600
acattctgga tattgatgag gttgatgaaa agttaagaga actattgaca agagcctcaa     660
ggaaacggca tatcacccct gcattggaaa ctcctgataa acgtgtaaaa agagcttatt     720
tgaacagtat tactgataac tcttgatgga ccttaaagat gtataatagt agacagaatt     780
cataatggtg agattaggta atcgtccgga ataggaatag tggtttgggg cgattaatcg     840
cacctgcctt atatggtaag taccttgacc gataaggtgg caactattta gaacaaagca     900
agccaccttt ctttatctgt aactctgtcg aagcaagcat ctttactaga gaacatctaa     960
accattttac attctagagt tccatttctc aattactgat aatcaattta aagcgctcgt    1020
ccaacgccgg cggacctgca agaataaaag ttgctcagct gaacttattt ggttacttat    1080
caggtagtga agatgtagag aatatatgtt taggtatttt tttttagttt ttctcctata    1140
actcatcttc agtacgtgat tgcttgtcag ctaccttgac aggggcgcat aagtgatatc    1200
gtgtactgct caatcaagat ttgcctgctc cattgataag ggtataagag acccacctgc    1260
tcctctttaa aattctctct taactgttgt gaaaatcatc ttcgaagcaa attcgagttt    1320
aaatctatgc ggttggtaac taaaggtatg tcatggtggt atatagtttt tcattttacc    1380
ttttactaat cagttttaca gaagaggaac gtctttctca gatcgaaat aggactaaat     1440
actggagacg atggggtcct tatttgggtg aaaggcagtg ggctacagta agggaagact    1500
attccgatga tggagatgct tggtctgctt ttccttttga gcaatctcat ttgagaactt    1560
atcgctgggg agaggatgga ctagctggag tctcagacaa tcatcaacta atttgtttct    1620
caatggcact gtggaatgag aatgatgata ttttgaagga gcgattattt ggggtcactg    1680
gagaggctgc aaatcatgga gaggatgtta aggagcttta ttattatctt gataatacac    1740
cttctcactc ttatatgaaa tacctttaca aatatccaca atcgaaattt ccttacgaag    1800
aattgatttc agagaaccgt aaacgttcca gattagaaag agagtacgag attactgact    1860
ctgaagtact gaaggataac agatattttg atgtgatctt tgaaatggcc ggtgtttaaa    1920
ccccagcgcc tggcggg                                                   1937
```

<210> SEQ ID NO 63
<211> LENGTH: 7013
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 63
gacggcacgg ccacgcgttt aaaccgcccg tatctaatct ttctcgctcc ccgtacgtta      60
agaatgaaat ttctacttcc attatagaaa atagtgtatc actgccagca tcttttactc     120
acaagcaatt aaacaaagta acaatggtct ctaagcaatt ggaatcacca caggggacct     180
ttatcacgtt gaatctagtt gaaaattcag tgtccaagtt cggtgcagta cacataccac     240
aaggaaaaac cccatttgtt gttggtagag attcatcttg tgactggttg atcaaagaag     300
aaagaatttc caaaatacac tgcatgattg ccaaaaaaag gcatcctact gctaatcctt     360
ccatatttga gtcacctgct ttagggctgg aagatatttg gttactagat tttagtacaa     420
actcttgctt tgtcaatgac attaaaatag gcaagaatcg caaaactcaa atatttcatg     480
gagatgagat atgcttgttc aaagatgccc agaaaaaaga gcaactcgtt tatagggttc     540
atattgatga tggaacaggc cttttccagg gaggtgaaag aacccaagcc aattctgatg     600
acattctgga tattgatgag gttgatgaaa agttaagaga actattgaca agagcctcaa     660
ggaaacggca tatcaccccct gcattggaaa ctcctgataa acgtgtaaaa agagcttatt     720
tgaacagtat tactgataac tcttgatgga ccttaaagat gtataatagt agacagaatt     780
cataatggtg agattaggta atcgtccgga ataggaatag tggtttgggg cgattaatcg     840
cacctgcctt atatggtaag taccttgacc gataaggtgg caactattta gaacaaagca     900
agccaccttt ctttatctgt aactctgtcg aagcaagcat ctttactaga gaacatctaa     960
accattttac attctagagt tccatttctc aattactgat aatcaattta aagcgctcgt    1020
ccaacgccgg cggacctaac aggaggggat acactagcag cagaccgttg caaacgcagg    1080
acctccactc ctcttctcct caacacccac ttttgccatc gaaaaccag cccagttatt    1140 gggcttgatt ggagctcgct cattccaatt ccttctatta ggctactaac accatgactt    1200
tattagcctg tctatcctgg ccccctggc gaggttcatg tttgtttatt tccgaatgca    1260
acaagctccg cattacaccc gaacatcact ccagatgagg gctttctgag tgtggggtca    1320
aatagtttca tgttccccaa atggcccaaa actgacagtt taaacgctgt cttggaacct    1380
aatatgacaa aagcgtgatc tcatccaaga tgaactaagt ttggttcgtt gaaatgctaa    1440
cggccagttg gtcaaaaaga aacttccaaa agtcggcata ccgtttgtct tgtttggtat    1500
tgattgacga atgctcaaaa ataatctcat taatgcttag cgcagtctct ctatcgcttc    1560
tgaaccccgg tgcacctgtg ccgaaacgca aatggggaaa caccccgcttt ttggatgatt    1620 atgcattgtc tccacattgt atgcttccaa gattctggtg gaatactgc tgatagccta    1680 acgttcatga tcaaaattta actgttctaa cccctacttg acagcaatat ataaacagaa    1740
ggaagctgcc ctgtcttaaa cctttttttt atcatcatta ttagcttact ttcataattg    1800
cgactggttc caattgacaa gcttttgatt ttaacgactt ttaacgacaa cttgagaaga    1860
tcaaaaaaca actaattatt cgaaacgatg agattcccat ccatcttcac tgctgttttg    1920
ttcgctgctt cttctgcttt ggctgaggtt cagttggttg aatctggagg aggattggtt    1980
caacctggtg gttctttgag attgtcctgt gctgcttccg gtttcaacat caaggacact    2040
tacatccact gggttagaca agctccagga aagggattgg agtgggttgc tagaatctac    2100
ccaactaacg gttacacaag atacgctgac tccgttaagg gaagattcac tatctctgct    2160
```

```
gacacttcca agaacactgc ttacttgcag atgaactcct tgagagctga ggatactgct    2220
gtttactact gttccagatg gggtggtgat ggtttctacg ctatggacta ctggggtcaa    2280
ggaactttgg ttactgtttc ctccgcttct actaagggac catctgtttt cccattggct    2340
ccatcttcta gtctacttc cggtggtact gctgctttgg gatgtttggt taaagactac     2400
ttcccagagc cagttactgt ttcttggaac tccggtgctt tgacttctgg tgttcacact    2460
ttcccagctg ttttgcaatc ttccggtttg tactctttgt cctccgttgt tactgttcca    2520
tcctcttcct tgggtactca gacttacatc tgtaacgtta accacaagcc atccaacact    2580
aaggttgaca agaaggttga gccaaagtcc tgtgacaaga ctcatacttg tccaccatgt    2640
ccagctccag aattgttggg tggtccttcc gttttttgt tcccaccaaa gccaaaggac      2700
actttgatga tctccagaac tccagaggtt acatgtgttg ttgttgacgt ttctcacgag    2760
gacccagagg ttaagttcaa ctggtacgtt gacggtgttg aagttcacaa cgctaagact    2820
aagccaagag aggagcagta caactccact tacagagttg tttccgtttt gactgttttg    2880
caccaggatt ggttgaacgg aaaggagtac aagtgtaagg tttccaacaa ggctttgcca    2940
gctccaatcg aaaagactat ctccaaggct aagggtcaac caagagagcc acaggtttac    3000
actttgccac catccagaga tgagttgact aagaaccagg tttccttgac ttgtttggtt    3060
aagggattct acccatccga cattgctgtt gaatgggagt ctaacggtca accagagaac    3120
aactacaaga ctactccacc tgttttggac tctgacggtt ccttttcttt gtactccaag    3180
ttgactgttg acaagtccag atggcaacag ggtaacgttt ctcctgttc cgttatgcat     3240 gaggctttgc acaaccacta cactcaaaag tccttgtctt tgtcccctgg taagtagacg    3300
cacgcacact cccgacagac aactagcttg ataacaggcc ccttttcctt tgtcgatatc    3360
atgtaattag ttatgtcacg cttacattca cgccctcccc ccacatccgc tctaaccgaa    3420
aaggaaggag ttagacaacc tgaagtctag gtccctattt atttttttat agttatgtta    3480
gtattaagaa cgttatttat atttcaaatt tttcttttt ttctgtacaa acgcgtgtac      3540
gcaatccccg cgtgcttggc cggccgtaag attattactt gctataagtg cgtgcctgat    3600
gaacaggata ttgcggtcaa taatgctgat ggttcattag acttcagcaa agccgatgcc    3660
aaaataagcc aatacgatct caacgctatt gaagcggctt gccagctaaa gcaacaggca    3720
gcagaggcgc aggtgacagc cttaagtgtg ggcggtaaag ccctgaccaa cgccaaaggg    3780
cgtaaagatg tgctatcgcg cggcccggat gaactgattg tggtgattga tgaccagttc    3840
gagcaggcac tgccgcaaca aacggcgagc gcactggctg cagccgccca gaaagcaggc    3900
tttgatctga tcctctgtgg cgatggttct tccgaccttt atgcccagca ggttggtctg    3960
ctggtgggcg aaatcctcaa tattccggca gttaacggcg tcagcaaaat tatctccctg    4020
acggcagata ccctcaccgt tgagcgcgaa ctggaagatg aaaccgaaac cttaagcatt    4080
ccgctgcctg cggttgttgc tgtttccact gatatcaact ccccacaaat tccttcgatg    4140
aaagccattc tcggcgcggc gaaaaagccc gtccaggtat ggtcggcggc ggatattggt    4200
tttaacgcag aggcagcctg gtcagaacaa caggttgccg cgccgaaaca gcgcgaacgt    4260
cagcgcaacg gccggccaag cacgcgggga ttgcgtacac gcgtttgtac agaaaaaaaa    4320
gaaaaatttg aaatataaat aacgttctta atactaacat aactataaaa aataaatag    4380 ggacctagac ttcaggttgt ctaactcctt cctttcggt tagagcggat gtgggggag      4440 ggcgtgaatg taagcgtgac ataactaatt acatgatatc gacaaaggaa aaggggcctg    4500
ttatcaagct agttgtctgt cgggagtgtg cgtgcgtcta acactctcct ctgttgaagg    4560
```

```
acttagtaac tggggaggac aaaccctgat gtgtaacctc acaagcgtaa accttgtgct   4620
tctcgtaatc agccttggac aaagtcaaag tggaggacaa ggagtaagtg gagtccttag   4680
agtcttgctc agtaacggat tcttgggagt taccggattg caaagcgttg tcaaccttcc   4740
actgaacctt agcctctctt gggtagaagt tgttcaacaa acaaacaacg gaagctgtac   4800
cagacttcaa ctgttcgtcg gatggtggga aaatgaaaac ggatggagca gcaacagttc   4860
tcttgatctc aaccttagta ccctgtccga aagttggtgg agtagtgtag tgctgctgac   4920
agtagtaagt agcgaaatct tctggttgca aggaggagat agtcaaagtg aagtcagtac   4980
cggatctgga accagagaat ctggatgaa caccagagta caagaaggaa gcggagtaga   5040
tcaacaactt tggagccttt cctggcttct gttgatacca agcaacagca gtattaacgt   5100
cctgggaagc tctacaagtg atagtaactc tgtcaccaac ggaagcagac aaagaagatg   5160
gggattgagt catttggatg tcagccaaag cagaagaagc agcgaacaaa acagcagtga   5220
agatggatgg gaatctcatc gtttcgaata attagttgtt ttttgatctt ctcaagttgt   5280
cgttaaaagt cgttaaaatc aaaagcttgt caattggaac cagtcgcaat tatgaaagta   5340
agctaataat gatgataaaa aaaaggttta agacagggca gcttccttct gtttatatat   5400
tgctgtcaag taggggttag aacagttaaa ttttgatcat gaacgttagg ctatcagcag   5460
tattcccacc agaatcttgg aagcatacaa tgtggagaca atgcataatc atccaaaaag   5520
cgggtgtttc cccatttgcg tttcggcaca ggtgcaccgg ggttcagaag cgatagagag   5580
actgcgctaa gcattaatga gattatttt gagcattcgt caatcaatac aaacaagac   5640 aaacggtatg ccgacttttg aagtttctt tttgaccaac tggccgttag catttcaacg   5700
aaccaaactt agttcatctt ggatgagatc acgcttttgt catattaggt tccaagacag   5760
cgtttaaact gtcagttttg ggccatttgg ggaacatgaa actatttgac cccacactca   5820
gaaagccctc atctggagtg atgttcgggt gtaatgcgga gcttgttgca ttcggaaata   5880
aacaaacatg aacctcgcca ggggggccag gatagacagg ctaataaagt catggtgtta   5940
gtagcctaat agaaggaatt ggaatgagcg agctccaatc aagcccaata actgggctgg   6000
tttttcgatg gcaaaagtgg gtgttgagga gaagaggagt ggaggtcctg cgtttgcaac   6060
ggtctgctgc tagtgtatcc cctcctgtta ggtccgccgg cgttggacga gcggcaagaa   6120
taaaagttgc tcagctgaac ttatttggtt acttatcagg tagtgaagat gtagagaata   6180
tatgtttagg tattttttt tagttttct cctataactc atcttcagta cgtgattgct   6240
tgtcagctac cttgacaggg gcgcataagt gatatcgtgt actgctcaat caagatttgc   6300
ctgctccatt gataagggta taagagaccc acctgctcct cttttaaaatt ctctcttaac   6360 tgttgtgaaa atcatcttcg aagcaaattc gagtttaaat ctatgcggtt ggtaactaaa   6420
ggtatgtcat ggtggtatat agttttcat ttacctttt actaatcagt tttacagaag   6480
aggaacgtct ttctcaagat cgaaatagga ctaaatactg gagacgatgg ggtccttatt   6540
tgggtgaaag gcagtgggct acagtaaggg aagactattc cgatgatgga gatgcttggt   6600
ctgcttttcc ttttgagcaa tctcattga gaacttatcg ctggggagag gatggactag   6660
ctggagtctc agacaatcat caactaattt gtttctcaat ggcactgtgg aatgagaatg   6720
atgatatttt gaaggagcga ttatttgggg tcactggaga ggctgcaaat catggagagg   6780
atgttaagga gctttattat tatcttgata atacaccttc tcactcttat atgaaatacc   6840
tttacaaata tccacaatcg aaatttcctt acgaagaatt gatttcagag aaccgtaaac   6900
```

```
gttccagatt agaaagagag tacgagatta ctgactctga agtactgaag gataacagat    6960
attttgatgt gatctttgaa atggcggcgg tttaaacgcg tggccgtgcc gtc          7013

<210> SEQ ID NO 64
<211> LENGTH: 2448
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64
gacggcacgg ccacgcgttt aaaccgccac cgtcaatatg aagaataaca ctaaccagta      60
ttttgaaaag aagaaagcca ttaatgaaat cgtcaaatca attcattcca atttggaagc     120
ttctttattt agttcactaa aacgctcaga tatggcatct caaactctcc cctatgttta     180
tcatatcata ctgcctaact tcaaaaacat ggccagatta atcagcctga aacctgaaga     240
aaagatcaaa cttacggaag ctgcaaaagt tcttaaagag tttggcttca cgattgagca     300
agcaaaagat gaaactttca cttacattca aaaactagtt ccgccaattg ataccgtagt     360
caattgtcag aacgaattat cgcatcaaaa gtcactttgc gcacgagcta atcagattct     420
cccatacatt gagattgagt tgaaaaggtt gaacatcacc aagagacacc taaccgattc     480
tgagcaagac ttcaagaaac tacaaggtac ttcaaagaga agaatcacag ggttgacctc     540
ccctagtaat cgacagtcgc gtgccgcatc tcttcaggag gggggggcaga ctcaaaatca     600 gctgggtacc tctatagatt ttttcgccaa atcgctttcc cgagatggaa gctcaggcag     660
aacgacacct gcacctcaga cgaactctca gagaggcacc accggacgta tttgggtccg     720
ttataacgaa gggttctcaa atgcagttcg tagaaacatc acatgggaag agctgtggaa     780
tttttaaatg tcctccataa tttcatgcgg accttgcata gtttatataa tcatactgta     840
ccaaccaaca tccacacaag gagttttcgg cctcaacata ttatcgaaac catctccctg     900
tcccttactc agatcctatt ttttcttact caattgaacg ctcgtccaac gccggcggac     960
ctccttaact acgttaggtc agtgatgaca atggaccaaa ttgttgcaag gttttctttt   1020
ttctttcatc ggcacatttc agcctcacat gcgactatta tcgatcaatg aaatccatca   1080
agattgaaat cttaaaattg cccctttcac ttgacaggat cctttttttgt agaaatgtct   1140 tggtgtcctc gtccaatcag gtagccatct ctgaaatatc tggctccgtt gcaactccga   1200
acgacctgct ggcaacgtaa aattctccgg ggtaaaactt aaatgtggag taatggaacc   1260
agaaacgtct cttcccttct ctctccttcc accgcccgtt accgtcccta ggaaatttta   1320
ctctgctgga gagcttcttc tacgcccccc ttgcagcaat gctcttccca gcattacgtt   1380
gcgggtaaaa cggaggtcgt gtacccgacc tagcagccca gggatggaaa agtcccggcc   1440
gtcgctggca ataatagcgg gcggacgcat gtcatgagat tattggaaac caccagaatc   1500
gaatataaaa ggcgaacacc tttcccaatt ttggtttctc ctgacccaaa gactttaaat   1560
ttaatttatt tgtccctatt tcaataccct ccgcgacctc caaaatcgaa ctaccttcac   1620
aatgaggaca ttgacattgt tggtctactt cgtagtggct gccttagctt tcaccccgca   1680
gaccaactcc agaattttta aaggttaccc aaagaaagtg gtttattttg acgacactgc   1740
cagcgttgtc taccatgatg gctctgacaa tgagatctat tattccaaag atgatggtgt   1800
cacttggact caactagatc ttggtggggc gtccgctcat caagtaattg ttcacccttt   1860
tgacccttct actgcctata ttttgaccac tagtgaaact cacttcgtca ccacagatag   1920
```

| | |
|---|---|
| cggatttact tggaataagg tttcctctcc agagcctcca gtaaccaacg agtttccaac | 1980 |
| gttgagccaa gagtcctcct cattgaccct gaattccaag aactttgagt atgttctgtt | 2040 |
| tgcaggccaa tgtacagacg gatcagaaat ttgcaacaga aagtactact attccttgga | 2100 |
| taacatgaga actttcaacg agctcattga agctcacagc tgtttgtttg tcgatactgc | 2160 |
| cgatgccatt gcgggtgatc attccccaaa cgctgttatc tgtgccatca ccaaccctga | 2220 |
| cggaaaactg tctttggtga aaaccgccaa cttcttcaaa gacggcatag actatgtctc | 2280 |
| tagtggtggt ggtcttattg agaatcctga actgctgggc gcctcacaca actacatctt | 2340 |
| ggctgttggt tctcatcttt tgcacaacaa agacaagttt gtatacatct catttgatgg | 2400 |
| ttcgaacttc aacaaagtga cggtgtttaa accccagcgc ctggcggg | 2448 |

<210> SEQ ID NO 65
<211> LENGTH: 2744
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65

| | |
|---|---|
| gacggcacgg ccacgcgttt aaaccgcctc tctgctcttc aagaagtaaa acgctgggcg | 60 |
| gcaaagaagg aaaagtccaa taaagtatc tgtaagaggt ggaagtgctc agatagtgcg | 120 |
| aagagaggaa taaatgaatg caagagcgcg atggagtgta gcgtgattac atcatcagat | 180 |
| gctacattga ttctctgata tgaatggtga tggaactttc tagaggttcc ttgaagaaat | 240 |
| aaatacattt acaagcagaa ctccacttt tcacggagaa tcatctaagt taggcatacg | 300 |
| aaggatctcg ccttcgttgt ttgcactcat ctcctgtagt ttagcgagaa tcttggagtc | 360 |
| cttccacttt tcaggcaatg gggtaacctc gtagtttttc acggcccagt aataaatatc | 420 |
| ccaatccaac tcgtttaata agtcatcata ctcttccatc tcttccacac tcattgtcgg | 480 |
| tagatagcgt tttgcgaaac gagacagaag aaggtctgtt ccaagattc ctctctttct | 540 |
| tgactgataa accagacggc gtctcttgac atcttccgac tcgttatcac gtttcagagg | 600 |
| ttcaactttc agtatcagct cctgcctcaa gaaggggaga gaatgaaaag atttcgaaaa | 660 |
| caccctggga caagtcttgc taccttgaaa ctgagttctt tggaaaagcc ggagcataat | 720 |
| gggtgaatta agcagaaaga aggtaactga tttgctgaga cccaaatcat ctacagtttc | 780 |
| gcgaagcata aagttcacac tgattttctg gggaagaact ggtaaaccac atgttgtctc | 840 |
| cattccacga taaaccgttc aagcaaggcc gtcttagaat gcacaagaca atttaggtaa | 900 |
| actacctttc ctgaaagcga aagcagacgt tacaatctgt ttcatccccc aactgcactc | 960 |
| ctctctcctc tgctagccaa gacgatcttt catagaattt gatggaattt acgcgaaatc | 1020 |
| gccacgtaat catatttcga acagcgctcg tccaacgccg gcggacctcc ttaactacgt | 1080 |
| taggtcagtg atgacaatgg accaaattgt tgcaaggttt ttcttttct ttcatcggca | 1140 |
| catttcagcc tcacatgcga ctattatcga tcaatgaaat ccatcaagat tgaaatctta | 1200 |
| aaattgcccc tttcacttga caggatcctt ttttgtagaa atgtcttggt gtcctcgtcc | 1260 |
| aatcaggtag ccatctctga aatatctggc tccgttgcaa ctccgaacga cctgctggca | 1320 |
| acgtaaaatt tccgggggta aaacttaaat gtggagtaat ggaaccagaa acgtctcttc | 1380 |
| ccttctctct ccttccaccg cccgttaccg tccctaggaa attttactct gctggagagc | 1440 |

```
ttcttctacg gcccccttgc agcaatgctc ttcccagcat tacgttgcgg gtaaaacgga    1500
ggtcgtgtac ccgacctagc agcccaggga tggaaaagtc ccggccgtcg ctggcaataa    1560
tagcgggcgg acgcatgtca tgagattatt ggaaaccacc agaatcgaat ataaaaggcg    1620
aacacctttc ccaattttgg tttctcctga cccaaagact ttaaatttaa tttatttgtc    1680
cctatttcaa tacctcccgc gacctccaaa atcgaactac cttcacaatg aagatctcta    1740
ccattgcaag ttctacgttg ttcgctgttg gtgctttagc cgaatccgaa cccgctgagt    1800
tcagacccct ggaagctcag ttggacaagt catctttctt tgaacaattc gacaaggaac    1860
cgaaactcgg cgacacctgg aagatctccc atgccgttaa gaatgaagaa ttcacttatg    1920
ttggagaatg ggccattgag gaacctgttg tctatcctgg attcaagaag gacagggggtc   1980 tggttgtgaa atctgaggca gctcaccacg caatatctgc ccaattacca caggtatttg    2040
acaacactga caatacgttg gtcttgcaat acgaagtcaa gcttcaacaa ggattgaact    2100
gtggaggtgc ttatgttaaa ttattgagtg ctgagggtct gaacaagaat gagttctcta    2160
acgagacccc ttatcaagtc atgtttggtc ctgataaatg tggaaccacg aataaagtgc    2220
acttgattat taagaggaag aacccagcca ccggcgaata tgaggaacat caattggcta    2280
ctcctccaat gggtagaatc gtcaagacta cttctctata caccctgatt atcaagccca    2340
ataatgactt tgaaatcaga atcaacggtg aggttgctaa agctggtaac ttgttgaacg    2400
agaagttgat aaagccacca tttggcgctc cgaaggagat tgacgatccg gaagaccaaa    2460
aacccgaaga ttgggttgat gaagacatga tcccagatcc agatgctgtc aagcctgaag    2520
attgggacga gtccgagcca ttgcgaatcg tcgatccgga agctgtgaaa ccagaaaact    2580
ggaacgaaga tgctgaattg tacatccctg atccagaggc caccaagccc gaagactggg    2640
acgatgaaga ggatggcgaa tgggttgctc ctgttattcc aaatccagaa tgcgcagata    2700
ttggatgtgg cccttgcggt gtttaaaccc cagcgcctgg cggg                    2744

<210> SEQ ID NO 66
<211> LENGTH: 2585
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66
gacggcacgg ccacgcgttt aaaccgccga ttgtcttcaa acatttacac tgagtgttgg      60
aaccattaag ttgccatatt tgagccgtcg aatctttggc gacggtgaca aatatcagtt    120
catcaactgt atcccaagca atgcaataga ctggcttgtt agaggttgta ttgatctgca    180
ataaagagtc ccatacattt tccttgaacc ttttccatat gcagagggtt ttatcagatc    240
ttgaatacgc caatctattt cccttgttga attctaaagt gatgatatca gtgctagttc    300
ggtgattttc taaagagcca tcattcaact ccgttgattt cagatcagta aaaagctgct    360
tgtccctagc tagtgaaggg ttggtcatta tagaggcctt caaacaatac ttttcaaaat    420
agacacgccg cgcgaatcct cacgatagcg aaataccaac tccacagatg ttaccacgta    480
acatttctcc tctgatcaaa tggctcctca acaccaagg caacgtatcg caaacgaaaa     540
attcgtaaag agagctgaag ctcagcaggg taaggtgaag aaggctagat ccaagcgtga    600
atttccagtt tcgactaagt gggttatcat attgctcttc ttgctgattg ggggagggggt   660 cctggagatt ttgagattgt ttttttgaat gatcttttca aaggtctagg tctttttgga    720
```

```
aggaaatggt tatactttgg cctttcatta tttgagagga tagtcgtatt tttctaccgg      780
gagaaggtag gcataacgtt aattgcgaat tttcacttac tttagatggg tactgatctt      840
caactcacga taatttcatt gcaccatgta tctctaaact ggcgtgtcgg aactcacaca      900
ccattggaac ttattgatta accaatacat agattaattg actcgcctga taatactaat      960
caccgttcac tacttctctt agtatcttct cctactggag tcgttctacg ctcgtccaac     1020
gccggcggac ctccttaact acgttaggtc agtgatgaca atggaccaaa ttgttgcaag     1080
gttttctttt ttctttcatc ggcacatttc agcctcacat gcgactatta tcgatcaatg     1140
aaatccatca agattgaaat cttaaaattg cccctttcac ttgacaggat ccttttttgt     1200
agaaatgtct tggtgtcctc gtccaatcag gtagccatct ctgaaatatc tggctccgtt     1260
gcaactccga acgacctgct ggcaacgtaa aattctccgg ggtaaaactt aaatgtggag     1320
taatggaacc agaaacgtct cttcccttct ctctccttcc accgcccgtt accgtcccta     1380
ggaaatttta ctctgctgga gagcttcttc tacggccccc ttgcagcaat gctcttccca     1440
gcattacgtt gcgggtaaaa cggaggtcgt gtacccgacc tagcagccca gggatggaaa     1500
agtcccggcc gtcgctggca ataatagcgg cggacgcat  gtcatgagat tattggaaac     1560
caccagaatc gaatataaaa ggcgaacacc tttcccaatt ttggtttctc ctgacccaaa     1620
gactttaaat ttaatttatt tgtccctatt tcaataccctc ccgcgacctc caaaatcgaa     1680
ctaccttcac aatgttgtca tcaagatggt gttcatgtaa aaagcagagt ccaagtcgac     1740
aagtaggtca gttactgcgc tacatgtcta gcaaggtaat tggaattgat ttaggaacta     1800
cgaactctgc tgttgccgtt tttgaaggaa aagaaccaaa aatcctggag aacgaagagg     1860
gaaagagaac gacaccttct attgttgcat ttaccccaga aactgtgcta gtaggagaac     1920
cagcaaagag acaatctatt ctgaactatc agaacacttt ttatgctaca aaaaggctca     1980
ttggtcgcaa gtattcggat cctgaagttc aacgggatat ttccaacgtt ccttacagta     2040
taattgaaca tgaaaatggg gatgcgtggc ttcaaaacat gcactcaggt caaaaatact     2100 cccctctca  aattggtagt ttgatattgg gaaagatgaa agagattgca gagctaaatc     2160
tttcccagtc tattagccag gctgtggtca ctgtgcctgc ctacttcaac gattcgcaaa     2220
gacaagcaac taagattgct ggtgatttag tgggtcttaa agttttaaga gttatcaatg     2280
agcccaccgc tgcttctttg gcttacggat tgaatagaaa aaatgacggg ataattgccg     2340
tttacgacct tggtggtgga acttttgata tctccatatt ggatatcgaa gccggcgtct     2400
ttgaagttat tgcgacgaat ggtgacacac atcttggagg ggaagatttt gaccatttgc     2460
tggtggacta catattgcaa cagtttcaat cgcagacagg acaagatcta tctactgacc     2520
gtttggccct gcaaagaatt cgtcaggctg ctgaaaacgg tgtttaaacc ccagcgcctg     2580
gcggg                                                                2585
```

<210> SEQ ID NO 67
<211> LENGTH: 2740
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67

```
gacggcacgg ccacgcgttt aaaccgccag aatcacaaaa ttcttttcat cttcagacat       60
```

```
gtatatctgg ctcagagatt tgaagggaat ctgaaacctg gttttagacg gaaggtcaac    120
tatgaggtac aggctgttag gccatatgct taaaaaagga acaggtaagg atatgttttt    180
attgatgatg gagatgtggt gcaagtgaat cctgagaacc tcttttttct tttcaaacgc    240 attttttgtct tcaattccat tcttcgatct tttaacgatg ggagcgctta ttttgtctat    300
gatgtggctt tgaagatcag ctgttgtatt caaactatca ctttgagtca acgagttctt    360
aggtagtctt tgaaaccgtg aaagggaacc cattttcttc gaacccaggg atttcactga    420
tcctctggcc attgacgccg atcgtgagtt ctgtagagtt cccttcgtct taagagagag    480
ggggaataat taaagatcaa gtaatgttct acctacaaaa gataaagatg accttaatgt    540
ttttagcgag gtatagctgg gagtcccaaa gaagtagcta gggcggtgag aggattttt    600 tctcgtgcgc atataatcgc tagcctagtt aaagcatctt gacgacgtac taatatctgg    660
aagacttcag agcacagaaa ctatgcctgg tgagttcatg gtgaccgtat tgagcacatc    720 caaaagatc ttattctctc cagtacaatc agcagaaggc cttatccatc ttgctgttcc    780
actacctcat tccagtatac ttctaatcat cgcctctaga taagcagac gatctcaaga    840 accaccctca tcttgaaacg tggactcgag tcgcaatgtc ctgtatcatt cctacgtcac    900
aagccatcac tgggttctct cgccccccta cgaaacgcta gctattgcta tatggaacaa    960
tctagaccgt aagttagggc cactctgttc atttctcgtc ttagtcagct gatcctcgaa   1020
acgatctacg ctcgtccaac gccggcggac ctccttaact acgttaggtc agtgatgaca   1080
atggaccaaa ttgttgcaag gttttttctt ttctttcatc ggcacatttc agcctcacat   1140
gcgactatta tcgatcaatg aaatccatca agattgaaat cttaaaattg cccctttcac   1200
ttgacaggat ccttttttgt agaaatgtct tggtgtcctc gtccaatcag gtagccatct   1260
ctgaaatatc tggctccgtt gcaactccga acgacctgct ggcaacgtaa aattctccgg   1320
ggtaaaactt aaatgtggag taatggaacc agaaacgtct cttcccttct ctctccttcc   1380
accgcccgtt accgtcccta ggaaatttta ctctgctgga gagcttcttc tacggccccc   1440
ttgcagcaat gctcttccca gcattacgtt gcgggtaaaa cggaggtcgt gtacccgacc   1500
tagcagccca gggatggaaa agtcccggcc gtcgctggca ataatagcgg gcggacgcat   1560
gtcatgagat tattggaaac caccagaatc gaatataaaa ggcgaacacc tttcccaatt   1620
ttggtttctc ctgacccaaa gactttaaat ttaatttatt tgtccctatt tcaatacctc   1680
ccgcgaccct caaaatcgaa ctaccttcac aatgaggata gtaaggagcg tagctatcgc   1740
aatagcctgt cattgtataa cagcgttagc aaaccctcaa atccctttg acggcaacta    1800 caccgagatc atcgtgccag ataccgaagt taacatcgga cagattgtag atattaacca   1860
cgaaataaaa cccaaactgg tggaactggt caacacagac ttcttcaaat attacaaatt   1920
aaacctatgg aaaccatgtc cgttttggaa tggtgatgag ggattctgca agtataagga   1980
ttgctctgtc gactttatca ctgattggtc tcaggtgcct gatatctggc aaccagacca   2040
attgggtaag cttggagata acacggtaca taaggataag ggccaagatg aaaatgagct   2100
gtcctcaaat gattattgcg ctttggataa agacgacgat gaagatttag tatatgtcaa   2160
tttgattgat aaccctgaaa gattcaccgg ttatggtggt cagcaatctg aatctatttg   2220
gactgcggtc tatgatgaga actgtttcca gccgaatgaa ggatcacaat gggtcaagt    2280 tgaagacctc tgtttggaga aacagatctt ttaccgattg gtttctggtt tgcattctag   2340
tatctccacc cacctcacaa acgaatatct gaatttgaaa aatggagcat acgaaccaaa   2400
tttgaaacag ttcatgatca aagttgggta ttttactgaa agaattcaaa acttacatct   2460
```

-continued

```
caattatgtc cttgtattga agtcactaat aaagctacaa gaatacaatg ttatcgacaa    2520
tctacctctc gatgactctt tgaaagctgg tcttagcggt ttaatatctc aaggagcaca    2580
gggtattaac cagagctctg atgattatct atttaacgag aaggttcttt tccaaaatga    2640
ccaaaatgat gatttgaaaa atgaattccg tgacaaattc cgcaacgtga ctagattaat    2700
ggattgtgtc cacggtgttt aaacccagc gcctggcggg                          2740
```

METHODS FOR GENOMIC INTEGRATION IN *PICHIA* AND OTHER HOST CELLS

CROSS-REFERENCE TO RELATED PATENT APPLICATIONS

The present application is a divisional of U.S. patent application Ser. No. 16/646,001, filed Mar. 10, 2020, which is a U.S. National Phase Application Under 371 of PCT/US2018/050613 filed Sep. 12, 2018, which claims priority to U.S. Provisional Patent Application No. 62/560,026, filed on Sep. 18, 2017 and U.S. Provisional Patent Application No. 62/666,923 filed on May 4, 2018, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 13, 2022, is named 101928-1333775 SL.txt and is 68,619 bytes in size.

BACKGROUND OF THE INVENTION

Typically *P. pastoris* is transformed using vectors or linear constructs with drug or auxotrophic markers. To improve protein production from integrated constructs, clones are passaged on increasing concentrations of a drug, selecting for amplification of the construct in a random fashion. Targeted integration is possible, and greatly improved when YKU70 is deleted in yeast cells to reduce NHEJ (non-homologous end joining) repair mechanisms. However, available markers are limited, and marker recycling (i.e., reusing of the same marker) is necessary for more ambitious engineering efforts. For rapid strain engineering, for example, in *P. pastoris*, a highly efficient, marker-less and targeted homologous integration transformation method is desired. Recently, Weninger et al. (*Journal of Biotechnology* 235:139-149 2016) reported a CRISPR protocol in *P. pastoris* using a strong constitutive promoter for Cas9 expression, and an RNA polymerase II promoter driving expression of the gRNA, with all components contained on a large plasmid. The study reported high efficiency of insertion and deletion (indel) introduction by NHEJ into a single gene, or multiple genes, which usually results in loss of function, equivalent to a knockout. However, when marker-less donor DNA was provided for targeted integration, a rate of only 2.4% was observed.

Thus, current known methods are in need of improvement. The present invention addresses these and other needs.

BRIEF SUMMARY OF THE INVENTION

The present invention provides methods of disrupting or inserting a desired donor DNA molecule into one or more target sites in a host cell genome.

In some embodiments, the methods comprise (a) contacting a host cell, which comprises a nucleic acid encoding an RNA-guided DNA endonuclease, with: (i) a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and (ii) a second linear nucleic acid which comprises, from 5' to 3', a RNA polymerase II promoter, a first nucleic acid encoding a first ribozyme, a nucleic acid encoding a guide RNA, a second nucleic acid encoding a second ribozyme, and a terminator, wherein the guide RNA guides the DNA nuclease to the target site. A transformed host cell expressing the selectable marker is then selected. In some embodiments, NHEJ is reduced in the host cell. In some embodiments, the nucleic acid encoding an RNA-guided DNA endonuclease is integrated into the host cell genome.

In some embodiments, the method further comprises contacting the host cell with a donor DNA molecule capable of homologous recombination with the target site, whereby homologous recombination in the host cell results in integration of the donor DNA molecule at the target site. In some embodiments, the donor DNA molecule comprises a nucleic acid sequence encoding an antibody. In some cases, the step of contacting includes contacting the cell with two or more donor DNA molecules capable of homologous recombination with different target sites, whereby homologous recombination in the host cell results in integration of the donor DNA molecules at the different target sites.

The host cell used in any of the methods provided herein may be, for example, a non-conventional yeast cell. In some embodiments, the host cell is *Pichia*, in particular, *Pichia pastoris*.

In some embodiments, the step of contacting includes contacting the cell with two or more second linear nucleic acid molecules, wherein each second linear nucleic acid molecule comprises a nucleic acid encoding a different guide RNA, which guides the DNA nuclease to a different target site. The methods according to the present invention result in high efficiency for single, double, or multiple efficiency for targeted integration of donor nucleic acids into the host cell genome. As used herein, the targeting efficiency refers to a percentage of transformed cells comprising a successful integrated donor nucleic acids among screened cells.

In some embodiments, the nucleic acid encoding the RNA-guided DNA endonuclease can be operably linked to a *Pichia* pPGK1 promoter. In addition, the nucleic acid encoding the RNA-guided DNA endonuclease can be integrated in a YKU70 gene, thereby reducing NHEJ activity in the host cell. In certain embodiments, the nucleic acid encoding the RNA-guided DNA endonuclease can be integrated at another genomic locus to reduce NHEJ, such as in a YKU80 gene. In other embodiments, the nucleic acid encoding the RNA-guided DNA endonuclease can be integrated at a different genomic locus, and one or more genes involved in the NHEJ process can be functionally disrupted separately. The RNA-guided DNA endonuclease can be Cas9. In some embodiments, the nucleic acid sequence encoding the Cas9 is codon optimized for expression in *Saccharomyces*.

The invention also provides host cells made by the methods of the invention. The host cell may comprise a donor DNA molecule comprising a nucleic acid sequence encoding an antibody. Thus, the invention also provides methods of producing an antibody. The methods comprise culturing the host cell under conditions suitable for production of the antibody and recovering the antibody produced by the host cell. The host cell can be *Pichia*.

DEFINITIONS

Figure 1A:
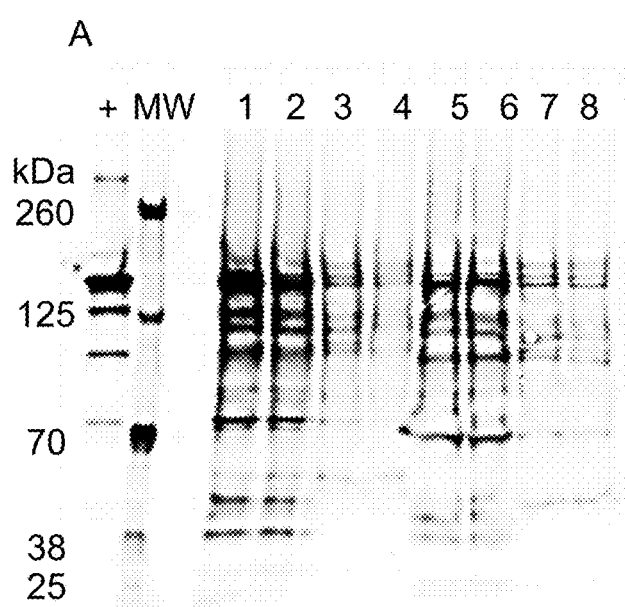
FIGS. 1A and 1B illustrate secretion of full-length HERCEPTIN® and RITUXAN® by engineered *P. pastoris* strains. Protein A purified samples were assayed by Western Blot under non-reducing (A) and reducing (B) conditions. Lanes 1-4, Protein A purified samples; lanes 5-8, Protein A purified and Endo H$_f$ treated samples. Lanes 1 and 5, HERCEPTIN® with pre-alpha secretion leader sequence; lanes 2 and 6, HERCEPTIN® with pre-alpha secretion leader sequence and KR mutated to TR in LC; lanes 3 and 7, RITUXAN® with Kar2 leader sequence; lanes 4 and 8, RITUXAN® with Kar2 sequence and KR mutated to TR in LC. MW, molecular weight marker, with quantities on the left of each gel. +, BIIB antibody standard.

As used in this specification and the appended claims, the singular forms "a," "an," and "the" include plural reference unless the context clearly dictates otherwise.

The term "nucleic acid" or "nucleotide" refers to deoxyribonucleic acids (DNA) or ribonucleic acids (RNA) and polymers thereof in either single- or double-stranded form. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)).

The term "gene" can refer to the segment of DNA involved in producing or encoding a polypeptide chain. It may include regions preceding and following the coding region (leader and trailer) as well as intervening sequences (introns) between individual coding segments (exons). Alternatively, the term "gene" can refer to the segment of DNA involved in producing or encoding a non-translated RNA, such as an rRNA, tRNA, guide RNA, or micro RNA A "promoter" is defined as one or more a nucleic acid control sequences that direct transcription of a nucleic acid. As used herein, a promoter includes necessary nucleic acid sequences near the start site of transcription. A promoter also optionally includes distal enhancer or repressor elements, which can be located as much as several thousand base pairs from the start site of transcription.

As used herein, the term "marker-less" refers to integration of a donor DNA into a target site within a host cell genome without accompanying integration of a selectable marker. The term also refers to instances where a selectable marker gene is not integrated into the host cell genome for the recovery of a host cell in which a donor DNA is integrated into the host cell genome. In some embodiments, the term also refers to the recovery of such a host cell without utilizing a selection scheme that relies on integration of selectable marker into the host cell genome. For example, in certain embodiments, a selection marker that is episomal or extrachromasomal may be used to select for cells comprising a plasmid comprising a gRNA. Such use would be considered marker-less, as long as the selectable marker is not integrated into the host cell genome.

As used herein, the term "operably linked" refers to a functional linkage between nucleic acid sequences such that the sequences encode a desired function. For example, a coding sequence for a gene of interest, e.g., a selectable marker, is in operable linkage with its promoter and/or regulatory sequences when the linked promoter and/or regulatory region functionally controls expression of the coding sequence. It also refers to the linkage between coding sequences such that they may be controlled by the same linked promoter and/or regulatory region; such linkage between coding sequences may also be referred to as being linked in frame or in the same coding frame. "Operably linked" also refers to a linkage of functional but non-coding sequences, such as an autonomous propagation sequence or origin of replication. Such sequences are in operable linkage when they are able to perform their normal function, e.g., enabling the replication, propagation, and/or segregation of a vector bearing the sequence in a host cell.

As used herein, the term "transformation" refers to a genetic alteration of a host cell resulting from the introduction of exogenous genetic material into the host cell.

As used herein, the term "selecting a host cell expressing a selectable marker" also encompasses enriching for host cells expressing a selectable marker from a population of transformed cells.

As used herein, the term "selectable marker" refers to a gene which functions as guidance for selecting a host cell comprising a marker, for example, a marker expressed by a circular, extrachromosomal nucleic acid in the host cell, as described herein. The selectable markers may include, but are not limited to: fluorescent markers, luminescent markers and drug selectable markers, and the like. The fluorescent markers may include, but are not limited to, genes encoding fluorescence proteins such as green fluorescent protein (GFP), cyan fluorescent protein (CFP), yellow fluorescent protein (YFP), red fluorescent protein (dsRFP) and the like. The luminescent markers may include, but are not limited to, genes encoding luminescent proteins such as luciferases. Drug selectable markers suitable for use with the methods and compositions provided herein include, but are not limited to, resistance genes to antibiotics, such as ampicillin, streptomycin, gentamicin, kanamycin, hygromycin, tetracycline, chloramphenicol, and neomycin. In some embodiments, the selection may be positive selection; that is, the cells expressing the marker are isolated from a population, e.g. to create an enriched population of cells comprising the selectable marker. In other instances, the selection may be negative selection; that is, the population is isolated away from the cells, e.g. to create an enriched population of cells that do not comprise the selectable marker. Separation can be by any convenient separation technique appropriate for the selectable marker used. For example, if a fluorescent marker is used, cells can be separated by fluorescence activated cell sorting, whereas if a cell surface marker has been inserted, cells can be separated from the heterogeneous population by affinity separation techniques, e.g. magnetic separation, affinity chromatography, "panning" with an affinity reagent attached to a solid matrix, or other convenient technique.

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

As used herein, the term "complementary" or "complementarity" refers to specific base pairing between nucleotides or nucleic acids. In some embodiments, for example, and not to be limiting, base pairing between a guide RNA and a target site or region in the genome of a host cell is described. Complementary nucleotides are, generally, A and T (or A and U), and G and C. The guide RNAs described herein can comprise sequences, for example, a DNA targeting sequence that is perfectly complementary or substantially complementary (e.g., having 1-4 mismatches) to a genomic sequence in a host cell.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-guided DNA endonuclease, Cas9, in complex with a guide RNA to recognize and cleave foreign nucleic acid.

As used herein, the terms "cleave," "cleavage" and/or "cleaving" with respect to an RNA-guided endonuclease, for example, Cas9, refers to the act of creating a break in a particular nucleic acid. The break can leave a blunt end or sticky end (i.e., 5' or 3' overhang), as understood by those of skill in the art. The terms also encompass single strand DNA breaks ("nicks") and double strand DNA breaks.

As used herein, the term "Cas9" refers to an RNA-guided nuclease (e.g., of bacterial or archeal orgin, or derived therefrom). RNA-guided nucleases include the foregoing Cas9 proteins and homologs thereof, and include but are not limited to, Cpf1 (See, e.g., Zetsche et al., Cell, Volume 163, Issue 3, p 759-771, 22 Oct. 2015).

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. Variants of any of the Cas9 nucleases provided herein can be optimized for efficient activity or enhanced stability in the host cell. Thus, engineered Cas9 nucleases, for example, codon optimized Cas9 nucleases for expression in *Pichia* or *Saccharomyces* are also contemplated.

As used herein, the phrase "disrupting" or "disruption" in the context of disrupting a target site in a host cell genome refers to inducing a nucleic acid break in the target site. A disruption can be used to edit the genome. As used herein the term "editing" refers to a structural change in the sequence of the genome at a target site. For example, the host cell genome may be edited by deleting or inserting a nucleotide sequence into the genome of the cell. The nucleotide sequence can encode a polypeptide or a fragment thereof. Such editing can be performed, for example, by inducing a double stranded break within a target site in the genome of a host cell, or a pair of single stranded nicks on opposite strands and flanking the target site in the genome of a host cell. Methods for inducing single or double stranded breaks at or within a target site include the use of an RNA-guided DNA endonuclease, or a derivative thereof, and a guide RNA directed to the target site in the genome of a host cell.

As used herein the phrase "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is exogenous to the cell); (b) naturally found in the host cell (i.e., endogenous) but present at an unnatural quantity in the cell (i.e., greater or lesser quantity than naturally found in the host cell); or (c) be naturally found in the host cell but positioned outside of its natural locus.

As used herein the term "homologous recombination" refers to a cellular process in which nucleotide sequences are exchanged between two similar or identical molecules of DNA.

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term homology directed repair (HDR) refers to a cellular process in which cut or nicked ends of a DNA strand are repaired by polymerization from a homologous template nucleic acid, for example a donor DNA molecule. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid, for example, a donor DNA molecule can be introduced to obtain a specific HDR-induced change of the sequence at the target site. In this way, specific sequences can be introduced at the cut site.

As used herein, the phrases "introducing" or "contacting" in the context of introducing a nucleic acid or protein into a host cell refers to any process that results in the presence of a heterologous nucleic acid or polypeptide inside the host cell. For example, the terms encompass introducing a nucleic acid molecule (e.g., a plasmid or a linear nucleic acid) that encodes the nucleic acid of interest (e.g., an RNA molecule) or polypeptide of interest and results in the transcription of the RNA molecules and translation of the polypeptides. The terms also encompass integrating the nucleic acid encoding the RNA molecules or polypeptides into the genome of a progenitor cell. The nucleic acid is then passed through subsequent generations to the host cell, so that, for example, a nucleic acid encoding an RNA-guided endonuclease is "pre-integrated" into the host cell genome. In some cases, introducing refers to translocation of a nucleic acid or polypeptide from outside the host cell to inside the host cell. Various methods of introducing nucleic acids, polypeptides and other biomolecules into host cells are contemplated, including but not limited to, electroporation, contact with nanowires or nanotubes, spheroplasting, PEG 1000-mediated transformation, biolistics, lithium acetate transformation, lithium chloride transformation, and the like.

As used herein, the term "full-length antibody" refers to an antibody having a structure substantially similar to a native antibody structure. A full-length antibody includes four polypeptides—two light chains and two heavy chains joined by disulfide bonds to form a "Y" shaped molecule. Each heavy chain includes a constant region and a variable region join by a hinge region. The two constant regions of the two heavy chains form an Fc domain. A full-length antibody may be of any isotype (e.g., IgA, IgD, IgE, IgG, and IgM), which is defined by the heavy chain of the antibody.

DETAILED DESCRIPTION OF THE INVENTION

Methods of Disrupting a Target Site in a Host Cell Genome

Provided herein are methods of disrupting one or more target sites in a host cell genome. These methods allow efficient, simultaneous integration of one or more donor DNA molecules into a host cell genome. In some of the methods the one or more donor DNA molecules are integrated into the host cell genome without concomitant integration of a selectable marker into the host cell genome.

In some embodiments, disruption of one or more target sites comprises (a) contacting a host cell, which expresses an RNA-guided DNA endonuclease, with: (i) a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and (ii) a second linear nucleic acid which comprises, from 5' to 3', a RNA polymerase II promoter, a first nucleic acid encoding a first ribozyme, a nucleic acid encoding a guide RNA, a second nucleic acid encoding a second ribozyme, and a terminator, wherein the guide RNA guides the DNA nuclease to the target site. A transformed host cell expressing the selectable marker is then selected.

In some embodiments, disruption of one or more target sites comprises (a) contacting a host cell, which expresses an RNA-guided DNA endonuclease, with: (i) a first linear nucleic acid capable of homologous recombination with itself or with one or more additional linear nucleic acids contacted with the host cell, whereby homologous recombination in the host cell results in formation of a circular extrachromosomal nucleic acid comprising a coding sequence for a selectable marker and (ii) a second linear nucleic acid which comprises, from 5' to 3', a RNA polymerase II promoter, a first nucleic acid encoding a first ribozyme, a nucleic acid encoding a guide RNA, a second nucleic acid encoding a second ribozyme, and a terminator, wherein the guide RNA guides the DNA nuclease to the target site, wherein the host cell has reduced NHEJ activity. A transformed host cell expressing the selectable marker is then selected.

In some embodiments, the method further comprises contacting the host cell with a donor DNA molecule capable of homologous recombination with the target site, whereby homologous recombination in the host cell results in integration of the donor DNA molecule at the target site. In some embodiments, the donor DNA molecule is a heterologous donor DNA molecule. In some embodiments, the donor DNA molecule is flanked by nucleotide sequences that are homologous to genomic sequences flanking the target site. In some embodiments, the donor DNA molecule comprises a homologous sequence at the 5' terminus that is about 70%, 75%, 80%, 85%, 90%, 95% or 100% homologous to a 5' region of a selected genomic target site In some embodiments, the donor DNA molecule comprises a homologous sequence at the 3' terminus that is about 70%, 75%, 80%, 85%, 90%, 95% or 100% homologous to a 3' region of a selected genomic target site. In some cases, each of the homologous sequences flanking the donor DNA molecule comprises from about 50 to about 5,000 nucleotides, from about 100 to 2500 nucleotides, from about 200 to 1500 nucleotides, from about 500 to about 1000 nucleotides, or any number of nucleotides within these ranges. See, for example, U.S. Pat. No. 9,476,065.

In some embodiments, NHEJ is reduced in the host cell prior to contacting the host cell with the first linear nucleic acid, the second linear nucleic acid and/or the donor DNA molecule. In some embodiments, NHEJ is reduced in the host cell simultaneously with contacting the host cell with the first linear nucleic acid, the single linear nucleic acid and/or the donor DNA molecule. In some embodiments, NHEJ is reduced in the host cell after contacting the host cell with the first linear nucleic acid, the single linear nucleic acid and/or the donor DNA molecule.

In some embodiments, the donor DNA molecule comprises a nucleic acid of interest. For example, the donor DNA molecule may comprise a gene of interest that can be knocked in to a host genome. In other embodiments, the donor DNA molecule functions as a knockout construct that is capable of specifically disrupting a target gene upon integration of the construct into the target site of the host cell genome, thereby rendering the disrupted gene non-functional. Examples of nucleic acids of interest include, but are not limited to, a protein-coding sequence, a promoter, an enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In specific embodiments, the nucleic acid of interest does not comprise a nucleic acid encoding a selectable marker.

In some embodiments the nucleic acid of interest encodes an antibody, for example, and not to be limiting, a monoclonal antibody, a Fab fragment, a single-chain variable fragment (scFv), a dimeric single-chain variable fragment (di-ScFv), or a single-domain antibody (sdAb). In some embodiments, the nucleic acid of interest encodes the full-length antibody HERCEPTIN® (trastuzumab). In some embodiments, the nucleic acid of interest encodes the full-length antibody RITUXAN® (rituximab). In some embodiments, the nucleic acid of interest excludes the nucleic acid that encodes the full-length antibody HERCEPTIN® (trastuzumab), the full-length antibody RITUXAN® (rituximab), or the full-length antibody BIIB. In other embodiments, the nucleic acid of interest encodes an enzyme, a hormone, a growth factor, an anticoagulant, blood factors, an engineered protein, an interferon, an interleukin, a thrombolytic, a viral protein or a bacterial protein.

In the methods and compositions provided herein, the host cell can be a prokaryotic cell or a eukaryotic cell. In some embodiments, the host cell is selected from the group consisting of a fungal cell, a bacterial cell, a plant cell, an insect cell, an avian cell, a fish cell and a mammalian cell. In some embodiments, the mammalian cell is selected from the group consisting a rodent cell, a primate cell and a human cell. In some embodiments, the fungal cell is a yeast cell. In some embodiments, the yeast cell is a non-conventional yeast cell. A non-conventional yeast cell refers to yeast species which utilizes non-homologous end joining as a predominant mechanism for a DNA repair system, in contrast a conventional yeast cell (e.g., *Saccharomyces* or *Schizomyces*), which utilizes homologous recombination as a dominant mechanism for DNA repair system. Examples of non-conventional yeast cells include *Pichia* (e.g., *P. pastoria*), *Kluyveromyces* (*K. marxianus*, or *K. lactis*), *Hansenula*

(e.g., *H. polymorpha*), or *Arxula* (*A. adninivorans*). In some embodiments, the yeast cell is a *Pichia* cell. In specific embodiments, the yeast cell is a *Pichia pastoris* cell. Examples of host cells that can be used in the methods described herein are described in International Application Publication No. WO2015/095804. In some embodiments, the host cell does not comprise a nucleic acid that encodes the full-length antibody HERCEPTIN® (trastuzumab), the full-length antibody RITUXAN® (rituximab), or the full-length antibody BIIB. In some embodiments, the host cell does not express a the full-length antibody HERCEPTIN® (trastuzumab), the full-length antibody RITUXAN® (rituximab), or the full-length antibody BIIB.

In some embodiments, a host cell with reduced NHEJ activity is a cell that has a disruption in a gene locus that is involved in NHEJ activity of the cell (i.e., a disruption in one or more genes that encode proteins that drives the NHEJ pathway or contribute to NHEJ Examples of NHEJ pathway genes for *Pichia* include, but are not limited to, YKU70, YKU 80, DNL4, Rad50, Rad 27, MRE11, and POL4. The names of genes may be different for different host cells. Suitable NHEJ pathway genes for disruption can be found in, e.g., KEGG Non-homologous end-joining pathway at http://www.genome.jp/kegg-bin/show_pathway?map=ko03450&show description=show. In some embodiments, the host cell with reduced NHEJ activity is a yeast cell, for example, a *Pichia* cell, with a disruption in the YKU70 gene locus, such that NHEJ activity is reduced in the cell. In some cases, the YKU70 gene locus is disrupted by inserting or integrating a nucleic acid encoding an RNA-guided endonuclease in the YKU70 gene locus. The reduction in NHEJ activity can be a reduction of NHEJ events in the host cell, for example, a reduction of at least 20%, 30%, 40%, 50%, 60%, 70%, 80%, 90%, 100% or any percent reduction in between these percentages, as compared to a host cell that does not have a disruption in a gene controlling NHEJ in the cell, for example, a yeast cell with a disruption in the YKU70 gene locus of a *Pichia* s cell.

In some embodiments, the RNA-guided DNA endonuclease is provided by introducing a nucleic acid encoding the endonuclease into the host cell. For example, a plasmid or vector comprising a nucleic acid encoding the RNA-guided DNA endonuclease can be introduced into the cell. In some embodiments, the plasmid can further comprise a nucleic acid sequence encoding a selectable marker for maintenance of the plasmid in the host cell. In some embodiments the nucleic acid encoding the endonuclease further comprises a promoter sequence. In some embodiments, the nucleic acid encoding the RNA-guided DNA endonuclease is integrated into genome of the host cell. In certain embodiments, the RNA-guided DNA endonuclease, for example, Cas9, is integrated into the YKU70 gene of a yeast cell, thereby reducing NHEJ activity in the yeast cell. In some embodiments, the nucleic acid encoding the RNA-guided DNA endonuclease is under the control of a constitutive promoter. In specific embodiments, the nucleic acid encoding the RNA-guided DNA endonuclease is under the control of a medium-strength *Pichia* pPGK1 promoter. Examples of suitable promoters include, but are not limited to, pYPT1, pTEF1, pSSA3, pGPM1, pENO1. In some embodiments, the RNA-guided DNA endonuclease can be introduced into the host cell prior to, simultaneously with, or after introduction of the first and second linear nucleic acids. In other embodiments, the RNA-guided DNA endonuclease can be introduced into the host cell prior to, simultaneously with, or after introduction of the first linear nucleic acids, the second linear nucleic acid and the donor DNA molecule. In some embodiments, an RNA encoding the RNA-guided DNA endonuclease can be introduced into the host cell. In other embodiments, the RNA-guided DNA endonuclease protein or a functional fragment thereof can be introduced into the host cell.

In some embodiments, the first linear nucleic acid comprises two internal homologous sequences that are capable of homologously recombining with each other, whereby homologous recombination of the internal homologous sequences results in formation of the circular extrachromosomal nucleic acid expressing the selectable marker. In some embodiments, the first linear nucleic acid is capable of recombining with the second linear nucleic acid. In some embodiments, the first linear nucleic acid comprises a selectable marker, such that, after introduction of the first and second linear nucleic acids, the first and second linear nucleic acids undergo homologous recombination to form a circular, episomal or extrachromosomal nucleic acid comprising the coding sequence for the selectable marker and the guide RNA, for example, via, gap repair. Once circularized, the extrachromosomal nucleic acid includes a coding sequence for a selectable marker, and suitable regulatory sequences such as a promoter and/or a terminator that enables expression of the marker in the host cell. Providing the selectable marker on a circular, extrachromosomal nucleic acid, allows marker-less integration of one or more donor DNA molecules into a host cell genome, while avoiding the integration of extraneous sequences (i.e., a selectable marker) into the genome and any deleterious effects associated with prolonged marker expression. See, for example, U.S. Pat. No. 9,476,065 for gap repair mechanisms that can be used in the methods described herein.

Subsequent to formation of the extrachromosomal nucleic acid comprising the coding sequence for the selectable marker and the guide RNA, the guide RNA is transcribed from the extrachromosomal nucleic acid and guides the RNA-guided DNA endonuclease expressed in the host cell to a target site in the genome of the host cell, where the endonuclease creates a break at the target site. In some embodiments, once the endonuclease creates a break at the target site, the donor DNA molecule is integrated into the host cell genome via homologous recombination.

In some embodiments, the method comprises integrating a plurality (i.e., two or more) donor DNA molecules into a plurality of target sites of the host cell genome. In some embodiments, the host cell is contacted with a first linear nucleic acid and two or more second linear nucleic acid molecules, wherein each second linear nucleic acid molecule comprises a nucleic acid encoding a different guide RNA which targets a different site in the host cell genome. Each different second linear nucleic acid can recombine with the first linear nucleic acid to form two or more different, circular, extrachromosomal nucleic acids in the host cell. It is understood that the term "first linear nucleic acid" and "second linear nucleic acid" includes multiple copies of the same nucleic acid molecule. For example, the host cell can be contacted with two or more second linear nucleic acid molecules, wherein each second linear nucleic acid molecule comprises a nucleic acid encoding a different guide RNA to target two, three, four, five, six, seven or more different sites in the host cell genome. In some embodiments, once the guide RNA guides the RNA-guided endonuclease to two or more target sites, the endonuclease creates a break at the two or more target sites and two or more donor DNA molecules are integrated into the host cell genome via homologous recombination.

In some embodiments, the circular extrachromosomal nucleic acid comprises the coding sequence for the selectable marker and a guide RNA cassette comprising, from 5' to 3', the RNA polymerase II promoter, the first nucleic acid encoding a first ribozyme, the nucleic acid encoding a guide RNA, the second nucleic acid encoding a second ribozyme, and the terminator.

Examples of promoters that can be used in any of the methods provided herein to control expression of a guide RNA include, but are not limited to, a *Pichia* Pol II promoter (pHTA1), *Saccharomyces* promoter pPGK1, *Saccharomyces* promoter pTDH3, and *Saccharomyces* promoter pACT1. In some embodiments, the promoter, for example, an RNA polymerase II promoter, is from the same species as the host cell. In other embodiments, the promoter, for example, an RNA polymerase II promoter, is from a different species than the host cell.

By flanking the guide RNA with a first and second ribozyme, upon transcription of the gRNA cassette, under the control of the RNA polymerase II promoter, the ribozymes self-cleave the transcript to produce the desired guide RNA sequence. See, for example, Gao and Zhao (*J. Integr. Plant Biol.* 56(4): 343-349 (2014)). In some embodiments, the guide RNA is flanked by a hammerhead (HH) and hepatitis delta virus (HDV) ribozyme sequences. In specific embodiments, one or both of the ribozymes are flanked by linker sequences to facilitate release of the guide RNA after cleavage. In some embodiments, the linker sequence is at least 5, 6, 7, or 8 nucleotides in length. Exemplary linker sequences are provided in the Examples.

In some embodiments, the first linear nucleic acid comprising a selectable marker is a gapped vector comprising a pair of homologous flanking sequences that recombine with a pair of homologous sequences flanking the gRNA cassette in the second linear nucleic acid to form a larger circular vector where the gap has been repaired by inserting the second linear nucleic acid into the gapped vector. In some embodiments each homologous flanking sequence of the pair of homologous flanking sequences in the first nucleic acid contains a recombination region comprising a nucleotide sequence of sufficient length and sequence identity that allows for homologous recombination with the pair of homologous flanking sequences in the second linear nucleic acid, but not with other regions of the first or second linear nucleic acid participating in the in vivo assembly, nor with any genomic regions of the host cell. For in vivo assembly of marker/gRNA vectors via gap repair and for selection of cells capable of homologous recombination and gap repair, see, for example, Horwitz et al. (*Cell Systems* 1:88-96 (2015)) and International Application Publication No. WO2015/095804, both of which are incorporated herein in their entireties by this reference.

In some embodiments, "sufficient sequence identity" refers to sequences with at least 70%, at least 75%>, at least 80%>, at least 85%>, at least 90%>, at least 95%>, at least 99%>, or 100%, identity between recombination regions, over a length of, for example, at least 15 base pairs, at least 20 base pairs, at least 50 base pairs, at least 100 base pairs, at least 250 base pairs, at least 500 base pairs, or more than 500 base pairs. Those of skill in the art readily understand how to determine the identity of two nucleic acids. For example, the identity can be calculated after aligning the two sequences so that the identity is at its highest level. Another way of calculating identity can be performed by published algorithms. For example, optimal alignment of sequences for comparison can be conducted using the algorithm of Needleman and Wunsch, *J. Mol. Biol.* 48: 443 (1970). For a discussion of effective lengths of homology between recombination regions, see Hasty et al. (*Mol Cell Biol* 11:5586-91 (1991)).

Using the methods provided herein, one or more target sites in a host cell genome can be modified with surprisingly high efficiency compared to conventional CRISPR/Cas systems. The efficiency of alteration in a population of cells can be at least about 5%, 10%, 15%, 20%, 25%, 30%, 35%, 40%, 45%, 50%, 55%, 60%, 65%, 70%, 75% 80%, 85%, 90%, 95%, or higher, or any percentage in between these percentages.

In some embodiments, the methods of the invention provide for markerless recovery of a transformed host cell comprising a successfully integrated donor nucleic acid. Such a cell occurs within a frequency of about one every 1000, 900, 800, 700, 600, 500, 400, 300, 200 or 100 contacted host cells, or clonal populations thereof, screened. In particular embodiments, markerless recovery of a transformed host cell comprising a successfully integrated donor nucleic acid occurs within a frequency of about one every 90, 80, 70, 60, 50, 40, 30, 20, or 10 contacted host cells, or clonal populations thereof, screened. In more particular embodiments, markerless recovery of a transformed cell comprising a successfully integrated donor nucleic acid occurs within a frequency of about one every 9, 8, 7, 6, 5, 4, 3, or 2 contacted host cells, or clonal populations thereof, screened.

In certain embodiments, markerless recovery of a transformed cell comprising a successfully integrated donor nucleic acid at a single locus occurs within a frequency of at least 10%, 20%, 30%, 50%, 60%, 70%, 80%, 90%, or 100% of contacted host cells or clonal population thereof, screened. In certain embodiments, markerless recovery of a transformed cell comprising successfully integrated donor nucleic acids at two, three, four, or five loci occurs at least 10%, 20%, 30%, 40%, 50%, 60%, 70%, 80%, 90%, or 100% of contacted host cells or clonal population thereof, screened. In certain embodiments, any suitable number of donor nucleic acids (e.g., n=1 to 20) can be successfully integrated at n loci in the host cell genome.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof. Phenotypic readouts, for example, a predicted gain or loss of function, can also be used as a proxy for effecting the intended genomic modification(s).

Cell Culture

In some embodiments of the methods described herein, host cells are cultured for a period of time sufficient for expression of the selectable marker from the circularized extrachromosomal vector. In some embodiments where the selectable marker is a drug resistance marker, the culturing is carried out for a period of time sufficient to produce an amount of the marker protein that can support the survival of cells expressing the marker in selectable media. In certain embodiments, these conditions also select against the survival of cells not expressing the selectable marker. Selective pressure can be applied to cells using a variety of compounds or treatments that would be known to one of skill in the art. For example, selective pressure can be applied by exposing host cells to conditions that are suboptimal for or deleterious to growth, progression of the cell cycle or viability, such that cells that are tolerant or resistant to these conditions are selected for compared to cells that are not tolerant or resistant to these conditions. Conditions that can be used to exert or apply selective pressure include, but are not limited to, antibiotics, drugs, mutagens, compounds that slow or halt cell growth or the synthesis of biological building blocks, compounds that disrupt RNA, DNA or protein synthesis, deprivation or limitation of nutrients, amino acids, carbohydrates or compounds required for cell growth and viability from cell growth or culture media, treatments such as growth or maintenance of cells under conditions that are suboptimal for cell growth, for instance at suboptimal temperatures, atmospheric conditions (e.g., % carbon dioxide, oxygen or nitrogen or humidity) or in deprived media conditions. The level of selective pressure that is used can be determined by one of skill in the art. This can be done, for example, by performing a kill curve experiment, where control cells and cells that comprise resistance markers or genes are tested with increasing levels, doses, concentrations or treatments of the selective pressure and the ranges that selected against the negative cells only or preferentially over a desired range of time (e.g., from 1 to 24 hours, 1 to 3 days, 3 to 5 days, 4 to 7 days, 5 to 14 days, 1 to 3 weeks, 2 to 6 weeks). The exact levels, concentrations, doses, or treatments of selective pressure that can be used depends on the cells that are used, the desired properties themselves, the markers, factors or genes that confer resistance or tolerance to the selective pressure as well as the levels of the desired properties that are desired in the cells that are selected and one of skill in the art would readily appreciate how to determine appropriate ranges based on these considerations.

The culturing can be performed in a suitable culture medium in a suitable container, including but not limited to a cell culture plate, a flask, or a fermentor. In some embodiments, the culture medium is an aqueous medium comprising assimilable carbon, nitrogen and phosphate sources. Such a medium can also include appropriate salts, minerals, metals and other nutrients. In some embodiments, in addition to the selection agent, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter). Materials and methods for the maintenance and growth of cell cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process. In some embodiments, the culturing is carried out for a period of time sufficient for the transformed population to undergo a plurality of doublings until a desired cell density is reached. In some embodiments, the culturing is carried out for a period of time sufficient for the host cell population to reach a cell density ($OD_{600}$) of between 0.01 and 400 in the fermentation vessel or container in which the culturing is being carried out. In other embodiments, the culturing is carried for a period of at least 12, 24, 36, 48, 60, 72, 84, 96 or more than 96 hours. In some embodiments, the culturing is carried out for a period of between 3 and 20 days. In some embodiments, the culturing is carried out for a period of 1, 2, 3, 4, 5, 6, 7, 8, 9, 10, 11, 12, 13, 14, 15, 16, 17, 18, 19, 20 or more than 20 days.

In some embodiments of the methods described herein, the methods further comprise the step of eliminating the circularized extrachromosomal vector from the host cell, for example, once a selected host cell has been identified as comprising the desired genomic integration(s). Plasmid-based systems generally require selective pressure on the plasmids to maintain the foreign DNA in the cell. In some embodiments, elimination of a plasmid encoding the selective marker from a selected cell can be achieved by allowing the selected cells to undergo sufficient mitotic divisions such that the plasmid is effectively diluted from the population. Alternatively, plasmid-free cells can be selected by selecting for the absence of the plasmid, e.g., by selecting against a counter-selectable marker (such as, for example, URA3) or by plating identical colonies on both selective media and non-selective media and then selecting a colony that does not grow on the selective media but does grow on the non-selective media.

In any of the methods described herein, disruption of a target site in a host cell genome occurs when the RNA-guided DNA endonuclease cleaves the target site in the genome of a host cell. The amount of time required for integration of a donor DNA molecule once the RNA-guided DNA endonuclease as cleaved the target site will vary. For example, the period of time encompassed can be at least 6, 12, 24, 36, 48, 60, 72, 96 or more than 96 hours of cell culture, beginning at the point at which the host cell is contacted with the first linear nucleic acid, the second linear nucleic acid and the donor DNA molecule, whether the nucleic acid encoding the RNA-guided DNA endonuclease is integrated into the host cell genome or simultaneously introduced into the host cell with the first linear nucleic acid, the second linear nucleic acid and the donor DNA molecule.

Guide RNAs

As used throughout, a guide RNA (gRNA) sequence is a sequence that interacts with an RNA-guided DNA endonuclease and specifically binds to or hybridizes to a target nucleic acid within the genome of a cell, such that the gRNA and the targeted nuclease co-localize to the target nucleic acid in the genome of the cell. Each gRNA includes a DNA targeting sequence of about 10 to 50 nucleotides in length that specifically binds to or hybridizes to a target DNA sequence in the genome. For example, the DNA targeting sequence is about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. Each gRNA contains a gRNA scaffold sequence that binds to the RNA-guided DNA endonuclease that does not comprise the DNA targeting sequence. In some embodiments, the gRNA comprises a crRNA sequence and a transactivating crRNA (tracrRNA) sequence. In some embodiments, the gRNA does not comprise a tracrRNA sequence.

Generally, the DNA targeting sequence is designed to complement (e.g., perfectly complement) or substantially complement the target DNA sequence. In some cases, the DNA targeting sequence can incorporate wobble or degenerate bases to bind multiple genetic elements. In some cases, the 19 nucleotides at the 3' or 5' end of the binding region are perfectly complementary to the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%).

RNA-Guided DNA Endonucleases

Any RNA-guided DNA endonuclease can be used in the methods provided herein. In some embodiments, the RNA-guided DNA endonuclease is an active Cas9 endonuclease such that when bound to a target nucleic acid as part of a complex with a guide RNA, a double strand break is introduced into the target nucleic acid. In some embodiments, the double strand break is repaired by HDR to insert a donor DNA molecule into the genome of the host cell. Various Cas9 endonucleases can be used in the methods described herein. For example, a Cas9 nuclease that requires an NGG protospacer adjacent motif (PAM) immediately 3' of the region targeted by the guide RNA can be utilized. As another example, Cas9 proteins with orthogonal PAM motif requirements can be used to target sequences that do not have an adjacent NGG PAM sequence. Exemplary Cas9 proteins with orthogonal PAM sequence specificities include, but are not limited to, those described in Esvelt et al. (*Nature Methods* 10: 1116-1121 (2013)).

In some cases, the Cas9 protein is a nickase, such that when bound to target nucleic acid as part of a complex with a guide RNA, a single strand break or nick is introduced into the target nucleic acid. A pair of Cas9 nickases, each bound to a different guide RNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation (See, for example, Ran et al. "Double nicking by RNA-guided CRISPR Cas9 for enhanced genome editing specificity," Cell 154(6): 1380-1389 (2013)).

Host Cells

In another embodiment, provided herein is a modified host cell generated by any of the methods of disrupting a target site in a host cell genome or genomically integrating one or more exogenous nucleic acids described herein. Populations of modified host cells generated by any of the methods provided herein are also provide. In a specific embodiment, a population of host cells wherein at least 5%, 10%, 15%, 20%, 25%, 30%, 35%, 40%, 45%, 50%, 55%, 60%, 65%, 70%, 75%, 80%, 85%, 90% or higher or any percentage in between are altered using any of the methods provided herein is also provided.

Suitable host cells include any cell in which integration of a donor DNA molecule of interest into target site in the host cell genome is desired. In some embodiments, the host cell is a cell that is capable of performing homologous recombination. In other embodiments, the host cell is a cell that is capable of performing gap repair. In some embodiments, the host cell is a yeast cell. In some embodiments, the yeast cell is a *Pichia* cell. In specific embodiments, the *Pichia* cell is a *Pichia pastoris* cell. In some embodiments, the yeast host cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment. For a list of cell type suitable for integration of one or more donor DNA molecules using the methods described herein, see International Application Publication No. WO2015095804.

Methods of Producing a Protein of Interest

In another embodiment, provided herein are methods of producing a protein of interest. The methods comprising culturing a host cell comprising one or more integrated donor DNA molecules of interest encoding one or more proteins of interest under conditions suitable for production of the protein and recovering the protein produced by the host cell. In some embodiments, the protein of interest is a protein selected from the group consisting of an antibody, an enzyme, a hormone, a growth factor, an anticoagulant, blood factors, an engineered protein, an interferon, an interleukin, a thrombolytic, a viral protein or a bacterial protein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

This example provides results which demonstrate the use of CRISPR for simultaneous deletion and/or integration of one or multiple loci selected from the group consisting of BMT1, BMT2, BMT4, BMT4, PNO1, MNN4-1, MNN4-2, MNN4-3, PRB1, PEP4, AOX1, and DNL4, in *Pichia*. In brief, chimeric gRNAs were generated targeting unique sequences contained in the open reading frame (ORF) of BMT1, BMT2, BMT4, BMT4, PNO1, MNN4-1, MNN4-2, MNN4-3, PRB1, PEP4, AOX1, and DNL4. The gRNAs were transformed in various configurations into host cells expressing the Cas9 protein from the type II bacterial CRISPR system of *Streptococcus pyogenes*. Transformed colonies were screened by colony PCR (cPCR) for the replacement of one or multiple ORFs with a short linker sequence, or HERCEPTIN® antibody sequence.

Materials and Methods

Host Strain

A wild type NRRL Y-48124 *Komagataella pastoris* (*Pichia pastoris*) strain was used in this study. Cas9 was constitutively expressed under a *Pichia* pPGK1 promoter and integrated into the YKU70 locus to disable NHEJ. The resulting strain was Y486. AOX1 was deleted from Y486 resulting in Y651, which was Mut$^s$ on methanol. The anti-Her2 antibody HERCEPTIN® sequence was integrated at the PEP4 locus in Y651 under the control of the pAOX1 promoter. The strain was Y324. Deleting AOX1 and integrating HERCEPTIN® sequence at the PEP4 locus were achieved by targeted integration using CRISPR. The quintuplex engineering was done in the HERCEPTIN® strain background.

Loci Deleted and Guide RNA Sequences

Candidate CRISPR targets inside the targeted ORFs were identified based on the presence of a PAM sequence $N_{(19)}$ NGG. The NGG sequence is referred to as a PAM sequence and the 8 base pairs of DNA proceeding the PAM sequence are especially important for enforcing specificity (See, for example, International Application Publication No. WO2015/095804). The guide RNA sequences are set forth in Table 1.

TABLE 1 guide RNA sequences

| Locus | gRNA sequence (NGG omitted) | SEQ ID NO: |
|---|---|---|
| BMT1/BMT2 | AAAGCTAGAGTTACCGTAA | 1 |
| BMT3 | TCAACTGCAGTCTTGATAA | 2 |
| BMT4 | GTGTGAACAGAGCCATGTA | 3 |
| MNN4-1/PNO1 | ATTTGGAGATTTTGCGCTA | 4 |
| MNN4-2 | TTCTGGAGAGCACTATGAC | 5 |
| MNN4-3 | AACCCTAAGAATCTGGCTC | 6 |

TABLE 1-continued guide RNA sequences

| Locus | gRNA sequence (NGG omitted) | SEQ ID NO: |
|---|---|---|
| PRB1 | TCAACAAGTACTTATATGA | 7 |
| PEP4 | ATTTTATGTCTCAGCAAGA | 8 |
| AOX1 | GACATGGCTCCTATGGTTT | 9 |
| DNL4 | TGGCTGAAATTAGGTAAAG | 10 |
| Upstream of VTH1 | AGAAAATAAAGAGTTTCTA | 11 |
| Upstream of CNE1 | TAGATGCAGTAGGATAGGG | 12 |
| Upstream of ECM10 | GTCCACTAACTACCTTTCG | 13 |
| Upstream of ERO1 | AAAGATAGGGAAAAGGAAA | 14 |

Guide RNA Delivery Modes gRNA Cassette

The guide RNA cassette used in these studies contains an RNA polymerase II promoter pHTA1 from *Pichia* (Weninger et al., 2016), a 19 mer guide RNA sequence, a structural guide RNA sequence, and an ADH1 terminator from *Saccharomyces*. The guide RNA is flanked by hammerhead (HH) and hepatitis delta virus (HDV) ribozyme sequences. The HH ribozyme is also flanked with a short 6 bp linker "TCAGAT" (SEQ ID NO: 15) to facilitate removal of the HH ribozyme (Weninger et al., 2016). Sequences of each element are listed below.

Generation of gRNA Vector for *Pichia*

Standard pRS4XX-series 2p, vectors (Sikorski and Hieter, Genetics 12291): 19-27 (1989)) were used as the starting material. 2µ region was replaced with *Pichia* ARS1 region (See the sequence listing). gRNA expression cassette targeting *Saccharomyces* ADH4 was cloned into the resulting vector between SalI and BamHI. The resulting plasmid is named pAM1114_PPARS1_pHTA1_ScADH4. The primers used in this work is listed in Table 2. The new vector was linearized with EcoRV for gap repair with gRNA cassette in transformation.

TABLE 2

Primers used in generating gRNA delivery components

| Primer name | Description | Sequence |
|---|---|---|
| HJ2299 | Linear pRS4XX REV | CGCGAATGTTCCCCCAGCTTATCTCGACAGGTGGCACTTTTCGGGGAAATG TGCG (SEQ ID NO: 16) |
| HJ2301 | Linear pRS4XX FOR | GACCAAAATAAGTAAATATTAATTGTCGAATACTTTCTAGAGAATAGGAACT TCGG (SEQ ID NO: 17) |
| HJ2300 | *Pichia* ARS1 FOR | CGCACATTTCCCCGAAAAGTGCCACCTGTCGAGATAAGCTGGGGGAACATT CGCG (SEQ ID NO: 18) |
| HJ2302 | *Pichia* ARS1 REV | CCGAAGTTCCTATTCTCTAGAAAGTATTCGACAATTAATATTTACTTATTTTG GTC (SEQ ID NO: 19) |
| HJ2353 | gRNA ScADH4 no tADH1 FOR | CCCCTCGAGGTCGACGGTATC (SEQ ID NO: 25) |
| HJ2357 | gRNA ScADH4 no tADH1 REV | AAAATCATAAATCATAAGAAATTCGCGTCCCATTCGCCATGCCGAAGCATGT TGCC (SEQ ID NO: 20) |
| HJ2358 | tADH1 FOR | GGCAACATGCTTCGGCATGGCGAATGGGACGCGAATTTCTTATGATTTATG ATTTT (SEQ ID NO: 21) |
| HJ2359 | tADH1 REV | CTAGAACTAGTGGATCCCCCGGGCGCTGGAGTTAGCATATCTACAATTGGG TG (SEQ ID NO: 22) |

TABLE 2-continued

Primers used in generating gRNA delivery components

| Primer name | Description | Sequence |
|---|---|---|
| HJ2477 | Linear pAM1114_PPARS1_pHTA1_ ScADH4 REV | GGGAGGACTCTCGTTTCCTATG (SEQ ID NO: 23) |
| HJ2442 | Linear pAM1114_PPARS1_pHTA1_ ScADH4 FOR | TTTTAGAGCTAGAAATAGCAAG (SEQ ID NO: 24) |

FOR = a forward primer; REV = a reverse primer

Generation of Linear gRNAs for Targeted Integrations
Targeted PEP4 Deletion
Stitched Linear gRNA Cassette Template pAM1114_PPARS1_pHTA1 ScADH4 plasmid was used in the following PCR reactions. HJ2353 and HJ2463 primers (Table 3) were used to generate the first part of the PEP4 gRNA expression cassette. HJ2455 and HJ2354 primers (Table 3) were used to generate the 2nd part of the PEP4 gRNA expression cassette. The two PCR products were gel extracted and stitched together using PCR. The stitched product was gel extracted and used as linear gRNA cassette in transformations.

Amplification from Cloned gRNA Vector

Two parts of the gRNA cassette were amplified using the same primers as above. The PCR fragments were cleaned and cloned into pAM1114_PPARS1_pHTA1 ScADH4 (generated using the method described above) in *Saccharomyces* according to methods described in U.S. Pat. Nos. 8,110,360, 8,221,982, and 8,332,160. Plasmid was extracted from yeast and transformed into *E. coli*. Clones were sequence verified. The linear gRNA fragment was amplified from the clones using HJ2353 and HJ2354 primers (Table 3). The PCR product was gel extracted or cleaned using the Zymo DNA Clean & Concentrator™ kit (Zymo Research (Irvine, CA).

TABLE 3

Primers for PEP4 gRNAs

| Primer name | Description | Sequence |
|---|---|---|
| HJ2353 | 1$^{st}$ part gRNA FOR | CCCCTCGAGGTCGACGGTATC (SEQ ID NO: 25) |
| HJ2463 | 1$^{st}$ part gRNA REV | TCTTGCTGAGACATAAAATCATCTGAGACGAGCTTACTCGTTTCGTCCTCAC (SEQ ID NO: 26) |
| HJ2455 | 2$^{nd}$ part gRNA FOR | ATTTTATGTCTCAGCAAGAGTTTTAGAGCTAGAAATAGCAAGTTAAAATAAG (SEQ ID NO: 27) |
| HJ2354 | 2$^{nd}$ part gRNA REV | CTAGAACTAGTGGATCCCCCG (SEQ ID NO: 28) |

Generation of Linear Donor DNA

Linear donor DNAs comprise about 1 kb upstream and downstream homology regions targeting each ORF, flanking a central linker (CGCTCGTCCAACGCCGGCGGACCT), (SEQ ID NO: 29) and were generated by the methods of polynucleotide assembly described in U.S. Pat. No. 8,221, 982. Donor DNA sequences for integration into the loci listed in the above are listed in the sequence listing.

Simultaneous Deletion of ORF and Integration of a Short Linker Sequence Using CRISPR For each loci or ORF of interest, a linear donor DNA, a linear gRNA, and a linear gRNA vector backbone (~200 ng each) were co-transformed into each Cas9 expressing strain using an electroporation method (See, *Pichia* Protocols, Chapter 3, by D. R. Higgins and J. Cregg, eds. In Methods in Molecular Biology, vol. 103, The Humana Press, Totowa, NJ, 1998). Cells were recovered overnight before plating to selective, antibiotic-containing (nourseothricin, 50 mg/L) media to maintain the gRNA or marker plasmid. Marker-less integrations were scored as positive if colony PCR (cPCR) using primers binding upstream of the 5' integration flank and to the integrated linker sequence (Table 4) produced the correct amplicon, a result indicative of a targeted integration event. The 3' integration and disappearance of open reading frame (ORF) sequences were also checked with cPCR.

TABLE 4

Primer sequences for confirming integration into ORFs

| Primer name | Description | Sequence | SEQ ID NO: |
|---|---|---|---|
| HJ2338 | AOX1 locus US FOR | TAACAGTTATTATTCGAGATCTA | 30 |
| HJ2674 | DNL4 locus US FOR | GGTACCATACTTCTCCACCG | 31 |
| HJ2417 | PEP4 locus US FOR | TTCGAAACTGCAGCTAGCAA | 32 |
| HJ2425 | BMT1/BMT2 locus US FOR | CCATTGTTGCCGATAACTGTTG | 33 |
| HJ2575 | BMT3 locus US FOR | CGGTATCGCTGCTTTCTTTA | 34 |
| HJ2581 | BMT4 locus US FOR | CAATAATCAATGCAGCCCAG | 35 |
| HJ2605 | MNN4-1/PNO1 locus US FOR | GAAAAGGGTAGTGAAAGGAAAG | 36 |
| HJ2593 | MNN4-2 locus US FOR | GCTAATTACGTACCAGAACC | 37 |
| HJ2411 | MNN4-3 locus US FOR | TTGACACCTTGGATAAAAGGG | 38 |
| HJ2599 | PRB1 locus US FOR | CAGAATAACTTCATGACTGC | 39 |
| HJ2794 | VTH1 locus US FOR | AGTGACGCCAACAATACCCATGA | 40 |
| HJ2778 | CNE1 locus US FOR | TTGTCCCACTTTGAATAATCG | 41 |
| HJ2862 | ECM10 locus US FOR | GGAGTTTTTTGGGCTAGGGGTTTG | 42 |
| HJ2782 | ERO1 locus US FOR | GCTGAGCACTTCAGTCTTACG | 43 |

"US" = upstream; "FOR" = a forward primer

Results

Up to 100% targeting efficiency was obtained from single, double, and triple integrations. Very high efficiencies were achieved from quadruple (47%) and quintuple (31%) integrations (see Table 5 below). This is a great improvement from the currently known *Pichia* CRISPR technology.

As shown in Table 5, using the methods provided herein, high efficiency, targeted and marker-less single, double, triple, quadruple, and quintuple integrations in a host cell genome were achieved by using CRISPR in host cells, including *Pichia*. To summarize, in this example, one or more targeted integrations were achieved by transforming host cells (e.g., *Pichia* cells) containing a nucleic acid encoding Cas9 under the control of a medium strength promoter pPGK1 from *Pichia* with linear Nat-marked vector backbone, guide RNAs under a constitutive promoter, and donor DNAs. The guide RNA cassette contains an RNA polymerase II promoter pHTA1 from *Pichia*, a 19mer guide RNA sequence specific for a gene or loci of interest, a structural guide RNA sequence that binds to Cas9, and an ADH1 terminator from *Saccharomyces*. The guide RNA is flanked by hammerhead (HH) and hepatitis delta virus (HDV) ribozyme sequences. The HH ribozyme is also flanked with a short 6 bp linker (TCAGAT) (SEQ ID NO: 15) to facilitate releasing of the gRNA.

TABLE 5

Summary of CRISPR targeting efficiency

| Starting Host strain | Targeting loci and integration | MS# | Multiplexing | Efficiency |
|---|---|---|---|---|
| Y486 | AOX1 deletion resulting in Y651 | MS530 | Single | 90% |
| Y486 | DNL4 deletion | | Single | 100% |
| Y486 | PEP4 deletion | | Single | 100% |
| Y551 | PEP4 deletion with HERCEPTIN ® integration at PEP4 resulting in Y324 | MS841 | Single | 100% |
| Y324 | BMT1/BMT2/BMT3 deletion | MS061, MS648 | Double | 100% |
| Y324 | MNN4-1/PNO1/MNN4-2 deletion resulting in Y136 | MS056, MS652 | Double | 100% |
| Y324 | BMT1/BMT2/BMT3/BMT4 deletion | MS061, MS648, MS649 | Triple | 73% |
| Y324 | MNN4-1/PNO1/MNN4-2/MNN4-3 deletion | MS056, MS652, MS653 | Triple | 100% |
| Y136 | BMT1/BMT2/BMT3 deletion | MS061, MS648 | Double | 100% |
| Y136 | PRB1/MNN4-3 deletion | MS655, MS653 | Double | 100% |
| Y136 | BMT1/BMT2/BMT3/BMT4 deletion | MS061, MS648, MS649 | Triple | 100% |
| Y136 | BMT1/BMT2/BMT3/MNN4-3 deletion | MS061, MS648, MS653 | Triple | 100% |

TABLE 5-continued

Summary of CRISPR targeting efficiency

| Starting Host strain | Targeting loci and integration | MS# | Multiplexing | Efficiency |
|---|---|---|---|---|
| Y136 | BMT1/BMT2/BMT3/MNN4-3/PRB1 deletion | MS061, MS648, MS653, MS655 | Quadruple | 47% |
| Y136 | BMT1/BMT2/BMT3/BMT4/MNN4-3/PRB1 deletion | MS061, MS648, MS649, MS653, MS655 | Quintuple | 31% |
| Y324 | pTDH3 > VTH1/pTDH3 > CNE1/pTDH3 > ECM10/pTDH3 > ERO1 | MS637, MS628, MS766, MS632 | Quadruple | 20% |

Using the methods provided herein, high efficiency, targeted and marker-less single, double, triple, quadruple, and quintuple integrations in a host cell genome were achieved by using CRISPR in host cells, including *Pichia*. This was achieved by transforming host cells (e.g., *Pichia* cells) containing a nucleic acid encoding Cas9 under the control of a medium strength promoter pPGK1 from *Pichia* with linear Nat-marked vector backbone, guide RNAs under a constitutive promoter, and donor DNAs. The guide RNA cassette contains an RNA polymerase II promoter pHTA1 from *Pichia* (Weninger et al., 2016), a 19mer guide RNA sequence, a structural guide RNA sequence, and ADH1 terminator from *Saccharomyces*. The guide RNA is flanked by hammerhead (HH) and hepatitis delta virus (HDV) ribozyme sequences. The HH ribozyme is also flanked with a short 6 bp linker "TCAGAT" (SEQ ID NO: 15) to facilitate releasing of the gRNA (Weninger et al., 2016).

Production of Antibodies
Construction of Antibody Expression Cassettes

The BIIB antibody sequences include heavy chain (HC) and light chain (LC) polypeptides. To drive secretion of the construct from the yeasts, the full length, 89 amino acid pre-pro-alpha factor secretion leader from *Saccharomyces cerevisiae* (Waters et al., 1988, *J. Biol. Chem.* 1988 263(13): 6209-14) was added to the amino termini of both HC and LC. The amino acid sequences of BIIB, HERCEPTIN®, and RITUXAN® were codon-optimized according to host species preference using a codon optimization algorithm, and chemically synthesized by Gen9 (now Ginkgo Bioworks, Boston, MA, USA), Twist (San Francisco, CA, USA), or Integrated DNA technologies (IDT, San Diego, CA, USA). DNA expression constructs were cloned in a variety of configurations under strong constitutive native and/or inducible promoters in each host: as a single 2A peptide linked "operon" (Chng et al., 2015, *MAbs*. 7(2):403-12), as convergent split cassettes at the same locus, or as cassettes at different loci. Various other secretion tags, like those from *S. cerevisiae* pre-pro-alpha factor or invertase, *Pichia* Kar2, or *K. marxianus* inulin were also tested for their ability to direct antibody secretion in yeasts.

DNA Assembly and Transformations

Multi-component DNA constructs were generated using DNA assembly methods as previously described (De Kok et al. (2014) *ACS Synth. Biol.* 21; 3(2):97-106. doi: 10.1021/sb4001992; Serber et al., U.S. Pat. No. 8,221,982), and transformed into each host using methods described below.

For *Pichia pastoris* host cells, linear fragments of donor DNA cassettes containing ~1.0 kb of upstream and downstream homology of targeting loci to *Pichia* genome, guide RNA (gRNA), and vector containing *Pichia* ARS1 sequence and homology regions with gRNA were transformed into *Pichia* host strains expressing Cas9 (Weninger et al., *J. Biotech.* 235:139-149 (2016); Horwitz et al. *Cell Syst.* July 29; 1(1):88-96 (2015)). The transformation protocol was adapted from Higgins and Cregg's electroporation method (Higgins and Cregg, *Methods Mol Biol.* 103:1-15 (1998)).

Media and Strain Cultivation

Production of antibodies from four yeast hosts was conducted in cultures in 96-well microtiter plates (1.1 or 2.2 mL) at 1,000 rpm shaking with 80% relative humidity in the media described below. Cells were typically grown for 1-2 days (pre-culture phase) before being diluted or spun down and resuspended in fresh media, and re-grown for 2-3 days (production phase). Cells were separated by centrifugation and supernatant samples were collected for future analyses. To produce large volume of cultures, cells were grown in 50 mL of media in 250 mL of flasks and shaken at 200 rpm. Culturing conditions for each species are listed below.

Protein A Purification

Supernatant samples from antibody production cultures were purified and concentrated using Protein A tip columns (PhyNexus, San Jose, CA, USA).

Semi-Quantitative Antibody Titer Measurement by Dot Blot

Dot blot analysis was carried out using the Minifold I 96-Well System (GE Healthcare, Little Chalfont, UK) according to the manufacturer protocol. Supernatants were collected from cultures grown under production conditions. Detection was performed using IRDye® 800CW goat anti-human IgG (H+L) antibody (LI-COR, Lincoln, NE, USA) as both the primary and secondary antibody and imaged on the Odyssey Infrared Imaging System (LI-COR, Lincoln, NE, USA).

EndoH Treatment

Endoglycosidases treatment was done using Endo $H_f$ (New England Biolabs, Cat. No. P0703S) according to the manufacturer's instructions. For non-reducing samples, 1× Glycoprotein Denaturing Buffer was replaced with 5% SDS solution.

Western Blot

All monoclonal antibody samples were mixed with NuPAGE LDS Sample Buffer (Thermofisher, Cat. No. NP008) and denatured at 70° C. for 10 min before running non-reduced samples on 3-8% Tris-Acetate precast protein gels (Thermofisher, Cat. No. EA0375). For reduced samples, NuPAGE Sample reducing Buffer (Thermofisher, Cat. No. NP009) was used as reducing agent. Reduced samples were denatured at 70° C. for 10 minutes and then run on 4-12% Bis-Tris precast protein gels (Thermofisher, Cat. No. NP0321). For investigation BIIB degradation by intracellular cell lysate, samples were run on a 48-well E-PAGE gel using the iBlot system (Thermofisher). For Western Blot analysis, Goat anti-human IgG (H+L) (LiCor, Cat. No. 925-32232) was used at a 1:10,000 dilution to detect heavy chain, light chain or full length antibody.

P. pastoris. Pichia colonies were inoculated in 360 μL of BMGY 1% glycerol (2% Bacto peptone, 1% Bacto yeast extract, 100 mM potassium phosphate pH 6.0, 1.34% yeast nitrogen base without amino acids, 0.4 μg/mL Biotin, and 1% Glycerol) and grown in 1.1 mL 96-well plates for 24 hours at 30° C. Cells were then spun down and resuspended in 360 μL BMMY (2% Bacto peptone, 1% Bacto yeast extract, 100 mM potassium phosphate, pH 6.0, 1.34% yeast nitrogen base without amino acids, 0.4 μg/mL Biotin, 0.5% v/v methanol) and grown at 30° C. for 72 hours. 1% v/v methanol was added to production plates after 24 and 48 hours in BMMY.

We cloned expression constructs for HERCEPTIN® and RITUXAN® for *Pichia*. Constructs were designed as convergent, split expression cassettes using the shorter pre-alpha leader in place of the pre-pro-alpha leader previously used. We chose this shorter leader to match constructs used in successful published efforts (Zha, 2013), though the longer leader has also been used successfully as well (Kozlov and Yagudin, 2008). We have also used the same secretion tag Kar2 for RITUXAN® as published by Glycofi (Li et al., 2006) in *Pichia*. All sequences were codon optimized for each host using codon optimization algorithms. Using these new constructs, we were able to detect full-length IgG expression in *Pichia*.

We also cloned expression constructs for BIIB antibody (CD23 binding antibody) for *Pichia*. The heavy chain (HC) and light chain (LC) sequences of the BIIB antibody can be found in PCT publication WO2009043051 as SEQ ID NO: 18 and SEQ ID NO:4, respectively. However, for this construct, the full-length IgG expression was not detected, although antibody fragments were detected.

Table 6 below provides a summary of *Pichia pastoris* (PP) producing BIIB, HERCEPTIN® and RITUXAN® antibodies in a shake plate. HC/LC, HC and LC sequences are split in two DNA constructs and integrated at the same locus by homology recombination. All BIIB and HERCEPTIN®/RITUXAN® sequences were fused to S. cerevisiae pre-pro-alpha and pre-alpha secretion tag, respectively, unless noted. NA, not available. BDL, below detection limit of Octet.

In some strains, various strain engineering strategies were attempted to increase full-length antibody secretion, e.g., overexpressing genes responsible for protein folding and secretion (CNE1, HAC1, ERO1, KAR2, etc.) or deleting proteases (pep4 and/or prb1). In some instances, the methods described herein were used for simultaneous deletion and/or integration of an antibody construct, one or more overexpression constructs, and/or one or more deletion constructs at multiple loci.

Figure 1B:
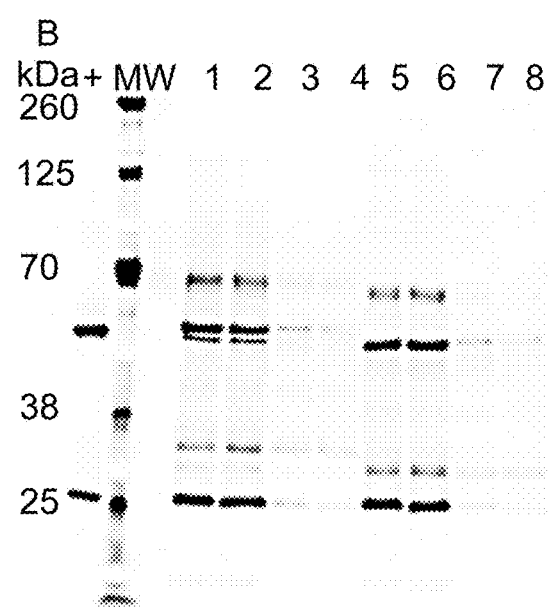

Protease-deleted (pep4Δ) *P. pastoris* strains expressed both HERCEPTIN® and RITUXAN® in full-length (FIGS. 1A and 1B). Under non-reducing conditions, a diffuse 150 kDa+ band matching the standard is observed for both constructs cloned with either the pre-alpha leader, or alternatively, the Kar2 leader (FIG. 1A). In addition, a potential kexin protease site in the LC construct was mutated ("KR to TR"), but had no effect (lanes 2, 4, 6 and 8), and we conclude that LC kexin degradation is not a major factor in *P. pastoris*. Pre-treatment of samples with Endo $H_f$ to remove glycosylation chains (lanes 5-8) sharpens the full-length band. It is clear that HERCEPTIN® titers are much higher than RITUXAN® titers. This is likely due to the different in secretion tags and antibody sequences. When the samples were run under reducing conditions, the proper HC and LC bands are observed (FIG. 1B). Without treatment, a doublet is visible for the HC band, which potentially represents aglycone and glycosylated forms. Endo $H_f$ treatment shifts the higher molecular weight band downward into a single lower molecular weight band, confirming glycosylation (FIG. 1B, Lanes 1 and 2 versus 5 and 6).

FIGS. 1A and 1B illustrate secretion of full-length HERCEPTIN® and RITUXAN® by engineered *P. pastoris* strains. Protein A purified samples were assayed by Western Blot under non-reducing (A) and reducing (B) conditions. 1-4, Protein A purified samples; 5-8, Protein A purified and Endo $H_f$ treated samples. 1 and 5, HERCEPTIN® with pre-alpha secretion leader sequence; 2 and 6, HERCEPTIN® with pre-alpha secretion leader sequence and KR mutated to TR in LC; 3 and 7, RITUXAN® with Kar2 leader sequence; 4 and 8, RITUXAN® with Kar2 sequence and KR mutated to TR in LC. MW, molecular weight marker, with quantities on the left of each gel. +, BIIB antibody standard.

Overexpression constructs of VTH1, CNE1, ECM13, and ERO1 were consolidated in a HERCEPTIN® expressing strain to determine whether they improved antibody expression as they had with the BIIB expressing strains (Table 6). The resulting strain Y676 has shown about 40% higher titer than Y324 (Table 6), which demonstrated that the genetic tricks to improve BIIB expression can also improve HERCEPTIN® expression.

Figure 2:
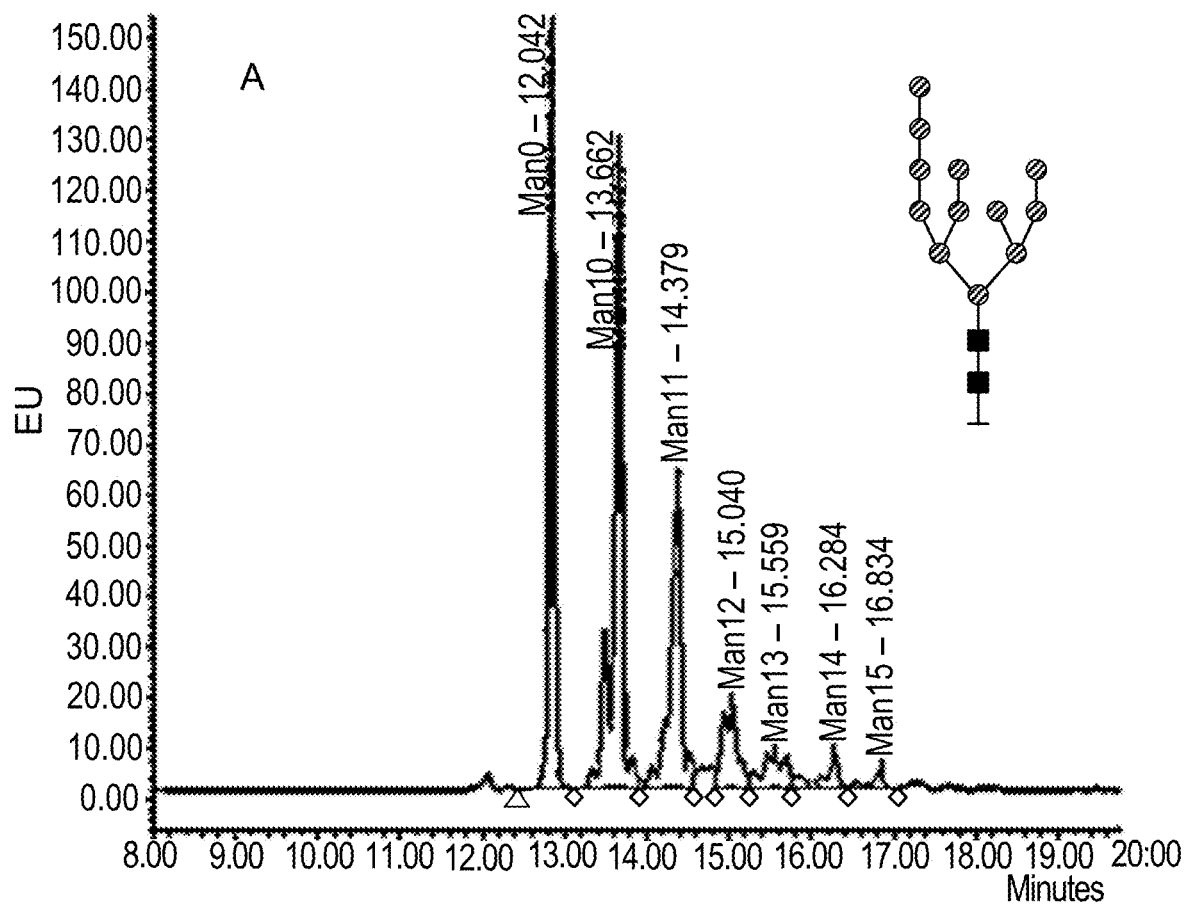
FIG. 2 shows the results of mass spectrometry analysis of samples from HERCEPTIN® producing *P. pastoris*. The samples were analyzed to determine the N-glycan profile of HERCEPTIN® produced by *P. pastoris*. Mass spectrometry results were as expected, with the HERCEPTIN® produced by *P. pastoris* having a glycosylation pattern with high mannose content.

Samples from HERCEPTIN® producing *P. pastoris* was analyzed by mass spectrometer for N-glycan profile. Mass spectrometer result was expected for glycosylation pattern with high mannose in *P. pastoris*. N-Glycan analysis of HERCEPTIN® producing *P. pastoris* is shown in FIG. 2.

The results shown in the Examples section illustrate that *Pichia* is highly engineerable, allowing multiple genomic integration of heterologous nucleic acids simultaneously. Compared to CHO cells which have a doubling time of

TABLE 6

| Species | Antibody | Strain | Engineering | Octet Titer (μg/mL) | Full-length antibody secreted |
|---|---|---|---|---|---|
| PP | None | Y486pp | yku70Δ; Prepared for multiplexing | 0.00 ± 0.00 | No |
| PP | BIIB | Y242 | aox1Δ::pAOX1 > HC_2A_LC, yku70Δ | 5.40 ± 1.14 | No |
| PP | BIIB | Y800 | aox1Δ::pAOX1 > HC_2A_LC, yku70Δ, dnl4Δ | 5.56 ± 0.98 | No |
| PP | BIIB | Y126 | aox1Δ::pAOX1 > HC_2A_LC; yku70Δ, dnl4Δ, pTDH3 > VTH1 | 9.77 ± 0.41 | No |
| PP | BIIB | Y829 | aox1Δ::pAOX1 > HC_2A_LC; dnl4Δ, pTDH3 > VTH1 pTDH3 > CNE1, pTDH3 > ECM10, pTDH3 > ERO1 | 11.17 ± 0.06 | No |
| PP | HERCEPTIN® | Y324 | pep4Δ::pAOX1 > HC/LC, aox1Δ, yku70Δ | 8.67 ± 0.68 | Yes |
| PP | HERCEPTIN® | Y676 | pep4Δ::pAOX1 > HC/LC, aox1Δ, yku70Δ, pTDH3 > CNE1, pTDH3 > ECM10, pTDH3 > ERO1, pTDH3 > VTH1 | 11.95 ± 0.84 | Yes |
| PP | RITUXAN® | Y328 | pep4Δ::pAOX1 > HC/LC, yku70Δ | BDL | Yes | about 19-24 hours and a total genetic engineering cycling time (from one transformation to the next transformation) of about three months, *Pichia* has a cell population doubling time of about 2 hours and a total cycling time of about two weeks with the compositions and methods provided in the present invention. The compositions and methods provided herein provide a large step forward in our ability to engineer *Pichia* for the production of new biomolecules.

One or more features from any embodiments described herein or in the figures may be combined with one or more features of any other embodiment described herein in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

```
                        INFORMAL SEQUENCE LISTING

ARS1 (SEQ ID NO: 44)
TCGAGATAAGCTGGGGGAACATTCGCGAAAATGAAACAAGTCGGCTGTTATAGTATATTT
ATTATAATATTGAAAGATCTCAAAAGACTACTTATTTTTGAATGAACCAAGTATGAAATC
AACCTATTTGGGGTTGACCAAAATAAGTAAATATTAATTGTCGA pHTA1 (SEQ ID NO: 45)
TGTTGTAGTTTTAATATAGTTTGAGTATGAGATGGAACTCAGAACGAAGGAATTATCACC
AGTTTATATATTCTGAGGAAAGGGTGTGTCCTAAATTGGACAGTCACGATGGCAATAAAC
GCTCAGCCAATCAGAATGCAGGAGCCATAAATTGTTGTATTATTGCTGCAAGATTTATGT
GGGTTCACATTCCACTGAATGGTTTTCACTGTAGAATTGGTGTCCTAGTTGTTATGTTTC
GAGATGTTTTCAAGAAAAACTAAAATGCACAAACTGACCAATAATGTGCCGTCGCGCTTG
GTACAAACGTCAGGATTGCCACCACTTTTTTCGCACTCTGGTACAAAAGTTCGCACTTCC
CACTCGTATGTAACGAAAAACAGAGCAGTCTATCCAGAACGAGACAAATTAGCGCGTACT
GTCCCATTCCATAAGGTATCATAGGAAACGAGAGTCCTCCCCCCATCACGTATATATAAA
CACACTGATATCCCACATCCGCTTGTCACCAAACTAATACATCCAGTTCAAGTTACCTAA
ACAAATCAAA

HH (SEQ ID NO: 46)
TGTTGTAGTTTTAATATAGTTTGAGTATGAGATGGAACTCAGAACGAAGGAATTATCACC
AGTTTATATATTCTGAGGAAAGGGTGTGTCCTAAATTGGACAGTCACGATGGCAATAAAC
GCTCAGCCAATCAGAATGCAGGAGCCATAAATTGTTGTATTATTGCTGCAAGATTTATGT
GGGTTCACATTCCACTGAATGGTTTTCACTGTAGAATTGGTGTCCTAGTTGTTATGTTTC
GAGATGTTTTCAAGAAAAACTAAAATGCACAAACTGACCAATAATGTGCCGTCGCGCTTG
GTACAAACGTCAGGATTGCCACCACTTTTTTCGCACTCTGGTACAAAAGTTCGCACTTCC
CACTCGTATGTAACGAAAAACAGAGCAGTCTATCCAGAACGAGACAAATTAGCGCGTACT
GTCCCATTCCATAAGGTATCATAGGAAACGAGAGTCCTCCCCCCATCACGTATATATAAA
CACACTGATATCCCACATCCGCTTGTCACCAAACTAATACATCCAGTTCAAGTTACCTAA
ACAAATCAAA

HDV (SEQ ID NO: 47)
GGCCGGCATGGTCCCAGCCTCCTCGCTGGCGCCGGCTGGGCAACATGCTTCGGCATGGCG
AATGGGAC 6 bp linker flanking 5' and 3' of HH (reverse complimentary sequence) (SEQ ID NO: 48)
ATCTGA and TCAGAT (SEQ ID NO: 15)

Structural gRNA (SEQ ID NO: 49)
TTTTAGAGCTAGAAATAGCAAGTTAAAATAAGGCTAGTCCGTTATCAACTTGAAAAAGTG
GCACCGAGTCGGTGGTGC tADH1 (SEQ ID NO: 50)
GCGAATTTCTTATGATTTATGATTTTTATTATTAAATAAGTTATAAAAAAAATAAGTGTA
TACAAATTTTAAAGTGACTCTTAGGTTTTAAAACGAAAATTCTTATTCTTGAGTAACTCT
TTCCTGTAGGTCAGGTTGCTTTCTCAGGTATAGCATGAGGTCGCTCTTATTGACCACACC
TCTACCGGCATGCCGAGCAAATGCCTGCAAATCGCTCCCCATTTCACCCAATTGTAGATA
TGCTAACTCCAGC gRNA expression cassette targeting Saccharomyces ADH4 used to construct gRNA vector
backbone for Pichia SEQ ID NO: 51)
TGTTGTAGTTTTAATATAGTTTGAGTATGAGATGGAACTCAGAACGAAGGAATTATCACC
AGTTTATATATTCTGAGGAAAGGGTGTGTCCTAAATTGGACAGTCACGATGGCAATAAAC
GCTCAGCCAATCAGAATGCAGGAGCCATAAATTGTTGTATTATTGCTGCAAGATTTATGT
GGGTTCACATTCCACTGAATGGTTTTCACTGTAGAATTGGTGTCCTAGTTGTTATGTTTC
GAGATGTTTTCAAGAAAAACTAAAATGCACAAACTGACCAATAATGTGCCGTCGCGCTTG
GTACAAACGTCAGGATTGCCACCACTTTTTTCGCACTCTGGTACAAAAGTTCGCACTTCC
CACTCGTATGTAACGAAAAACAGAGCAGTCTATCCAGAACGAGACAAATTAGCGCGTACT
GTCCCATTCCATAAGGTATCATAGGAAACGAGAGTCCTCCCCCCATCACGTATATATAAA
CACACTGATATCCCACATCCGCTTGTCACCAAACTAATACATCCAGTTCAAGTTACCTAA
ACAAATCAAATCTGACTGATGAGTCCGTGAGGACGAAACGAGTAAGCTCGTCTCAGATG
GATTTGATCAATGAAAGCTGTTTTAGAGCTAGAAATAGCAAGTTAAAATAAGGCTAGTCC
GTTATCAACTTGAAAAAGTGGCACCGAGTCGGTGGTGCGGCCGGCATGGTCCCAGCCTCC
TCGCTGGCGCCGGCTGGGCAACATGCTTCGGCATGGCGAATGGGACGCGAATTTCTTATG
ATTTATGATTTTTATTATTAAATAAGTTATAAAAAAAATAAGTGTATACAAATTTTAAAG
```

| INFORMAL SEQUENCE LISTING |
|---|
| TGACTCTTAGGTTTTAAAACGAAAATTCTTATTCTTGAGTAACTCTTTCCTGTAGGTCAG
GTTGCTTTCTCAGGTATAGCATGAGGTCGCTCTTATTGACCACACCTCTACCGGCATGCC
GAGCAAATGCCTGCAAATCGCTCCCCATTTCACCCAATTGTAGATATGCTAACTCCAGC gRNA expression cassette targeting *Saccharomyces* ADH4 excluding tADH1 ordered from IDT
(SEQ ID NO: 52)
CCCCTCGAGGTCGACGGTATCGATTGTTGTAGTTTTAATATAGTTTGAGTATGAGATGGA
ACTCAGAACGAAGGAATTATCACCAGTTTATATATTCTGAGGAAAGGGTGTGTCCTAAAT
TGGACAGTCACGATGGCAATAAACGCTCAGCCAATCAGAATGCAGGAGCCATAAATTGTT
GTATTATTGCTGCAAGATTTATGTGGGTTCACATTCCACTGAATGGTTTTCACTGTAGAA
TTGGTGTCCTAGTTGTTATGTTTCGAGATGTTTTCAAGAAAAACTAAAATGCACAAACTG
ACCAATAATGTGCCGTCGCGCTTGGTACAAACGTCAGGATTGCCACCACTTTTTTCGCAC
TCTGGTACAAAAGTTCGCACTTCCCACTCGTATGTAACGAAAAACAGAGCAGTCTATCCA
GAACGAGACAAATTAGCGCGTACTGTCCCATTCCATAAGGTATCATAGGAAACGAGAGTC
CTCCCCCCATCACGTATATATAAACACACTGATATCCCACATCCGCTTGTCACCAAACTA
ATACATCCAGTTCAAGTTACCTAAACAAATCAAAATCTGACTGATGAGTCCGTGAGGACG
AAACGAGTAAGCTCGTCTCAGATGGATTTGATCAATGAAAGCTGTTTTAGAGCTAGAAAT
AGCAAGTTAAAATAAGGCTAGTCCGTTATCAACTTGAAAAAGTGGCACCGAGTCGGTGGT
GCGGCCGGCATGGTCCCAGCCTCCTCGCTGGCGCCGGCTGGGCAACATGCTTCGGCATGG
CGAATGGGACTTTTTTTGTTTTTTATGTCTGCCCGGGGGATCCACTAGTTCTAG BMT1/BMT2 DELETION MS061 (SEQ ID NO: 53)
GACGGCACGGCCACGCGTTTAAACCGCCAAGATGGTGATTTCCAGCGTTCGAAAAGCCTGTAGTACCCAGAATTT
TGATCAAAGTGTCCTCTTAGCCGTGGCATCCGCGGCTGTCATCTTGATCCTTCTTCGCATGAGCACTTACGTGAT
GCTGATAAGATGGGCACGCCACAACACTAGGGCCAAGACCTCGCCTAGTGGTGGCGACTATCTAAAGGGCTCACC
TAACACCTCTTTAGCGGGGATTGAAGACATTCATACACGAAGTCTGCTGTATGGGTCAGACGAGAAAATGCCGCA
ATCTAAAGAAGAACAAAGGTCCCACAATGCGAATCGTGATGGTGATAAATCATTGGCTCAGGTCAGTAGATTTGA
AATGCATGATAAACGCATATGGTGAGAGCCGTTCTGCACAACTAGATGTTTTCGAGCTTCGCATTGTTTCCTGCA
GCTCGACTATTGAATTAAGATTTCCGGATATCTCCAATCTCACAAAAACTTATGTTGACCACGTGCTTTCCTGAG
GCGAGGTGTTTTATATGCAAGCTGCCAAAAATGGAAAACGAATGGCCATTTTTCGCCCAGGCAAATTATTCGATT
ACTGCTGTCATAAAGACAGTGTTGCAAGGCTCACATTTTTTTTAGGATCCGAGATAAAGTGAATACAGGACAGC
TTATCTCTATATCTTGTACCATTCGTGAATCTTAAGAGTTCGGTTAGGGGGACTCTAGTTGAGGGTTGGCACTCA
CGTATGGCTGGGCGCAGAAATAAAATTCAGGCGCAGCAGCACTTATCGATGCATGCAAGGCGAGAAAAATAAAGA
ACAAAAACACACCTTGCTAAGACCACAACCTTTCAAATTTTGAGATTGTTATTCTTTCATCCTAAAACACCACCG
TCCTATCTCTTGGGAACGTACATATCATTGAGCTTGGTTCATTGATACATCACTGTATCTAACTCTCCTTTTTCG
CTCGTCCAACGCCGGCGGACCTCAAAAAGGATCTAAAAATAAGACAGTAGTGGACTTATATTCATACCATATGAT
GGGTGTTTGCTCACTCGTATGGATCAAAATTCCATGGTTTCTTCTGTACAACTTGTACACTTATTTGGACTTTTC
TAACGGTTTTTCTGGTGATTTGAGAAGTCCTTATTTTGGTGTTCGCAGCTTATCCGTGATTGAACCATCAGAAAT
ACTGCAGCTCGTTATCTAGTTTCAGAATGTGTTGTAGAATACAATCAATTCTGAGTCTAGTTTGGGTGGGTCTTG
GCGACGGGACCGTTATATGCATCTATGCAGTGTTAAGGTACATAGAATGAAAATGTAGGGGTTAATCGAAAGCAT
CGTTAATTTCAGTAGAACGTAGTTCTATTCCCTACCCAAATAATTTGCCAAGAAGTGCTTCGTATCCACATACGCA
GTGGACGTAGCAAATTTCACTTTGGACTGTGACCTCAAGTCGTTATCTTCTACTTGGACATTGATGGTCATTACG
TAATCCACAAAGAATTGGATAGCCTCTCGTTTTATCTAGTGCACAGCCTAATAGCACTTAAGTAAGAGCAATGGA
CAAATTTGCATAGACATTGAGCTAGATACGTAACTCAGATCTTGTTCACTCATGGTGTACTCGAAGTACTGCTGG
AACCGTTACCTCTTATCATTTCGCTACTGGCTCGTGAAACTACTGGATGAAAAAAAAAAGAGCTGAAAGCGAGA
TCATCCCATTTTGTCATCATACAAATTCACGCTTGCAGTTTTGCTTCGTTAACAAGACAAGATGTCTTTATCCGG
TGTTTAAACCCCAGCGCCTGGCGGG BMT3 DELETION MS648 (SEQ ID NO: 54)
GACGGCACGGCCACGCGTTTAAACCGCCGCAGGGTCCCACACAGACCAAATCCAAGTTATTCCCTAAGGGATGGT
TTTCAGAGAGAGAAGAAACTATAATGGTAAACCGGTTGTTGCGGGATGACCCCTCTAAGAGTGATATGCACAATA
GACAGTCTGTTACGCCAAAAGAACTGTGGAAAGTGTTGGGAGACTACGATCTATGGCCTATATACGCATTGGCCA
TGGTATTTTCCATTCCCCAGATACCGATAAAGAGATACCTTACTCTTACTTTGAGGGCATTAGAGTTCACTACCA
CTGAGATCAATCTCTTAACAATCCCTGCTTCGTTTCTGGCGGGAATCATGTCAATTGCTATTTCATTAGTCAGTG
AGTTCTTCAATGAAGGTTTGATTATCGGTATATTGTGTCAATTCTGGTTGCTTATTATGGTTATCATTGAATACA
CCTCTGTGGAAAGATATCTCCCTGGGGACAATATGTGTTGCAACTGTTCGTTGTTGGTGCCCCAGTCCCCCAAC
CGGTACTAATCGGTCTATGTTCCCGTAACTCATATTCGGTTAGAACTAGAACAATAAGTGCATCATTGTTCAACA
TTGTGGTTCAATTGTCGAACATTGCTGGTGCTTATATCTACAGGGAAGACGATAAGCCTTTGTACAAGAGAGGTA
ACAGACAGTTAATTGGTATTTCTTTGGGAGTCGTTGCCCTCTACGTTGTCTCCAAGACATACTACATTCTGAGAA
ACAGATGGAAGACTCAAAAATGGGAGAAGCTTAGTGAAGAAGAGAAAGTTGCCTACTTGGACAGAGCTGAGAAGG
AGAACCTGGGTTCTAAGAGGCTGGACTTTTTGTTCGAGAGTTAAACTGCATAATTTTTTCTAAGTAAATTTCATA
GTTATGAAATTTCTGCAGCTTAGTGTTTACTGCATCGTTTACTGCATCACCCTGTAAATAATGTGAGCTTTTTC
CTTCCATTGCTTGGTATCTTCCTTGCTGCTGTTTCGCTCGTCCAACGCCGGCGGACCTGAGACGGAAACGGAGA
AAGGAGAACGGAGAACGAAGAACGAAGGGAGAGAGAAGCAAAGGGAAGAGCAAGGTATTCTGGAGAGATTAAGAA
AATAGTAGAATAGATTTAACGAAACTGAAACTGAAAGACCGAAAAAAGAATGCAGAAATTAAACACCATAGGGCA
GATTGATTCCGTAATCGGTTTCTTGCTACTATATCTTTCTAGGCTGTCTATAATCCTTTTATAATTTAATCTGCT
AATATCGCTGTCACGATTATTGACATCGACTGTATTTCAACACACAGGTCTTACAGATAGCATGGGGTTTCCAGT
ATTTGATTGACATTTCCGTTTTTGCATAGTCCATAATATAAGGATCAAAAACATGAGATGTCGCAAGGCCTCTTA
AACATGAAATCTCCGTTTACCTTCCGCCATACAACCTTACGCATACAGCAGCTCGGTTTCTACATAGAGTCTTTT
CAAGAACCGGGGTAAAAACCGTTTTACATAGAAAGAGGTAAAACGTTGTGATCATGTGACCGCTGAACATCTCCG
GAACCAACTTCGCGATCTTTTTCGTCTGTCACATACTCAAGGTAAACTAAGTTTCACAACACGAAGGCTCCG
TATCATAAATCCTCAGAGTTGAAGCACTGGCCCCCATCTAATAAATACTCCGAAATGAGTCAAATCCAGTCAAGC
CAAGTGGGGCGAAAAATATGCAAACCGCACAGCCTCAGGCTCAACAAAGACCAATCAATGGGTCTGTGACCCTG
AGCAATGGCCAGAGGATAAACCCTCAGAACTTGACTCCGGTGTTTAAACCCCAGCGCCTGGCGGG BMT4 DELETION MS649 (SEQ ID NO: 55)
GACGGCACGGCCACGCGTTTAAACCGCCCGTTCTGATGGCTTGATGACCGTTGTATTGCCTGTCACTATAGCCAG |

-continued

INFORMAL SEQUENCE LISTING

GGGTAGGGTCCATAAAGGAATCATAGCAGGGAAATTAAAAGGGCATATTGATGCAATCACTCCCAATGGCTCTCT
TGCCATTGAAGTCTCCATATCAGCACTAACTTCCAAGAAGGACCCCTTCAAGTCTGACGTGATAGAGCACGCTTG
CTCTGCCACCTGTAGTCCTCTCAAAACGTCACCTTGTGCATCAGCAAAGACTTTACCTTGCTCCAATACTATGAC
GGAGGCAATTCTGTCAAAATTCTCTCTCAGCAATTCAACCAACTTGAAAGCAAATTGCTGTCTCTTGATGATGGA
GACTTTTTTCCAAGATTGAAATGCAATGTGGGACGACTCAATTGCTTCTTCCAGCTCCTCTTCGGTTGATTGAGG
AACTTTTGAAACCAAAATTGGTCGTTGGGTCATGTACATCAAACCATTCTGTAGATTTAGATTCGACGAAAGC
GTTGTTGATGAAGGAAAAGGTTGGATACGGTTTGTCGGTCTCTTTGGTATGGCCGGTGGGGTATGCAATTGCAGT
AGAAGATAATTGGACAGCCATTGTTGAAGGTAGAGAAAAGGTCAGGGAACTTGGGGGTTATTTATACCATTTTAC
CCCACAAATAACAACTGAAAAGTACCCATTCCATAGTGAGAGGTAACCGACGGAAAAAGACGGGCCCATGTTCTG
GGACCAATAGAACTGTGTAATCCATTGGGACTAATCAACAGACGATTGGCAATATAATGAAATAGTTCGTTGAAA
AGCCACGTCAGCTGTCTTTTCATTAACTTTGGTCGGACACAACATTTTCTACTGTTGTATCTGTCCTACTTTGCT
TATCATCTGCCACAGGGCAAGTGGATTTCCTTCTCGCGGCTGGGTGAAAACGGTTAACGTGAACGCTCGTCCA
ACGCCGGCGGACCTGCCTTGGGGGACTTCAAGTCTTTGCTAGAAACTAGATGAGGTCAGGCCCTCTTATGGTTGT
GTCCCAATTGGGCAATTTCACTCACCTAAAAAGCATGACAATTATTTAGCGAAATAGGTAGTATATTTTCCCTCA
TCTCCCAAGCAGTTTCGTTTTTGCATCCATATCTCTCAAATGAGCAGCTACGACTCATTAGAACCAGAGTCAAGT
AGGGGGTGAGCTCAGTCATCAGCCTTCGTTTCTAAAACGATTGAGTTCTTTTGTTGCTACAGGAAGCGCCCTAGGG
AACTTTCGCACTTTGGAAATAGATTTTGATGACCAAGAGCGGGAGTTGATATTAGAGAGGCTGTCCAAAGTACAT
GGGATCAGGCCGGCCAAATTGATTGGTGTGACTAAACCATTGTGTACTTGGACACTCTATTACAAAAGCGAAGAT
GATTTGAAGTATTACAAGTCCCGAAGTGTTAGAGGATTCTATCGAGCCCAGAATGAAATCATCAACCGTTATCAG
CAGATTGATAAACTCTTGGAAAGCGGTATCCCATTTTCATTATTGAAGAACTACGATAATGAAGATGTGAGAGAC
GGCGACCCTCTGAACGTAGACGAAGAAACAAATCTACTTTTGGGGTACAATAGAGAAAGTGAATCAAGGGAGGTA
TTTGTGGCCATAATACTCAACTCTATCATTAATGTGGTTCTTTTGGTAGCAAAAATCTTTGTTGTTTTGTTCAGT
TCCTCACTCTCATTGATGGCTTCGTTAGTTGACTCCGTGATGGATTTCTTATCTACTTTGATCATATATGTTTCT
AACTCTTTTGCTGGGAAAAGAGACAAGAATGAGTATCCAGTTGGAAGGTCAAGGTTGGAGCCCTTAGGAGTTCTT
GTCTTTTCCGTAATCATAATTGTCTCGGTGTTTAAACCCCAGCGCCTGGCGGG

MNN4-1/PNO1 DELETION MS056 (SEQ ID NO: 56)
GACGGCACGGCCACGCGTTTAAACCGCCAAGGCATATAGGCGAGGGAGAGTTAGCTAGCATACAAGATAATGAAG
GATCAATAGCGGTAGTTAAAGTGCACAAGAAAAGAGCACCTGTTGAGGCTGATGATAAAGCTCCAATTACATTGC
CACAGAGAAACACAGTAACAGAATAGGAGGGGATGCACCACGAGAAGAGCATTCAGTGAACAACTTTGCCAAAT
TCATAACCCCAAGCGCTAATAAGCCAATGTCAAAGTCGGCTACTAACATTAATAGTACAACAACTATCGATTTTC
AACCAGATGTTTGCAAGGACTACAAACAGACAGGTTACTGCGGATATGGTGACACTTGTAAGTTTTTGCACCTGA
GGGATGATTTCAAACAGGGATGGAAATTAGATAGGGAGTGGGAAAATGTCCAAAAGAAGAAGCATAATACTCTCA
AAGGGGTTAAGGAGATCCAAATGTTTAATGAAGATGAGCTCAAAGATATCCCGTTTAAATGCATTATATGCAAAG
GAGATTACAAATCACCCGTGAAAACTTCTTGCAATCATTATTTTTGCGAACAATGTTTCCTGCAACGGTCAAGAA
GAAAACCAAATTGTATTATATGTGGCAGAGACAATTTAGGAGTTGCTTTACCAGCAAAGAAGTTGTCCCAATTTC
TGGCTAAGATACATAATAATGAAAGTAATAAAGTTTAGTAATTGCATTGCGTTGACTATTGATTGCATTGATGTC
GTGTGATACTTTCACCGAAAAAAACACGAAGCGCAATAGGAGCGGTTGCATATTAGTCCCCAAAGCTATTTAAT
TGTGCCTGAAACTGTTTTTTAAGCTCATCAAGCATAATTGTATGCATTGCGACGTAACCAACGTTTAGGCGCAGT
TTAATCATAGCCCACTGCTAAGCCAGAATTCTAATATGTAACTACGTACCTTTCCTTTTAATAAATGATCTGTAT
TTTCCACCTAGTAGCAGATCAAATTGTTCAACTTTAAGTCTTTGGTCCCTCAAGCGAGAGAACTTGCGCGCTCGT
CCAACGCCGGCGGACCTCGGAGGAATGCAAATAATAATCTCCTTAATTTACCCACTGATAAGCTCAAGAGACGCGG
TTTGAAAACGATATAATGAATCATTTGGATTTTATAATAAACCCTGACAGTTTTTCCACTGTATTGTTTTAACAC
TCATTGGAAGCTGTATTGATTCTAAGAAGCTAGAAATCAATACGGCCATACAAAAGATGACATTGAATAAGCACC
GGCTTTTTTGATTAGCATATACCTTAAAGCATGCATTCATGGCTACATAGTTGTTAAAGGGCTTCTTCCATTATC
AGTATAATGAATTACATAATCATGCACTTATATTTGCCCATCTCTGTTCTCTCACTCTTGCCTGGGTATATTCTA
TGAAATTGCGTATAGCGTGTCTCCAGTTGAACCCAAGCTTGGCGAGTTTGAAGAGAATGCTAACCTTGCGTATT
CCTTGCTTCAGGAAACATTCAAGGAGAAACAGGTCAAGAAGCCAAACATTTTGATCCTTCCCGAGTTAGCATTGA
CTGGCTACAATTTTCAAAGCCAGCAGCGGATAGAGCCTTTTTTGGAGGAACAACCAAGGGAGCTAGTACCCAAT
GGGCTCAAAAAGTATCCAAGACGTGGGATTGCTTTACTTTAATAGGATACCCAGAAAAAGTTTAGAGAGCCCTC
CCCGTATTTACAACAGTGCGGTACTTGTATCGCCTCAGGGAAAAGTAATGAACAACTACAGAAAGTCCTTCTTGT
ATGAAGCTGATGAACATTGGGGATGTTCGGAATCTTCTGATGGGTTTCAAACAGTAGATTTATTAATTGAAGGAA
AGACTGTAAAGACATCATTTGGAATTTGCATGGATTTGAATCCTTATAAATTTGAAGCTCCGGTGTTTAAACCCC
AGCGCCTGGCGGG

MNN4-2 DELETION MS652 (SEQ ID NO: 57)
GACGGCACGGCCACGCGTTTAAACCGCCCTGTGGACTCAGGACCAGCTCAGCTTGACAAACCAAGACTTGCACTC
CAATGTGCACAACCCAGTGATTGAGCAGATCGAAACCTCATCAGGAGTCAGATTGTAGTATGGAAAACTTTGTAT
TCTCTATGTACTTAAACACTGGTTTATTTTTTATTGATCGTTATATTGAACAGTTTACACTGGAACATCTTCAG
GGTCGATGTCCTTAATCCAGTGTTGACCAAAGATTGGGATCTTCTCGAAGAAAGTCTTTTGGAACAAAGGCCAGT
TTTCAGTGAAAGTGAAGACGGCAAACAGACCGGCACCTCCCCAGAAAGCCAAAATTGGAAAAGTAGTTTTAATTT
GGGTTGGAGTCAATCCAGCAATTTTCTTGACGGTGGTATACTTGGGACCTTTAACGTACTGAAATGTTAGAACAT
GTTTGTAAAAATCAAATCATCACTGCAGAAACGGTTTGTGTGCCTGCACCGGAGGGTTATCATAATGCCACTTAC
GTTGACCATTTTGGAGGTGTTTGACTAAGTTCAAATATGAATCTCTAAGAAAACTAATAATCAATATGGTGCGAG
CATTGATTGGTTGGACAGCTAGTTTGGAGAAGTACACGACTTAGATGAATCTGCAATAAGGAATAGTCCAATCTG
ATTATGTAAGCTCTCCTTTTGGTTTTCATTTCCATCAGCTCAAGCTTATCATAGCTCAGGTCCCCTCCAGCTTA
TGATGGAATAGGCCATTATTTTTTGCCCTAAAAAGTGGAAGTCCACAAGAAGAAATACAAATACTCAAAATTCAA
AAGTCTTCCTTTGAGTGGATGCAATTTTACGTAGTTTACTGTATGACGTAACTAATGAACCCTTCCGACACAAAG
ATTGAGGTGCCTCACTTAACGTCATTCTTCTATACCCACGAGTGCAACTGACTAGGTCTTATTTTGTTAATTGCC
TCAGTTTCTCCGAACGCTCGTCCAACGCCGGCGGACCTTTATGCATATACTGAAACAACAGAAGGAACTACAGTA
AATTCATAAAAAGCTTAATTCTTACTTTCATCTCGGCACTGTAAATTAACTCAAGTTGGGGCAACATTGTGTGTA
TACTCTTACTGGCATCTTTTCATCTGAAGTCATCTTCTACTACTCTTCTCTTCTGTATGACGTAATCAGCTCGGC
AGCTGTGGCATCGAACAAAAAATGAACAGCCATCCGTCATATCTCATGACTGACTGAGCAAGAACTAAGTCAAC
AGGAAACCTAAAATAAGCTTTCCATTTCTTTTGCGCTGAAGCCAACCACTCCCCACACAGTTGATGAGTGGACGC
AAAACCAGCTCCTATACCTTGACAGAAGAGTCGCCGGAATCAACCTCAACAATTCAGGATATACGAGAGGAAGAC
CAAGTTGCTCCAGGGCCCCAGCAAGAAGCACCTAAACAGTCACATATCCAAAAATGGTTAAGCGATCATCCTAAA
GTATACGCAGTTTTATCTTGGATATGGAAATTTTGGTTGAAACAGTGGTTTCTCATATGTTTGGGCCCTGCGGTT

INFORMAL SEQUENCE LISTING

GCTCTAGCTCATGCATACCCAAATTTTGCCAGACATGATGGAACCATTAGGTCAGAGTATACTATCAACTACGGA
GCCGTAGCTATCATATTCTTCATCTCTGGTCTTACTATGAAAACCAAAGACTTTTTGAAGAACTTTGGACACTGG
AGAGCCCATTTCACAGTGTTAAGCTGCTCGTTTCTACTTACTTCTTCTATCATTTACGGTATAGCGTGCGGTATA
AGAGCTGCTCATGATTCCAATATCGATGACTGGATGTTAGCAGGACTTATTGTTACCGCATGTTGTCCAACCACT
GTGAGCGGTGTTTAAACCCCAGCGCCTGGCGGG

MNN4-3 DELETION MS653 (SEQ ID NO: 58)
GACGGCACGGCCACGCGTTTAAACCGCCGGAGGAGGTGGAACCACCTGTGCAGGCGGTCTGAAAGTGTTCAAGTA
CGGATCTACTACCAAATATACATCTGGTAACCTGAACGGCGTCAGGTTAGTATACTGGAACGAAGGAAAGTTGCA
AAGCTCCAAATTTGTGGTTCGATCCTCTAATTACTCTCAAAAGCTTGGAGGAAACAGCAACGCCGAATCAATTGA
CAACAATGGTGTGGGTTTTGCCTCAGCTGGAGACTCAGGCGCATGGATTCTTTCCAAGCTACAAGATGTTAGGGA
GTACCAGTCATTCACTGAAAAGCTAGGTGAAGCTACGATGAGCATTTTCGATTTCCACGGTCTTAAACAGGAGAC
TTCTACTACAGGGCTTGGGGTAGTTGGTATGATTCATTCTTACGACGGTGAGTTCAAACAGTTTGGTTTGTTCAC
TCCAATGACATCTATTCTACAAAGACTTCAACGAGTGACCAATGTAGAATGGTGTGTAGCGGGTTGCGAAGATGG
GGATGTGGACACTGAAGGAGAACACGAATTGAGTGATTTGGAACAACTGCATATGCATAGTGATTCCGACTAGTC
AGGCAAGAGAGAGCCCTCAAATTTACCTCTCTGCCCCTCCTCACTCCTTTTGGTACGCATAATTGCAGTATAAAG
AACTTGCTGCCAGCCAGTAATCTTATTTCATACGCAGTTCTATATAGCACATAATCTTGCTTGTATGTATGAAAT
TTACCGCGTTTTAGTTGAAATTGTTTATGTTGTGTGCCTTGCATGAAATCTCTCGTTAGCCCTATCCTTACATTT
AACTGGTCTCAAAACCTCTACCAATTCCATTGCTGTACAACAATATGAGGCGGCATTACTGTAGGGTTGGAAAAA
AATTGTCATTCCAGCTAGAGATCACACGACTTCATCACGCTTATTGCTCCTCATTGCTAAATCATTTACTCTTGA
CTTCGACCCAGAAAAGTTCGCCCGCTCGTCCAACGCCGGCGGACCTATAGTTGTTTTTTCTATATAAAACGAAAC
GTTATCATCTTTAATAATCATTGAGGTTTACCCTTATAGTTCCGTATTTTCGTTTCCAAACTTAGTAATCTTTTG
GAAATATCATCAAAGCTGGTGCCAATCTTCTTGTTTGAAGTTTCAAACTGCTCCACCAAGCTACTTAGAGACTGT
TCTAGGTCTGAAGCAACTTCGAACACAGAGACAGCTGCCGCCGATTGTTCTTTTTTGTGTTTTTCTTCTGGAAGA
GGGGCATCATCTTGTATGTCCAATGCCCGTATCCTTTCTGAGTTGTCCGACACATTGTCCTTCGAAGAGTTTCCT
GACATTGGGCTTCTTCTATCCGTGTATTAATTTTGGGTTAAGTTCCTCGTTTGCATAGCAGTGGATACCTCGATT
TTTTTGGCTCCTATTTACCTGACATAATATTCTACTATAATCCAACTTGGACGCGTCATCTATGATAACTAGGCT
CTCCTTTGTTCAAAGGGGACGTCTTCATAATCCACTGGCACGAAGTAAGTCTGCAACGAGGCGGCTTTTGCAACA
GAACGATAGTGTCGTTTCGTACTTGGACTATGCTAAACAAAAGGATCTGTCAAACATTTCAACCGTGTTTCAAGG
CACTCTTTACGAATTATCGACCAAGACCTTCCTAGACGAACATTTCAACATATCCAGGCTACTGCTTCAAGGTGG
TGCAAATGATAAAGGTATAGATATTAGATGTGTTTGGGACCTAAAACAGTTCTTGCCTGAAGATTCCCTTGAGCA
ACAGGCTTCAATAGCCAAGTTAGAGAAGCAGTACCAAATCGGTAACAAAAGGGGGAAGCATATAAAACCTTTACT
ATTGCGACAAAATCCATCCTTGAAAGTAAAGCTGTTTGCGGTGTTTAAACCCCAGCGCCTGGCGGG

PRB1 DELETION MS655 (SEQ ID NO: 59)
GACGGCACGGCCACGCGTTTAAACCGCCTGTTCAATTGAACTGGTGTTTGAACAACGCCTACATCAATAATACCA
ATCATCGGACGAAAAATATGGAATTAATACTAAAATATCTTATCCCCTCCAGTCTTATAGTTGGTAAGATACCAA
ATTTGAACATCCTGAACCAGCTGCTGTCATCTCAAGAGGCACACCCTCTGATTGAGCTTTATCGACCACTGATTT
CAACCCTCAAAAAGGGTAATGTTTTCGAATTCCACAAATACCTGTTTGATAATGAGTCATACTTTTTAAAGATGA
ACGTTCTCCTGCCGCTACTTCAACGGTTGCGTATTTTGCTGTTCAGAAATCTGGTCCGAAAGCTGGCCCTTATAG
AGCCACCAGTCAACAACTCTCTGAGATTTTCATCCATCAAAACAGCCCTTTTCGTTTCCATTTCACCCAATCAAA
ACGCATACTTTCAGAACAATTATTCATACCTGATTGTTACCAACGAGTCCCAGATAGACGACTCCTTTGTGGAGA
ACCTCATGATCAGTCTAATCGATCAAAACCTAATTAAGGGTAAACTCGTCAACGATAACCACCGAATAATTGTCT
CCAAGGCCGATACATTCCCGGAGATCCCTACGATTTATTCGACTAAGTTTGCCGTAGACTCGTCATTCGATTGGC
TGGACCAATAGACGTCCTTTTTTTTTTTTATCGTGTCTGCCGTTTAATGTCACGCCTCATGTTTCAAGTTACG
ATAACTTATCATGCAGATACTAAATAGTCACATGACGAATGACGATTTTTTGCGGGTTGCTCAGAGGAATATGCC
TCTGATAAGCGAGGTAAATGTCGAGCATAAGCCACTTACTGTATAAATACCCCTTTATCGCCACTTTATCTTTTC
TCCTTGTCCGTTATCTACAACACCCCAGTAAAACATTACAAACACTCTAGTGTTGTTTTACTGTCCCTTTTAACT
CTCTTCAAACAAATCTCCATATTATTTAAACTCGCTCGTCCAACGCCGGACCTATTGGAGAAAAGGAATACA
CAAGGAGTTAAAAAAGTGTGGTAGAAAGTGCATTTGTCATAATTTTCCATATGTTGCTGTCACTGTAATCTTTT
ATATTTTGTTTTGTTTTATGTAGTATTTCAAAAGGTTCTTATCATCTTACTGGCATAAACTTGATGTACGCAGAG
ATAGCAACCGTTGCTTAGGTAAGCATAGTAAAAATGGCTGGTTTTCTGTCTTATTTTAAGGCCACTGTTGGGACA
AAACACAATAACTAGATTTTATCGGATTGAACAGTGTAAAGGCTTCACTGGCTTATATCTTGTATGAGTACGATA
CATTATCCAGTTCCATCAAGGCCTGTGGAAATATTACAGCCAGGACATGAACCTGAAAGGGAGTTTAGTGGGATC
ACTGTAGATAATAGGAACAGACTTAATGAAGAAAAGTATTATCGACGAAAATAGACGAAGCGTTGAAAAGGGGC
ACAGAAAGACGTTACGTTGATGATCATAGCAGAGGTCATGAGTCTCCAAGTTCAGATTTGGAGGACACTCCGGAT
CAATTCTTGGAATTTCACATTCATGATAACGGAGATAGGAAGATTTCAAGGCCAGACATGCTTCGTCATTGATT
AGTGAAAACGACATGGACTACGATGATTTGTTTGTTGACAGAAAGCAACCAAAACATGCTACTTCTCATGTAAAG
CAGTTTATTAGGAAGAATGTGTTCCAAAAGAAGACTCATCTACCAAACATTGGGGCTAGAGAACTGGAATTACAG
AAACGGCTTGCTTTATTAGAGGGCCCAATAGATGACGATGAGATTATTAGTGCTATGCCCATGGTAGCGTGTCCC
TCTGACTATAACGATCAACCTGCTGATTCAAATTCAACGGTGTTTAAACCCCAGCGCCTGGCGGG

AOX1 DELETION MS530 (SEQ ID NO: 60)
GACGGCACGGCCACGCGTTTAAACCGCCAGATCTAACATCCAAAGACGAAAGGTTGAATGAAACCTTTTTGCCAT
CCGACATCCACAGGTCCATTCTCACACATAAGTGCCAAACGCAACAGGAGGGGATACACTAGCAGCAGACCGTTG
CAAACGCAGGACCTCCACTCCTCTTCTCCTCAACACCCACTTTTGCCATCGAAAAACCAGCCCAGTTATTGGGCT
TGATTGGAGCTCGCTCATTCCAATTCCTTCTATTAGGCTACTAACACCATGACTTTATTAGCCTGTCTATCCTGG
CCCCCCTGGCGAGGTTCATGTTTGTTTATTTCCGAATGCAACAAGCTCCGCATTACACCCGAACATCACTCCAGA
TGAGGGCTTTCTGAGTGTGGGGTCAAATAGTTTCATGTTCCCCAAATGGCCCAAAACTGACAGTCTCAACGCTGT
CTTGGAACCTAATATGACAAAAGCGTGATCTCATCCAAGATGAACTAAGTTTGGTTCGTTGAAATGCTAACGGCC
AGTTGGTCAAAAAGAAACTTCCAAAAGTCGGCATACGCGTTTGCTTCTTGTTTGGTATTGATTGACGAATGCTCAAAA
ATAATCTCATTAATGCTTAGCGCAGTCTCTCTATCGCTTCTGAACCCGGTGCACCTGTGCCGAAACGCAAATGG
GGAAACACCCGCTTTTTGGATGATTATGCATTGTCTCCACATTGTATGCTTCCAAGATTCTGGTGGGAATACTGC
TGATAGCCTAACGTTCATGATCAAAATTTAACTGTTCTAACCCCTACTTGACAGCAATATATAAACAGAAGGAAG
CTGCCCTGTCTTAAACCTTTTTTTTATCATCATTATTAGCTTACTTTCATAATTGCGACTGGTTCCAATTGACAA
GCTTTTGATTTTAACGACTTTTAACGACAACTTGAGAAGATCAAAAAACAACTAATTATTCGAAACGCGCTCGTC
CAACGCCGGCGGACCTTCAAGAGGATGTCAGAATGCCATTTGCCTGAGAGATGCAGGCTTCATTTTTGATACTTT

| INFORMAL SEQUENCE LISTING |
|---|
| TTTATTTGTAACCTATATAGTATAGGATTTTTTTTGTCATTTTGTTTCTTCTCGTACGAGCTTGCTCCTGATCAG
CCTATCTCGCAGCTGATGAATATCTTGTGGTAGGGGTTTGGGAAAATCATTCGAGTTTGATGTTTTTCTTGGTAT
TTCCCACTCCTCTTCAGAGTACAGAAGATTAAGTGAGACGTTTCGTTTGTGCAAGCTTCAACGATGCCAAAAGGGT
ATAATAAGCGTCATTTGCAGCATTGTGAAGAAAACTATGTGGCAAGCCAAGCCTGCGAAGAATGTATTTTAAGTT
TGACTTTGATGTATTCACTTGATTAAGCCATAATTCTCGAGTATCTATGATTGGAAGTATGGGAATGGTGATACC
CGCATTCTTCAGTGTCTTGAGGTCTCCTATCAGATTATGCCCAACTAAAGCAACCGGAGGAGGAGATTTCATGGT
AAATTTCTCTGACTTTTGGTCATCAGTAGACTCGAACTGTGAGACTATCTCGGTTATGACAGCAGAAATGTCCTT
CTTGGGAGACAGTAAATGAAGTCCCACCAATAAAGAAATCCTTGTTATCAGGAACAAACTTCTTGTTTCGAACTTT
TTCGGTGCCTTGAACTATAAAATGTAGAGTGGATATGTCGGGTAGGAATGGAGCGGGCAAATGCTTACCTTCTGG
ACCTTCAAGAGGTATGTAGGGTTTGTAGATACTGATGCCAACTTCAGTGACAACGTTGCTATTTCGTTCAAACCA
TTCCGAATCCAGAGAAATCAAAGTTGTTTGTCTACTATTGATCCAAGCCAGTGCGGTCTTGAAACTGACAATAGT
GTGCTCGTGTTTTGAGGTCATCTTTGTATGAATAAATCTAGTCTTTGATCTAAATAATCTTGACGAGCCAGACGA
TAATACCAATCTAAACTCTTTAAACGCGGTGTTTAAACCCCAGCGCCTGGCGGG |

DNL4 DELETION MS 743 (SEQ ID NO: 61)
GACGGCACGGCCACGCGTTTAAACCGCCCTCCACCGTCTTGATACTTTCTGAGGTGCACAGACCAGAGGATTGTG
CGAACCCTAAATAGTTGTATGAACTCAAATTCAAGCGCTCTGTGACGGTGCCGGAATAATTATAGGTATTGTTGT
AATCGTCACTGGTTCTGTCGTAACATTTGATGTACCTACCGGGAACTCCACATATGGGCCTTGCAAACAGTCAT
CTAATCTTGTTTTCAAACGACGCGTGTAGAAACTTTCAAAATTGGCATACCATGGAGCAATACCATCTTTCACCA
TCACATCTCTGAATAGTTCAGGGTGAAACAACTTCCCAAAGAAGTCTCTAATATGGCCTATTATGATCAAAATAA
GGTAATTAAGGTATGTTGCAATCAGGATGAAATATGGAGGTTCGTCCTCGATGGAACTGGAAGCGGCTCGCCAG
GGTTATGCTTAGAGACAAAGAGCCATTCTTTACTGGTCAAGGACCCAAATTCTTTCTCGGCCTTCTCTTGTGGTG
AATCATTGTCTATGAGAGCATCTGGGATAGTTTTTGACATGATCTTTTTCAGCACGGCTATATAGCAAAAAGCAA
AAAAAAAGACCGAATGGAATTATATGGTCTAAAAAAAACAAACTGGTGGTAAAATAAAAAAAAAACGACTGGTGGG
CGGTTTCAAAGGAGACTAATGATCTTCTATGCCCGCGGAAATAAATAGTACTCCAACGACTGAACTCAGCGGTAT
TAAAGTTTGTGAATAAAATTACAAGGCTTAGAAAGCTTGGTTGGTCTTTCGGTATCGTAGATGGTAGAGTTTTG
AGAACATTTCATTTCCACAGTAACCAACGAACACGACCCGTGACTTCCGGGGGTTGGCAGATGTTAACGCGCGCG
TGGTAGAAGTTTATCTTGGGAGGTGCTAGAGGGTGCTCTTGGCCTTGTTCGCTGGGGGGAAGTGTTTGTAGTTAA
CGTACAACTCCTCATGACTGGGGATCAGAATTTCAACTTGATTTGCCGCTAATCGCTCGTCAACGCCGGCGGAC
CTTAAAAATAATGATTTACATTTAAGAAGTAACAGCACATATATACTGTAAGATTAACTTTGCGTACCCTAAATT
TTACTAATAAACTTAACGGGTTGCCATAGCCTTGGTAACCACACGTTTCAATGCCAATTCAGCTTTTCTGAAGTC
ATCACCGGAAGCATCTTCTAGCTCCAAAGCAGCCAAAGCGTCAGACAAGACAGACTCGATCTTGTCCTTAGCACT
TCTCTTTAGCTTGGAAGACAAAATTGGGTCAGTGATGGTAGACTCAATGGAGGAAACGTAAGCCTCCAACTTCTG
TTTGGATTCGTGACGGTTAGCGAAGTCCTCGTCAGCCTTCTTGAACTTGTCAGCATCGTTGATCATCTTTTCGAT
CTCGGAAGAAGACAATCTACCAATAGAGTTAGAAATAGTGATGTTGGCAGATCTTCCGGTAGACTTCTCGACAGC
GGTAACCTTCAAGATACCGTTGGCATCAATCTCAAAGATAGCCTCCAACACTGGCTCACCAGCAGACATAGGAGG
AATGTTCTTCAAGTCGAACTCACCCAACAAGGTGTTCTCAGAACAGTTGACACGCTCACCCTGGTAAACATGGGAA
TTGAACAGTGGTTTGGTGGTCGTCAACAGTGGTGAAAGTTCTTCTCTTGATAGTTGGGACAGTGGTGTTTCTTGG
AACAACTGGGGCAAAGACGTTACCTTGCATGGCAACACCCAAAGAAAGAGGGATAACATCCAACAACAACAAGTC
CTTGGTCTCTTCAGAGGTAGATTGACCGGTCAAAATAGCACCTTTGAACGGCGGCACCGTAAGCGACAGCCTCATC
AGGGTTGATGGATTTCTCCAATTGCTTACCATCGAAGAAGTCAGACAACAGCTTTTGGACCTTTGGAATTCTGGT
GGAACCACCAACCAAGACGACGTCATCGACCTTGGATTTCTCGATCTTTGAGTCCTTCAAAACTTGTTCAACAGG
CTCCAAAGTAGACTTGAACAAATCAGCGTTGCGGTGTTTAAACCCCAGCGCCTGGCGGG

PEP4 DELETION M5654 (SEQ ID NO: 62)
GACGGCACGGCCACGCGTTTAAACCGCCCGTATCTAATCTTTCTCGCTCCCCGTACGTTAAGAATGAAATTTCTA
CTTCCATTATAGAAAATAGTGTATCACTGCCAGCATCTTTTACTCACAAGCAATTAAACAAAGTAACAATGGTCT
CTAAGCAATTGGAATCACCACAGGGGACCTTTATCACGTTGAATCTAGTTGAAAATTCAGTGTCCAAGTTCGGTG
CAGTACACATACCACAAGGAAAAACCCCATTTGTTGTTGGTAGAGATTCATCTTGTGACTGGTTGATCAAAGAAG
AAAGAATTTCCAAAATACACTGCATGATTGCCAAAAAAAGGCATCCTACTGCTAATCCTTCCATATTTGAGTCAC
CTGCTTTAGGGCTGGAAGATATTTGGTTACTAGATTTTAGTACAAACTCTTGCTTTGTCAATGACATTAAAATAG
GCAAGAATCGCAAAACTCAAATATTTCATGGAGATGAGATATGCTTGTTCAAAGATGCCCAGAAAAAAGAGCAAC
TCGTTTATAGGGTTCATATTGATGATGGAACAGGCCTTTTCCAGGGAGGTGAAAGAACCCAAGCCAATTCTGATG
ACATTCTGGATATTGATGAGGTTGATGAAAAGTTAAGAGAACTATTGACAAGAGCCTCAAGGAAACGGCATATCA
CCCCTGCATTGGAAACTCCTGATAAACGTGTAAAAAGAGCTTATTGAACAGTATTACTGATAACTCTTGATGGA
CCTTAAAGATGTATAATAGTAGACAGAATTCATAATGGTGAGATTAGGTAATCGTCCGGAATAGGAATAGTGGTT
TGGGGCGATTAATCGCACCTGCCTTATATGGTAAGTACCTTGACCGATAAGGTGGCAACTATTTAGAACAAAGCA
AGCCACCTTTCTTTATCTGTAACTCTGTCGAAGCAAGCATCTTTACTAGAGAACATCTAAACCATTTTACATTCT
AGAGTTCCATTTCTCAATTACTGATAATCAATTTAAAGCGCTCGTCAACGCCGGCGGACCTGCAAGAATAAAAG
TTGCTCAGCTGAACTTATTTGGTTACTTATCAGGTAGTGAAGATGTAGAGAATATATGTTTAGGTATTTTTTTTT
AGTTTTTCTCCTATAACTCATCTTCAGTACGTGATTGCTTGTCAGCTACCTTGACAGGGGCGCATAAGTGATATC
GTGTACTGCTCAATCAAGATTTGCCTGCTCCATTGATAAGGGTATAAGAGACCCACCTGCTCCTCTTTAAAATTC
TCTCTTAACTGTTGTGAAAATCATCTTCGAAGCAAATTCGAGTTTAAATCTATGCGGTTGGTAACTAAAGGTATG
TCATGGTGGTATATAGTTTTTCATTTTACCTTTTACTAATCAGTTTTACAGAAGAGGAACGTCTTTCTCAAGATC
GAAATAGGACTAAATACTGGAGACGATGGGGTCCTTATTTGGGTGAAAGGCAGTGGGCTACAGTAAGGGAAGACT
ATTCCGATGATGGAGATGCTTGGTCTGCTTTTCCTTTTGAGCAATCTCATTTGAGACTTATCGCTGGGGAGAGG
ATGGACTAGCTGGAGTCTCAGACAATCATCAACTAATTTGTTTCTCAATGGCACTGTGGAATGAGAATGATGATA
TTTTGAAGGAGCGATTATTTGGGGTCACTGGAGAGGCTGCAAATCATGGAGAGGATGTTAAGGAGCTTTATTATT
ATCTTGATAATACACCTTCTCACTCTTATATGAAATACCTTTACAAATATCCACAATCGAAATTTCCTTACGAAG
AATTGATTTCAGAGAACCGTAAACGTTCCAGATTAGAAAGAGAGTACGAGATTACTGACTCTGAAGTACTGAAGG
ATAACAGATATTTTGATGTGATCTTTGAAATGGCCGGTGTTTAAACCCCAGCGCCTGGCGGG

PEP4 DELETION WITH HERCEPTIN INTEGRATION MS 841 (SEQ ID NO: 63)
GACGGCACGGCCACGCGTTTAAACCGCCCGTATCTAATCTTTCTCGCTCCCCGTACGTTAAGAATGAAATTTCTA
CTTCCATTATAGAAAATAGTGTATCACTGCCAGCATCTTTTACTCACAAGCAATTAAACAAAGTAACAATGGTCT
CTAAGCAATTGGAATCACCACAGGGGACCTTTATCACGTTGAATCTAGTTGAAAATTCAGTGTCCAAGTTCGGTG
CAGTACACATACCACAAGGAAAAACCCCATTTGTTGTTGGTAGAGATTCATCTTGTGACTGGTTGATCAAAGAAG

-continued

INFORMAL SEQUENCE LISTING

```
AAAGAATTTCCAAAATACACTGCATGATTGCCAAAAAAAGGCATCCTACTGCTAATCCTTCCATATTTGAGTCAC
CTGCTTTAGGGCTGGAAGATATTTGGTTACTAGATTTTAGTACAAACTCTTGCTTTGTCAATGACATTAAAATAG
GCAAGAATCGCAAAACTCAAATATTTCATGGAGATGAGATATGCTTGTTCAAAGATGCCCAGAAAAAAGAGCAAC
TCGTTTATAGGGTTCATATTGATGATGGAACAGGCCTTTTCCAGGGAGGTGAAAGAACCCAAGCCAATTCTGATG
ACATTCTGGATATTGATGAGGTTGATGAAAAGTTAAGAGAACTATTGACAAGAGCCTCAAGGAAACGGCATATCA
CCCCTGCATTGGAAACTCCTGATAAACGTGTAAAAAGAGCTTATTTGAACAGTATTACTGATAACTCTTGATGGA
CCTTAAAGATGTATAATAGTAGACAGAATTCATAATGGTGAGATTAGGTAATCGTCCGGAATAGGAATAGTGGTT
TGGGGCGATTAATCGCACCTGCCTTATATGGTAAGTACCTTGACCGATAAGGTGGCAACTATTTAGAACAAAGCA
AGCCACCTTTCTTTATCTGTAACTCTGTCGAAGCAAGCATCTTTACTAGAGAACATCTAAACCATTTTACATTCT
AGAGTTCCATTTCTCAATTACTGATAATCAATTTAAAGCGCTCGTCCAACGCCGGCGGACCTAACAGGAGGGGAT
ACACTAGCAGCAGACCGTTGCAAACGCAGGACCTCCACTCCTCTTCCTCAACACCCACTTTTGCCATCGAAAA
ACCAGCCCAGTTATTGGGCTTGATTGGAGCTCGCTCATTCCAATTCCTTCTATTAGGCTACTAACACCATGACTT
TATTAGCCTGTCTATCCTGGCCCCCTGGCGAGGTTCATGTTTGTTTATTTCCGAATGCAACAAGCTCCGCATTA
CACCCGAACATCACTCCAGATGAGGGCTTTCTGAGTGTGGGGTCAAATAGTTTCATGTTCCCCAAATGGCCCAAA
ACTGACAGTTTAAACGCTGTCTTGGAACCTAATATGACAAAAGCGTGATCTCATCCAAGATGAACTAAGTTTGGT
TCGTTGAAATGCTAACGGCCAGTTGGTCAAAAAGAAACTTCCAAAAGTCGGCATACCGTTTGTCTTGTTTGGTAT
TGATTGACGAATGCTCAAAAATAATCTCATTAATGCTTAGCGCAGTCTCTCTATCGCTTCTGAACCCCGGTGCAC
CTGTGCCGAAACGCAAATGGGGAAACACCCGCTTTTTGGATGATTATGCATTGTCTCCACATTGTATGCTTCCAA
GATTCTGGTGGGAATACTGCTGATAGCCTAACGTTCATGATCAAAATTTAACTGTTCTAACCCCTACTTGACAGC
AATATATAAACAGAAGGAAGCTGCCCTGTCTTAAACCTTTTTTTTTAACATCATTATTAGCTTACTTTCATAATTG
CGACTGGTTCCAATTGACAAGCTTTTGATTTAACGACTTTTAACGACAACTTGAGAAGATCAAAAAACAACTAA
TTATTCGAAACGATGAGATTCCCATCCATCTTCACTGCTGTTTTGTTCGCTGCTTCTTCTGCTTTGGCTGAGGTT
CAGTTGGTTGAATCTGGAGGAGGATTGGTTCAACCTGGTGGTTCTTTGAGATTGTCCTGTGCTGCTTCCGGTTTC
AACATCAAGGACACTTACATCCACTGGGTTAGACAAGCTCCAGGAAAGGGATTGGAGTGGGTTGCTAGAATCTAC
CCAACTAACGGTTACACAAGATACGCTGACTCCGTTAAGGGAAGATTCACTATCTCTGCTGACACTTCCAAGAAC
ACTGCTTACTTGCAGATGAACTCCTTGAGAGCTGAGGATACTGCTGTTTACTACTGTTCCAGATGGGGTGGTGAT
GGTTTCTACGCTATGGACTACTGGGGTCAAGGAACTTTGGTTACTGTTTCCTCCGCTTCTACTAAGGGACCATCT
GTTTTCCCATTGGCTCCCATCTTCTAAGTCTACTTCCGGTGGTACTGCTGCTTTGGGGATGTTTGGTTAAAGACTAC
TTCCCAGAGCCAGTTACTGTTTCTTGGAACTCCGGTGCTTTGACTTCTGGTGTTCACACTTTCCCAGCTGTTTTG
CAATCTTCCGGTTTGTACTCTTTGTCCTCCGTTGTTACTGTTCCATCCTCTTCCTTGGGTACTCAGACTTACATC
TGTAACGTTAACCACAAGCCATCCAACACTAAGGTTGACAAGAAGGTTGAGCCAAAGTCCTGTGACAAGACTCAT
ACTTGTCCACCATGTCCAGCTCCAGAATTGTTGGGTGGTCCTTCCGTTTTTTTGTTCCCACCAAAGCCAAAGGAC
ACTTTGATGATCTCCAGAACTCCAGAGGTTACATGTGTTGTTGTTGACGTTTCTCACGAGGACCCAGAGGTTAAG
TTCAACTGGTACGTTGACGGTGTTGAAGTTCACAACGCTAAGACTAAGCCAAGAGAGGAGCAGTACAACTCCACT
TACAGAGTTGTTTCCGTTTTGACTGTTTTGCACCAGGATTGGTTGAACGGAAAGGAGTACAAGTGTAAGGTTTCC
AACAAGGCTTTGCCAGCTCCAATCGAAAAGACTATCTCCAAGGCTAAGGGTCAACCAAGAGAGCCACAGGTTTAC
ACTTTGCCACCATCCAGAGATGAGTTGACTAAGAACCAGGTTTCCTTGACTTGTTTGGTTAAGGGATTCTACCCA
TCCGACATTGCTGTTGAATGGGAGTCTAACGGTCAACCAGAGAACAACTACAAGACTACTCCACCTGTTTTGGAC
TCTGACGGTTCCTTTTTCTTGTACTCCAAGTTGACTGTTGACAAGTCCAGATGGCAACAGGGTAACGTTTTCTCC
TGTTCCGTTATGCATGAGGCTTTGCACAACCACTACACTCAAAAGTCCTTGTCTTTGTCCCCTGGTAAGTAGACG
CACGCACACTCCCGACAGACAACTAGCTTGATAACAGGCCCCCTTTTCCTTTGTCGATATCATGTAATTAGTTATG
TCACGCTTACATTCACGCCCTCCCCCCACATCCGCTCTAACCGAAAAGGAAGGAGTTAGACAACCTGAAGTCTAG
GTCCCTATTTATTTTTTATAGTTATGTTAGTATTAAGAACGTTATTATATTTCAAATTTTTCTTTTTTTTCTG
TACAAACGCGTGTACGCAATCCCCGCGTGCTTGGCCGGCCGTAAGATTATTACTTGCTATAAGTGCGTGCCTGAT
GAACAGGATATTGCGGTCAATAATGCTGATGGTTCATTAGACTTCAGACAAAGCCGATGCCAAAATAAGCCAATAC
GATCTCAACGCTATTGAAGCGGCTTGCCAGCTAAAGCAACAGGCAGCAGAGGCGCAGGTGACAGCCTTAAGTGTG
GGCGGTAAAGCCCTGACCAACGCCAAAGGGCGTAAAGATGTGCTATCGCGCGGCCCGGATGAACTGATTGTGGTG
ATTGATGACCAGTTCGAGCAGGCACTGCCGCAACAAACGGCGAGCGCACTGGCTGCAGCCGCCCAGAAAGCAGGC
TTTGATCTGATCCTCTGTGGCGATGGTTCTTCCGACCTTTATGCCGACAGGTTGGTCTGCTGGTGGGCGAAATC
CTCAATATTCCGGCAGTTAACGGCGTCAGCAAAATTATCTCCCTGACGGCAGATACCCTCACCGTTGAGCGCGAA
CTGGAAGATGAAACCGAAACCTTAAGCATTCGCTGCCTGCGGTTGTTGCTGTTTCCACTGATATCAACTCCCCA
CAAATTCCTTCGATGAAAGCCATTCTCGGCGCGGCGAAAAAGCCCGTCCAGGTATGGTCGGCGGCGGATATTGGT
TTTAACGCAGAGGCAGCCTGGTCAGAACAACAGGTTGCCGCGCCGAAACAGCGCGAACGTCAGCGCAACGGCCGG
CCAAGCACGCGGGGATTGCGTACACGCGTTTGTACAGAAAAAAAGAAAATTTGAAATATAAATAACGTTCTTA
ATACTAACATAACTATAAAAAAATAAATAGGGACCTAGACTTCAGGTTGTCTAACTCCTTCCTTTTCGGTTAGAG
CGGATGTGGGGGAGGGCGTGAATGTAAGCGTGACATAACTAATTACATGATATCGACAAAGGAAAAGGGGCCTG
TTATCAAGCTAGTTGTCTGTCGGGAGTGTGCGTGCGTCTAACACTCTCCTCTGTTGAAGGACTTAGTAACTGGG
AGGACAAACCCTGATGTGTAACCTCACAAGCGTAAACCTTGTGCTTCTCGTAATCAGCCTTGGACAAAGTCAAAG
TGGAGGACAAGGAGTAAGTGGAGTCCTTAGAGTCTTGCTCAGTAACGGATTCTTGGGAGTTACCGGATTGCAAAG
CGTTGTCAACCTTCCACTGAACCTTAGCCTCTCTTGGGTAGAAGTTGTTCAACAAACAAACAACGGAAGCTGTAC
CAGACTTCAACTGTTCGTCGGATGGTGGGAAAATGAAAACGGATGGAGCAGCAACAGTTCTCTTGATCTCAACCT
TAGTACCCTGTCCGAAAGTTGGTGGAGTAGTGTAGTGCTGCTGACAGTAGTAAGTAGCGAAATCTTCTGGTTGCA
AGGAGGAGATAGTCAAAGTGAAGTCAGTACCGGATCTGGAACCAGAGAATCTGGATGGAACACCAGAGTACAAGA
AGGAAGCGGAGTAGATCAACAACTTTGGAGCCTTTCCTGGCTTCTGTTGATACCAAGCAACAGCAGTATTAACGT
CCTGGGAAGCTCTACAAGTGATAGTAACTCTGTCACCAACGGAAGCAGACAAAGAAGATGGGGATTGAGTCATTT
GGATGTCAGCCAAAGCAGAAGAAGCAGCGAACAAAACAGCAGTGAAGATGGATGGGAATCTCATCGTTTCGAATA
ATTAGTTGTTTTTTGATCTTCTCAAGTTGTCGTTAAAAGTCGTTAAAATCAAAAGCTTGTCAATTGGAACCAGTC
GCAATTATGAAAGTAAGCTAATAATGATGATAAAAAAAAGGGTTTAAGACAGGGCAGCTTCCTTCTGTTTATATAT
TGCTGTCAAGTAGGGGTTAGAACAGTTAAATTTTGATCATGAACGTTAGGCTATCAGCAGTATTCCCACCAGAAT
CTTGGAAGCATACAATGTGGAGACAATGCATAATCATCCAAAAAGCGGGTGTTTCCCCATTTGCGTTTCGGCACA
GGTGCACCGGGGTTCAGAAGCGATAGAGAGACTGCGCTAAGCATTAATGAGATTATTTTTGAGCATTCGTCAATC
AATACCAAACAAGACAAACGGTATGCCGACTTTTGGAAGTTTCTTTTTGACCAACTGGCCGTTAGCATTTCAACG
AACCAAACTTAGTTCATCTTGGATGAGATCACGCTTTTGTCATATTAGGTTCCAAGACAGCGTTTAAACTGTCAG
TTTTGGGCCATTTGGGGAACATGAAACTATTTGACCCCACACTCAGAAAGCCCTCATCTGGAGTGATGTTCGGGT
GTAATGCGGAGCTTGTTGCATTCGGAAATAAACAAACATGAACCTCGCCAGGGGGCCAGGATAGACAGGCTAAT
AAAGTCATGGTGTTAGTAGCCTAATGAAAGGAATTGGAATGAGCGAGCTCCAATCAAGCCCAATAACTGGGCTGG
TTTTTCGATGGCAAAAGTGGGTGTTGAGGAGAAGAGGAGTGGAGGTCCTGCGTTTGCAACGGTCTGCTGCTAGTG
```

TATCCCTCCTGTTAGGTCCGCCGGCGTTGGACGAGCGGCAAGAATAAAAGTTGCTCAGCTGAACTTATTTGGTT
ACTTATCAGGTAGTGAAGATGTAGAGAATATATGTTTAGGTATTTTTTTTAGTTTTTCTCCTATAACTCATCTT
CAGTACGTGATTGCTTGTCAGCTACCTTGACAGGGGCGCATAAGTGATATCGTGTACTGCTCAATCAAGATTTGC
CTGCTCCATTGATAAGGGTATAAGAGACCCACCTGCTCCTCTTTAAAATTCTCTCTTAACTGTTGTGAAATCAT
CTTCGAAGCAAATTCGAGTTTAAATCTATGCGGTTGGTAACTAAAGGTATGTCATGGTGGTATATAGTTTTTCAT
TTTTACCTTTTACTAATCAGTTTTACAGAAGAGGAACGTCTTTCTCAAGATCGAAATAGGACTAAATACTGGAGAC
GATGGGGTCCTTATTTGGGTGAAAGGCAGTGGGCTACAGTAAGGGAAGACTATTCCGATGATGGAGATGCTTGGT
CTGCTTTTCCTTTTGAGCAATCTCATTTGAGAACTTATCGCTGGGGAGAGGATGGACTAGCTGGAGTCTCAGACA
ATCATCAACTAATTTGTTTCTCAATGGCACTGTGGAATGAGAATGATGATATTTGAAGGAGCGATTATTTGGGG
TCACTGGAGAGGCTGCAAATCATGGAGAGGATGTTAAGGAGCTTTATTATTATCTTGATAATACACCTTCTCACT
CTTATATGAAATACCTTTACAAATATCCACAATCGAAATTTCCTTACGAAGAATTGATTTCAGAGAACCGTAAAC
GTTCCAGATTAGAAAGAGAGTACGAGATTACTGACTCTGAAGTACTGAAGGATAACAGATATTTTGATGTGATCT
TTGAAATGGCGGCGGTTTAAACGCGTGGCCGTGCCGTC pTDH3 > VTH1 MS637 (SEQ ID NO: 64)
GACGGCACGGCCACGCGTTTAAACCGCCACCGTCAATATGAAGAATAACACTAACCAGTA
TTTTGAAAAGAAGAAAGCCATTAATGAAATCGTCAAATCAATTCATTCCAATTTGGAAGC
TTCTTTATTTAGTTCACTAAAACGCTCAGATATGGCATCTCAAACTCTCCCCTATGTTTA
TCATATCATACTGCCTAACTTCAAAAACATGGCCAGATTAATCAGCCTGAAACCTGAAGA
AAAGATCAAACTTACGGAAGCTGCAAAAGTTCTTAAAGAGTTTGGCTTCACGATTGAGCA
AGCAAAAGATGAAACTTTCACTTACATTCAAAAACTAGTTCCGCCAATTGATACCGTAGT
CAATTGTCAGAACGAATTATCGCATCAAAAGTCACTTTGCGCACGAGCTAATCAGATTCT
CCCATACATTGAGATTGAGTTGAAAAGGTTGAACATCACCAAGAGACACCTAACCGATTC
TGAGCAAGACTTCAAGAAACTACAAGGTACTTCAAAGAGAAGAATCACAGGGTTGACCTC
CCCTAGTAATCGACAGTCGCGTGCCGCATCTCTTCAGGAGGGGGGGCAGACTCAAAATCA
GCTGGGTACCTCTATAGATTTTTTCGCCAAATCGCTTTCCCGAGATGGAAGCTCAGGCAG
AACGACACCTGCACCTCAGACGAACTCTCAGAGAGGCACCACCGGACGTATTTGGGTCCG
TTATAACGAAGGGTTCTCAAATGCAGTTCGTAGAAACATCACATGGGAAGAGCTGTGGAA
TTTTTAAATGTCCTCCATAATTTCATGCGGACCTTGCATAGTTTATATAATCATACTGTA
CCAACCAACATCCACACAAGGAGTTTTCGGCCTCAACATATTATCGAAACCATCTCCCTG
TCCCTTACTCAGATCCTATTTTTTCTTACTCAATTGAACGCTCGTCCAACGCCGGCGGAC
CTCCTTAACTACGTTAGGTCAGTGATGACAATGGACCAAATTGTTGCAAGGTTTTTCTTT
TTCTTTCATCGGCACATTTCAGCCTCACATGCGACTATTATCGATCAATGAAATCCATCA
AGATTGAAATCTTAAAATTGCCCCTTTCACTTGACAGGATCCTTTTTTGTAGAAATGTCT
TGGTGTCCTCGTCCAATCAGGTAGCCATCTCTGAAATATCTGGCTCCGTTGCAACTCCGA
ACGACCTGCTGGCAACGTAAAATTCTCCGGGGTAAAACTTAAATGTGGAGTAATGGAACC
AGAAACGTCTCTTCCCTTCTCTCCTTCCACCGCCCGTTACCGTCCCTAGGAAATTTTA
CTCTGCTGGAGAGCTTCTTCTACGGCCCCCTTGCAGCAATGCTCTTCCCAGCATTACGTT
GCGGGTAAAACGGAGGTCGTGTACCCGACCTAGCAGCCCAGGGATGGAAAAGTCCCGGCC
GTCGCTGGCAATAATAGCGGGCGGACGCATGTCATGAGATTATTGGAAACCACCAGAATC
GAATATAAAAGGCGAACACCTTTCCCAATTTTGGTTTCTCCTGACCCAAAGACTTTAAAT
TTAATTTATTTGTCCCTATTTCAATACCTCCCGCGACCTCCAAAATCGAACTACCTTCAC
AATGAGGACATTGACATTGTTGGTCTACTTCGTAGTGGCTGCCTTAGCTTTCACCCCGCA
GACCAACTCCAGAATTTTTAAAGGTTACCCAAAGAAAGTGGTTTATTTTGACGACACTGC
CAGCGTTGTCTACCATGATGGCTCTGACAATGAGATCTATTATTCCAAAGATGATGGTGT
CACTTGGACTCAACTAGATCTTGGTGGGGCGTCCGCTCATCAAGTAATTGTTCACCCTTT
TGACCCTTCTACTGCCTATATTTTGACCACTAGTGAAACTCACTTCGTCACCACAGATAG
CGGATTTACTTGGAATAAGGTTTCCTCTCCAGAGCCTCCAGTAACCAACGAGTTTCCAAC
GTTGAGCCAAGAGTCCTCCTCATTGACCCTGAATTCCAAGAACTTTGAGTATGTTCTGTT
TGCAGGCCAATGTACAGACGGATCAGAAATTTGCAACAGAAAGTACTACTATTCCTTGGA
TAACATGAGAACTTTCAACGAGCTCATTGAAGCTCACAGCTGTTTGTTTGTCGATACTGC
CGATGCCATTGCGGGTGATCATTCCCCAAACGCTGTTATCTGTGCCATCACCAACCCTGA
CGGAAAACTGTCTTTGGTGAAAACCGCCAACTTCTTCAAAGACGGCATAGACTATGTCTC
TAGTGGTGGTGGTCTTATTGAGAATCCTGAACTGCTGGGCGCCTCACACAACTACATCTT
GGCTGTTGGTTCTCATCTTTTGCACAACAAAGACAAGTTTGTATACATCTCATTTGATGG
TTCGAACTTCAACAAAGTGACGGTGTTTAAACCCCAGCGCCTGGCGGG pTDH3 > CNE1, MS628 (SEQ ID NO: 65)
GACGGCACGGCCACGCGTTTAAACCGCCTCTCTGCTCTTCAAGAAGTAAAACGCTGGGCG
GCAAAGAAGGAAAAGTCCAATAAAAGTATCTGTAAGAGGTGGAAGTGCTCAGATAGTGCG
AAGAGAGGAATAAATGAATGCAAGAGCGCGATGGAGTGTAGCGTGATTACATCATCAGAT
GCTACATTGATTCTCTGATATGAATGGTGATGGAACTTTCTAGAGGTTCCTTGAAGAAAT
AAATACATTTACAAGCAGAACTCCACTTTTTCACGGAGAATCATCTAAGTTAGGCATACG
AAGGATCTCGCCTTCGTTGTTTGCACTCATCTCCTGTAGTTTAGCGAGAATCTTGGAGTC
CTTCCACTTTTCAGGCAATGGGGTAACCTCGTAGTTTTTCACGGCCCAGTAATAAATATC
CCAATCCAACTCGTTTAATAAGTCATCATACTCTTCCATCTTTCCACACTCATTGTCGG
TAGATAGCGTTTTGCGAAACGAGACAGAAGAAGGTCTGTTTCCAAGATTCCTCTCTTTCT
TGACTGATAAACCAGACGGCGTCTCTTGACATCTTCCGACTCGTTATCACGTTTCAGAGG
TTCAACTTTCAGTATCAGCTCCTGCCTCAAGAAGGGGAGAGAATGAAAAGATTTCGAAAA
CACCCTTGGACAAGTCTTGCTACCTTGAAACTGAGTTCTTTGGAAAAGCCGGAGCATAAT
GGGTGAATTAAGCAGAAAGAAGGTAACTGATTTGCTGAGACCCAAATCATCTACAGTTTC
GCGAAGCATAAAGTTCACACTGATTTTCTGGGGAAGAACTGGTAAACACATGTGTCTC
CATTCCACGATAAACCGTTCAAGCAAGGCCGTCTTAGAATGCACAAGACAATTTAGGTAA
ACTACCTTTCCTGGAAGCGAAAGCAGACGTTACAATCTGTTTCATCCCCAACTGCACTC
CTCTCTCCTCTGCTAGCCAAGACGATCTTTCATAGAATTTGATGGAATTTACGCGAAATC
GCCACGTAATCATATTTCGAACAGCGCTCGTCCAACGCCGGCGGACCTCCTTAACTACGT
TAGGTCAGTGATGACAATGGACCAAATTGTTGCAAGGTTTTTCTTTTTCTTTCATCGGCA

| INFORMAL SEQUENCE LISTING |
|---|
| CATTTCAGCCTCACATGCGACTATTATCGATCAATGAAATCCATCAAGATTGAAATCTTA
AAATTGCCCCTTTCACTTGACAGGATCCTTTTTTGTAGAAATGTCTTGGTGTCCTCGTCC
AATCAGGTAGCCATCTCTGAAATATCTGGCTCCGTTGCAACTCCGAACGACCTGCTGGCA
ACGTAAAATTCTCCGGGGTAAAACTTAAATGTGGAGTAATGGAACCAGAAACGTCTCTTC
CCTTCTCTCTCCTTCCACCGCCCGTTACCGTCCCTAGGAAATTTTACTCTGCTGGAGAGC
TTCTTCTACGGCCCCCTTGCAGCAATGCTCTTCCCAGCATTACGTTGCGGGTAAAACGGA
GGTCGTGTACCCGACCTAGCAGCCCAGGGATGGAAAAGTCCCGGCCGTCGCTGGCAATAA
TAGCGGGCGGACGCATGTCATGAGATTATTGGAAACCACCAGAATCGAATATAAAAGGCG
AACACCTTTCCCAATTTTGGTTTCTCCTGACCCAAAGACTTTAAATTTAATTTATTTGTC
CCTATTTCAATACCTCCCGCGACCTCCAAAATCGAACTACCTTCACAATGAAGATCTCTA
CCATTGCAAGTTCTACGTTGTTCGCTGTTGGTGCTTTAGCCGAATCCGAACCCGCTGAGT
TCAGACCCTTGGAAGCTCAGTTGGACAAGTCATCTTTCTTTGAACAATTCGACAAGGAAC
CGAAACTCGGCGACACCTGGAAGATCTCCCATGCCGTTAAGAATGAAGAATTCACTTATG
TTGGAGAATGGGCCATTGAGGAACCTGTTGTCTATCCTGGATTCAAGAAGGACAGGGGTC
TGGTTGTGAAATCTGAGGCAGCTCACCACGCAATATCTGCCCAATTACCACAGGTATTTG
ACAACACTGACAATACGTTGGTCTTGCAATACGAAGTCAAGCTTCAACAAGGATTGAACT
GTGGAGGTGCTTATGTTAAATTATTGAGTGCTGAGGGTCTGAACAAGAATGAGTTCTCTA
ACGAGACCCTTATCAAGTCATGTTTGGTCCTGATAAATGTGGAACCACGAATAAAGTGC
ACTTGATTATTAAGAGGAAGAACCCAGCCACCGGCGAATATGAGGAACATCAATTGGCTA
CTCCTCCAATGGGTAGAATCGTCAAGACTACTTCTCTATACACCCTGATTATCAAGCCCA
ATAATGACTTTGAAATCAGAATCAACGGTGAGGTTGCTAAAGCTGGTAACTTGTTGAACG
AGAAGTTGATAAAGCCACCATTTGGCGCTCCGAAGGAGATTGACGATCCGGAAGACCAAA
AACCCGAAGATTGGGTTGATGAAGACATGATCCCAGATCCAGATGCTGTCAAGCCTGAAG
ATTGGGACGAGTCCGAGCCATTGCGAATCGTCGATCCGGAAGCTGTGAAACCAGAAAACT
GGAACGAAGATGCTGAATTGTACATCCCTGATCCAGAGGCCACCAAGCCCGAAGACTGGG
ACGATGAAGAGGATGGCGAATGGGTTGCTCCTGTTATTCCAAATCCAGAATGCGCAGATA
TTGGATGTGGCCCTTGCGGTGTTTAAACCCCAGCGCCTGGCGGG pTDH3 > ECM10, M5766 (SEQ ID NO: 66)
GACGGCACGGCCACGCGTTTAAACCGCCGATTGTCTTCAAACATTTACACTGAGTGTTGG
AACCATTAAGTTGCCATATTTGAGCCGTCGAATCTTTGGCGACGGTGACAAATATCAGTT
CATCAACTGTATCCCAAGCAATGCAATAGACTGGCTTGTTAGAGGTTGTATTGATCTGCA
ATAAAGAGTCCCATACATTTTCCTTGAACCTTTTCCATATGCAGAGGGTTTTATCAGATC
TTGAATACGCCAATCTATTTCCCTTGTTGAATTCTAAAGTGATGATATCAGTGCTAGTTC
GGTGATTTTCTAAAGAGCCATCATTCAACTCCGTTGATTTCAGATCAGTAAAAAGCTGCT
TGTCCCTAGCTAGTGAAGGGTTGGTCATTATAGAGGCCTTCAAACAATACTTTTCAAAAT
AGACACGCCGCGCGAATCCTCACGATAGCGAAATACCAACTCCACAGATGTTACCACGTA
ACATTTCTCCTCTGATCAAATGGCTCCTCAAACACCAAGGCAACGTATCGCAAACGAAAA
ATTCGTAAAGAGAGCTGAAGCTCAGCAGGGTAAGGTGAAGAAGGCTAGATCCAAGCGTGA
ATTTCCAGTTTCGACTAAGTGGGTTATCATATTGCTCTTCTTGCTGATTGGGGGAGGGGT
CCTGGAGATTTTGAGATTGTTTTTTTGAATGATCTTTTCAAAGGTCTAGGTCTTTTTGGA
AGGAAATGGTTATACTTTGGCCTTTCATTATTTGAGAGGATAGTCGTATTTTTCTACCGG
GAGAAGGTAGGCATAACGTTAATTGCGAATTTTCACTTACTTTAGATGGGTACTGATCTT
CAACTCACGATAATTTCATTGCACCATGTATCTCTAAACTGGCGTGTCGGAACTCACACA
CCATTGGAACTTATTGATTAACCAATACATAGATTAATTGACTCGCCTGATAATACTAAT
CACCGTTCACTACTTCTCTTAGTATCTTCTCCTACTGGAGTCGTTCTACGCTCGTCCAAC
GCCGGCGGACCTCCTTAACTACGTTAGGTCAGTGATGACAATGGACCAAATTGTTGCAAG
GTTTTTCTTTTTCTTTCATCGGCACATTTCAGCCTCACATGCGACTATTATCGATCAATG
AAATCCATCAAGATTGAAATCTTAAAATTGCCCCTTTCACTTGACAGGATCCTTTTTTGT
AGAAATGTCTTGGTGTCCTCGTCCAATCAGGTAGCCATCTCTGAAATATCTGGCTCCGTT
GCAACTCCGAACGACCTGCTGGCAACGTAAAATTCTCCGGGGTAAAACTTAAATGTGGAG
TAATGGAACCAGAAACGTCTCTTCCCTTCTCTCTCCTTCCACCGCCCGTTACCGTCCCTA
GGAAATTTTACTCTGCTGGAGAGCTTCTTCTACGGCCCCCTTGCAGCAATGCTCTTCCCA
GCATTACGTTGCGGGTAAAACGGAGGTCGTGTACCCGACCTAGCAGCCCAGGGATGGAAA
AGTCCCGGCCGTCGCTGGCAATAATAGCGGGCGGACGCATGTCATGAGATTATTGGAAAC
CACCAGAATCGAATATAAAAGGCGAACACCTTTCCCAATTTTGGTTTCTCCTGACCCAAA
GACTTTAAATTTAATTTATTTGTCCCTATTTCAATACCTCCCGCGACCTCCAAAATCGAA
CTACCTTCACAATGTTGTCATCAAGATGGTGTTCATGTAAAAAGCAGAGTCCAAGTCGAC
AAGTAGGTCAGTTACTGCGCTACATGTCTAGCAAGGTAATTGGAATTGATTTAGGAACTA
CGAACTCTGCTGTTGCCGTTTTTGAAGGAAAAGAACCAAAAATCCTGGAGAACGAAGAGG
GAAAGAGAACGACACCTTCTATTGTTGCATTTACCCCAGAAACTGTGCTAGTAGGAGAAC
CAGCAAAGAGACAATCTATTCTGAACTATCAGAACACTTTTTATGCTACAAAAAGGCTCA
TTGGTCGCAAGTATTCGGATCCTGAAGTTCAACGGGATATTTCCAACGTTCCTTACAGTA
TAATTGAACATGAAAATGGGGATGCGTGGCTTCAAAACATGCACTCAGGTCAAAAATACT
CCCCCTCTCAAATTGGTAGTTTGATATTGGGAAAGATGAAAGAGATTGCAGAGCTAAATC
TTTCCCAGTCTATTAGCCAGGCTGTGGTCACTGTGCCTGCCTACTTCAACGATTCGCAAA
GACAAGCAACTAAGATTGCTGGTGATTTAGTGGGTCTTAAAGTTTTAAGAGTTATCAATG
AGCCCACCGCTGCTTCTTTGGCTTACGGATTGAATAGAAAAAATGACGGGATAATTGCCG
TTTACGACCTTGGTGGTGGAACTTTTGATATCTCCATATTGGATATCGAAGCCGGCGTCT
TTGAAGTTATTGCGACGAATGGTGACACACATCTTGGAGGGGAAGATTTGACCATTTGC
TGGTGGACTACATATTGCAACAGTTTCAATCGCAGACAGGACAAGATCTATCTACTGACC
GTTTGGCCCTGCAAAGAATTCGTCAGGCTGCTGAAAACGGTGTTTAAACCCCAGCGCCTG
GCGGG pTDH3 > ERO1, MS632 (SEQ ID NO: 67)
GACGGCACGGCCACGCGTTTAAACCGCCAGAATCACAAAATTCTTTTCATCTTCAGACAT
GTATATCTGGCTCAGAGATTTGAAGGGAATCTGAAACCTGGTTTTAGACGGAAGGTCAAC |

-continued

INFORMAL SEQUENCE LISTING

```
TATGAGGTACAGGCTGTTAGGCCATATGCTTAAAAAAGGAACAGGTAAGGATATGTTTTT
ATTGATGATGGAGATGTGGTGCAAGTGAATCCTGAGAACCTCTTTTTTCTTTTCAAACGC
ATTTTTGTCTTCAATTCCATTCTTCGATCTTTTAACGATGGGAGCGCTTATTTTGTCTAT
GATGTGGCTTTGAAGATCAGCTGTTGTATTCAAACTATCACTTTGAGTCAACGAGTTCTT
AGGTAGTCTTTGAAACCGTGAAAGGGAACCCATTTTCTTCGAACCCAGGGATTTCACTGA
TCCTCTGGCCATTGACGCCGATCGTGAGTTCTGTAGAGTTCCCTTCGTCTTAAGAGAGAG
GGGGAATAATTAAAGATCAAGTAATGTTCTACCTACAAAAGATAAAGATGACCTTAATGT
TTTTAGCGAGGTATAGCTGGGAGTCCCAAAGAAGTAGCTAGGGCGGTGAGAGGATTTTTT
TCTCGTGCGCATATAATCGCTAGCCTAGTTAAAGCATCTTGACGACGTACTAATATCTGG
AAGACTTCAGAGCACAGAAACTATGCCTGGTGAGTTCATGGTGACCGTATTGAGCACATC
CAAAAAGATCTTATTCTCTCCAGTACAATCAGCAGAAGGCCTTATCCATCTTGCTGTTCC
ACTACCTCATTCCAGTATACTTCTAATCATCGCCTCTAGATAAGCCAGACGATCTCAAGA
ACCACCCTCATCTTGAAACGTGGACTCGAGTCGCAATGTCCTGTATCATTCCTACGTCAC
AAGCCATCACTGGGTTCTCTCGCCCCCCTACGAAACGCTAGCTATTGCTATATGGAACAA
TCTAGACCGTAAGTTAGGGCCACTCTGTTCATTTCTCGTCTTAGTCAGCTGATCCTCGAA
ACGATCTACGCTCGTCCAACGCCGGCGGACCTCCTTAACTACGTTAGGTCAGTGATGACA
ATGGACCAAATTGTTGCAAGGTTTTTCTTTTTCTTTCATCGGCACATTTCAGCCTCACAT
GCGACTATTATCGATCAATGAAATCCATCAAGATTGAAATCTTAAAATTGCCCCTTTCAC
TTGACAGGATCCTTTTTTGTAGAAATGTCTTGGTGTCCTCGTCCAATCAGGTAGCCATCT
CTGAAATATCTGGCTCCGTTGCAACTCCGAACGACCTGCTGGCAACGTAAAATTCTCCGG
GGTAAAACTTAAATGTGGAGTAATGGAACCAGAAACGTCTCTTCCCTTCTCTCTCCTTCC
ACCGCCCGTTACCGTCCCTAGGAAATTTTACTCTGCTGGAGAGCTTCTTCTACGGCCCCC
TTGCAGCAATGCTCTTCCCAGCATTACGTTGCGGGTAAAACGGAGGTCGTGTACCCGACC
TAGCAGCCCAGGGATGGAAAAGTCCCGGCCGTCGCTGGCAATAATAGCGGGCGGACGCAT
GTCATGAGATTATTGGAAACCACCAGAATCGAATATAAAAGGCGAACACCTTTCCCAATT
TTGGTTTCTCCTGACCCAAAGACTTTAAATTTAATTTATTTGTCCCTATTTCAATACCTC
CCGCGACCTCCAAAATCGAACTACCTTCACAATGAGGATAGTAAGGAGCGTAGCTATCGC
AATAGCCTGTCATTGTATAACAGCGTTAGCAAACCCTCAAATCCCTTTTGACGGCAACTA
CACCGAGATCATCGTGCCAGATACCGAAGTTAACATCGGACAGATTGTAGATATTAACCA
CGAAATAAAACCCAAACTGGTGGAACTGGTCAACACAGACTTCTTCAAATATTACAAATT
AAACCTATGGAACCATGTCCGTTTTGGAATGGTGATGAGGGATTCTGCAAGTATAAGGA
TTGCTCTGTCGACTTTATCACTGATTGGTCTCAGGTGCCTGATATCTGGCAACCAGACCA
ATTGGGTAAGCTTGGAGATAACACGGTACATAAGGATAAGGGCCAAGATGAAAATGAGCT
GTCCTCAAATGATTATTGCGCTTTGGATAAAGACGACGATGAAGATTAGTATATGTCAA
TTTGATTGATAACCCTGAAAGATTCACCGGTTATGGTGGTCAGCAATCTGAATCTATTTG
GACTGCGGTCTATGATGAGAACTGTTTCCAGCCGAATGAAGGATCACAATTGGGTCAAGT
TGAAGACCTCTGTTTGGAGAAACAGATCTTTTACCGATTGGTTTCTGGTTTGCATTCTAG
TATCTCCACCCACCTCACAAACGAATATCTGAATTTGAAAATGGAGCATACGAACCAAA
TTTGAAACAGTTCATGATCAAAGTTGGGTATTTTACTGAAAGAATTCAAAACTTACATCT
CAATTATGTCCTTGTATTGAAGTCACTAATAAAGCTACAAGAATACAATGTTATCGACAA
TCTACCTCTCGATGACTCTTTGAAAGCTGGTCTTAGCGGTTTAATATCTCAAGGAGCACA
GGGTATTAACCAGAGCTCTGATGATTATCTATTTAACGAGAAGGTTCTTTTCCAAAATGA
CCAAAATGATGATTTGAAAAATGAATTCCGTGACAAATTCCGCAACGTGACTAGATTAAT
GGATTGTGTCCACGGTGTTTAAACCCCAGCGCCTGGCGGG
```

What is claimed is:

1. A method of producing an antibody, the method comprising,
culturing a yeast host cell comprising (i) a nucleic acid sequence encoding an antibody in the yeast host cell genome and (ii) a circular extrachromosomal nucleic acid comprising a coding sequence for a selectable marker, under conditions suitable for production of the antibody, wherein the host cell further comprises a nucleic acid that encodes an RNA-guided DNA endonuclease, wherein the nucleic acid is integrated in a YKU70 gene, thereby reducing non-homologous end joining (NHEJ) activity in the host cell as compared to a host cell in which YKU70 is intact; and
recovering the antibody produced by the yeast host cell.

2. The method of claim 1, wherein the host cell is *Pichia*.

3. The method of claim 2, wherein the host cell is *Pichia pastoris*.

4. The method of claim 2, wherein the nucleic acid encoding the RNA-guided DNA endonuclease is operably linked to a *Pichia* pPGK1 promoter.

5. The method of claim 1, wherein the RNA-guided DNA endonuclease is Cas9.

6. The method of claim 5, wherein the yeast host cell is a *Saccharomyces* yeast host cell and the nucleic acid sequence encoding the Cas9 is codon optimized for expression in *Saccharomyces*.

7. The method of claim 5, wherein the yeast host cell is a *Pichia* yeast host cell and the nucleic acid sequence encoding the Cas9 is codon optimized for expression in *Pichia*.

8. The method of claim 7, wherein the *Pichia* yeast host cell is a *Pichia pastoris* yeast host cell.

9. The method of claim 3, wherein BMT1, BMT2, BMT3, BMT4, PNO1, MNN4-1, MNN4-2, MNN4-3, PRB1, PEP4, AOX1, or DNL4 are deleted.

10. The method of claim 3, wherein PEP4 is deleted.

11. The method of claim 3, wherein VTH1, CNE1, ECM13, and ERO1 are overexpressed.

12. The method of claim 1, wherein the antibody is trastuzumab.

13. The method of claim 12, wherein the nucleic acid sequence encoding the antibody coding sequence is codon-optimized for the yeast host cell.

14. The method of claim 1, wherein the antibody is rituximab.

15. The method of claim 14, wherein the nucleic acid sequence encoding the antibody coding sequence is codon-optimized for the yeast host cell.

16. The method of claim 1, wherein the antibody is BIIB.

17. The method of claim 16, wherein the nucleic acid sequence encoding the antibody coding sequence is codon-optimized for the yeast host cell.

18. A method of producing an antibody, the method comprising,
culturing a *Pichia* host cell comprising (i) a nucleic acid sequence encoding an antibody in the *Pichia* host cell genome and (ii) a circular extrachromosomal nucleic acid comprising a coding sequence for a selectable marker, under conditions suitable for production of the antibody, wherein the *Pichia* host cell further comprises a nucleic acid that encodes an RNA-guided DNA endonuclease, wherein the nucleic acid is integrated in a YKU70 gene, thereby reducing non-homologous end joining (NHEJ) activity in the *Pichia* host cell as compared to a *Pichia* host cell in which YKU70 is intact and wherein the nucleic acid encoding the RNA-guided DNA endonuclease is operably linked to a *Pichia* pPGK1 promoter; and
recovering the antibody produced by the *Pichia* host cell.

19. The method of claim 18, wherein the *Pichia* host cell is a *Pichia pastoris* host cell.

* * * * *